United States Patent
Bratton et al.

(10) Patent No.: US 7,067,538 B2
(45) Date of Patent: Jun. 27, 2006

(54) MCP-1 RECEPTOR ANTAGONISTS AND METHODS OF USE THEREOF

(75) Inventors: Larry D. Bratton, Whitmore Lake, MI (US); Alexander J. Bridges, Saline, MI (US); David T. Connor, Ann Arbor, MI (US); Steven R. Miller, Ann Arbor, MI (US); Yuntao Song, Ann Arbor, MI (US); Kuai-Lin Sun, Canton, MI (US); Bharat K. Trivedi, Farmington Hills, MI (US); Paul C. Unangst, Ann Arbor, MI (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 149 days.

(21) Appl. No.: 10/442,917

(22) Filed: May 21, 2003

(65) Prior Publication Data

US 2005/0171163 A1 Aug. 4, 2005

Related U.S. Application Data

(60) Provisional application No. 60/402,409, filed on Aug. 9, 2002.

(51) Int. Cl.
*A01N 43/40* (2006.01)
*A61K 31/44* (2006.01)

(52) U.S. Cl. ............... 514/343; 514/365; 514/372; 514/374; 514/396; 514/709; 546/272.1; 546/339; 548/200; 548/214; 548/215; 548/338.1; 549/78; 564/123; 568/31

(58) Field of Classification Search ............... 514/340, 514/365, 372, 374, 396, 709; 546/272.1, 546/339; 548/200, 214; 549/78; 564/123; 568/31
See application file for complete search history.

(56) References Cited

U.S. PATENT DOCUMENTS 5,183,729 A * 2/1993 Naito et al. ............... 430/385
5,321,000 A * 6/1994 Brannigan et al. .......... 504/110

FOREIGN PATENT DOCUMENTS

| WO | WO 99/26615 A | 6/1999 |
|----|---------------|--------|
| WO | WO 01/07424 A1 | 2/2001 |
| WO | WO 0/2060859 A | 8/2002 |

OTHER PUBLICATIONS

Springer, Timothy A., Nature, 1990, vol. 346, pp. 425-434.
Lawrence, Michael B. et al., Cell, vol. 65, 859-873, May 31, 1991.
Butcher, Eugene C., Cell, vol. 67, pp. 1033-1036, Dec. 20, 1991.
Ernst, C.A. et al., J. Immunol., 1994;152:(3541-3544).
Spangrude et al. J. Immunol. 1985;135(6):4135-4143.
Nourshargh and Williams J. Immunol. 1990;145(8):(2633-2638).
Sekido et al., Nature 1993;365(6447):654-657.
Hechtman et al. J. Immunol. 1991;147(3):883-892.
Huber et al., Science 1991;254(5028):99-102.
Carr et al. Proc. Natl. Acad. Sci. USA. 1994;91(9):3652-3656.
Kice J.L. and Rudzinski J.J., J. Am. Chem. Soc. 1987;109:2414.
Klenk M.M.; Suter C.M., Archer S., JACS 1948;70:3846.
McKennis, H. et al., JOC, 1963;28:383.
Heffner R.J. et al., Synth. Commun. 1991;21,2231-2256.
Khurana J.M. et al. G.C. J. Chem. Soc. Perkin Trans, 1996;1:2213.
Carceller E. et al., J. Med. Chem. 1993;36:2984.
Babu S.D. et al., Can. J. Chem. 1989;67:1071.
Dhainaut A. et al., J. Med. Chem. 2000;43:2165-2175.
Newman, J. Org. Chem. 1948;13:592.
Edwards. J. Org. Chem. 1964;29:913.
Olah, Synthesis 1984:228.
Hlasta, Tetrahedron Lett. 1989;vol. 30 No. 14:1773-76.
Nahm, Tetrahedron Lett. 1981;22:3815.
Ogura F., et al., Bull. Chem. Soc. Jpn 1983;56:1257-1258.
Wissner A. J., Org. Chem. 1979;44:4617-4622.
Langer P. et al., Syn. Lett. 2000;6:844-846.
Hirschmann R., J. Org. Chem. 2000;65:8307-8316.
Grossert J.S. et al., Can. J. Chem. 1984;62:798.
Kiyoaki K., et al. Bioorg. Med. Chem. Lett. 1996;6:2601-2606.
Abdel-Magid A.F. et al., J. Org. Chem. 1996;61:3849-3862.
Malinka W., Pol. J. Chem. 1995;69:95-102.
Ikechukwu I. Ekekezie, et al., Pediatric Research, vol. 50, No. 5, 2001 pp. 633-640.
Gibson J.A. et al., Can J. Chem. 1975;53:3044-3052.
Domenico et al., Synthesis 1994:34-36.
Kraynack and Pedersen JOC 1993;58(22); 6114-6117).
Schmidt et al., Synthesis 1987:896.
Berge S.M. et al., Pharmaceutical Salts. J. Pharma. Sci. 1977:66:1.
Fukuda, Yakugaku Zasshi 1952;72:1472.
Chem. Abstr., 1953:8706.
Bennett G.A., et al., Eur. J. Med. Chem., 1989;24:579.
Bagli J. F., Ferdinandi E. Can J. Chem., 1975;53:2598.

(Continued)

*Primary Examiner*—Johann Richter
*Assistant Examiner*—Chukwuma Nwaonicha
(74) *Attorney, Agent, or Firm*—Michelle A. Sherwood; Charles W. Ashbrook

(57) ABSTRACT

The present invention relates to sulfones that are useful in the treatment of chemokine-mediated disorders. In certain embodiments, the present invention concerns the compounds that are MCP-1 receptor antagonists.

15 Claims, No Drawings

OTHER PUBLICATIONS

Huang, De Ren et al., J. Exp. Med, vol. 193, No. 6, Mar. 19, 2001 pp. 713-725.
Izikson, Leonid et al., J. Exp. Med, vol. 192, No. 7, Oct. 2, 2000 pp. 1075-1080.
Yuan, Guo-Hua et al., Arthritis & Rheumatism, vol. 44, No. 5, May 2001, pp. 1056-1070.
PCT Search Report PCT/IB/03186.
Sacca R et al., "Mediators of inflammation" Current Opinion In Immunology, Currrent Biology, Vo.1. 9, No. 6, Dec. 1997 pp. 851-857, XP004331462.
Bright C et al., "Identification Of A Non Peptidic Rantes Antagonist" Bioorganic & Medicinal Chemistry Letters, vol. 8, No. 7, Apr. 7, 1998 pp. 771-774, XP004136963.

* cited by examiner

MCP-1 RECEPTOR ANTAGONISTS AND METHODS OF USE THEREOF

This application claims the benefit of priority of copending U.S. Application No. 60/402,409 (fully incorporated herein by reference), filed Aug. 9, 2002.

BACKGROUND OF THE INVENTION

Migration of leukocytes from blood vessels into diseased tissues is important to the initiation of normal disease-fighting inflammatory responses. But this process, known as leukocyte recruitment, is also involved in the onset and progression of debilitating and life-threatening inflammatory and autoimmune diseases. The pathology of these diseases results from the attack of the body's immune system defenses on normal tissues. Thus, blocking leukocyte recruitment to target tissues in inflammatory and autoimmune diseases would be a highly effective therapeutic intervention. The leukocyte cell classes that participate in cellular immune responses include lymphocytes, monocytes, neutrophils, eosinophils, and basophils. In many cases, lymphocytes are the leukocyte class that initiates, coordinates, and maintains chronic inflammatory responses, and thus are generally the most important class of cells to block from entering inflammatory sites. Lymphocytes attract monocytes to the site, which, collectively with lymphocytes, are responsible for much of the actual tissue damage that occurs in inflammatory disease. Infiltration of lymphocytes and/or monocytes is responsible for a wide range of chronic, autoimmune diseases, and also organ transplant rejection. These diseases include, but are not limited to, rheumatoid arthritis, atherosclerosis, psoriasis, chronic contact dermatitis, inflammatory bowel disease, multiple sclerosis, sarcoidosis, idiopathic pulmonary fibrosis, dermatomyositis, skin pemphigoid and related diseases (e.g., pemphigus vulgaris, p. foliaceous, p. erythematosis), glomerulonephritides, vasculitides, hepatitis, diabetes, allograft rejection, and graft-versus-host disease.

This migration process, by which leukocytes leave the bloodstream and accumulate at inflammatory sites, and initiate disease, takes place in at least three distinct steps which have been described as (1) rolling, (2) activation/firm adhesion, and (3) transendothelial migration (Springer T. A., Nature 1990; 346:425–433; Lawrence and Springer, Cell 1991; 65:859–873; Butcher E. C., Cell, 1991; 67:1033–1036). The second step is mediated at a molecular level by chemoattractant receptors. Chemoattractant receptors on the surface of leukocytes bind chemoattractant cytokines secreted by cells at the site of damage or infection. Receptor binding activates leukocytes, increases the adhesiveness of the adhesion molecules that mediate transendothelial migration, and promotes directed migration of the cells toward the source of the chemoattractant cytokine.

A recent discovery is the existence of a large family (>20 members) of structurally homologous chemoattractant cytokines, approximately 8 to 10 kDa in size. These molecules share the ability to stimulate directed cell migration (chemotaxis) and have been collectively called "chemokines," a contraction of chemotactic cytokines. Each chemokine contains four cysteine residues (C) and two internal disulfide bonds. Chemokines can be grouped into two subfamilies, based on whether the two amino terminal cysteine residues are immediately adjacent (C—C family) or separated by one amino acid (C—X—C family). These differences correlate with the organization of the two subfamilies into separate gene clusters. Within each gene cluster, the chemokines typically show sequence similarities between 25% to 60%.

The chemokines of the C—X—C subfamily, such as interleukin-8 (IL-8), are produced by a wide range of cell types and act predominantly on neutrophils as mediators of acute inflammation. Chemokines of the C—C subfamily are also produced by a wide variety of cell types. These molecules act predominantly on subsets of mononuclear inflammatory cells. Currently there are at least six C—C chemokines with known chemotactic activity for human monocytes and/or T cells, including MCP-1, MCP-2, MCP-3, MIP-1α, MIP-1β, and RANTES (regulated on activation, normal T cell expressed and secreted). This suggests there may be a high degree of redundancy in chemoattractant pathways. In addition, most C—C chemokines are chemotactic for more than one cell type. For example, RANTES acts on memory $CD4^+$ T cells, eosinophils, and monocytes. Monocyte chemoattractant protein-1 (MCP-1), another C—C chemokine, acts on monocytes, activated "memory" T cells and on basophils. MCP-1 is also a potent secretogogue of inflammatory mediators for monocytes and basophils.

Five C—C chemokine receptors have recently been characterized (CKR1–5 or CCR1–CCR5), and all of these belong to the seven transmembrane spanning G protein-coupled receptor family. Each of these receptors mediates the binding and signaling of more than one chemokine. For example, the CCR1 receptor binds both MIP-1α and RANTES. There are two receptors which bind MCP-1, namely CCR2 (with alternately spliced forms, 2A and 2B), and CCR4. CCR2 is also known to mediate binding and signaling of MCP-3. The CCR4 receptor binds and signals, in addition to MCP-1, with RANTES and MIP-1α. Which of these is responsible for the MCP-1 mediated recruitment of monocytes and T cells is not known.

In agreement with the observation that lymphocyte migrate into inflammatory sites is usually accompanied by migration of monocytes, MCP-1 is expressed at sites of antigen challenge and autoimmune disease. However, analyses of human inflammatory lesions with antibodies to other chemokines show RANTES, MIP-1α, MIP-1β, and MCP-3 to be present as well. Injection of MCP-1 into skin sites in mice provokes only a mild monocytic infiltrate or no infiltrate at all (Ernst C. A. et al., J. Immunol., 1994; 152: 3541–3544). Whether these results reflect redundant and complex recruitment pathways has not been resolved. MCP-1 and MCP-3 may play a role in allergic hypersensitivity disease. This is suggested by the observation that MCP-1 lacking the amino terminal glutamic acid loses the ability to stimulate basophil mediator release and acquires activity as an eosinophil chemoattractant.

Chemokines of both subfamilies may bind to heparin sulfate proteoglycans on the endothelial cell surface, and may function principally to stimulate haptotaxis of leukocytes that attach to cytokine-activated endothelium through induced adhesion molecules. Additionally, MCP-1 has been reported to selectively activate the β1 integrin family of leukocyte adhesion molecules, suggesting a role in leukocyte interactions with the extracellular matrix. Hence, MCP-1 may not only trigger the initial arrest and adhesion of monocytes and T cells, but may also act to guide their migration in extravascular space.

Chemoattractants appear to be required for transendothelial migration in vitro and in vivo and can induce all steps required for transmigration in vivo. Injection of neutrophil chemoattractants into skin or muscle leads to robust migration of neutrophils from the vasculature and accumulation at the injection site. Pretreatment of neutrophils with pertussis toxin inhibits migration into inflammatory sites (Spangrude et al. *J. Immunol.* 1985; 135(6):4135–4143; Nourshargh and Williams *J. Immunol.* 1990; 145(8):2633–2638). Moreover, administration of a neutralizing monoclonal antibody against IL-8 markedly inhibits neutrophil migration in inflammation (Sekido et al., *Nature* 1993; 365(6447):654–657).

Chemoattractants impart directionality to leukocyte migration. By contrast with intradermal injection, intravascular injection of IL-8 does not lead to migration (Hechtman et al. *J. Immunol.* 1991; 147(3):883–892). Cytokine-stimulated endothelial monolayers grown on filters secrete IL-8 into the underlying collagen layer. Neutrophils added to the apical compartment migrate into the basilar compartment, but not when the IL-8 gradient is disrupted by addition of IL-8 to the apical compartment (Huber et al., *Science* 1991; 254(5028):99–102).

The endothelium may present chemoattractants to leukocytes in a functionally relevant way, as well as providing a permeability barrier that stabilizes the chemoattractant gradient. Since leukocytes, responding to specific antigen or inflammatory signals in tissue, may signal migration of further leukocytes into the site, a chemoattractant was sought in material secreted by mitogen-stimulated mononuclear cells (Carr et al. *Proc. Natl. Acad. Sci. USA.* 1994; 91(9):3652–3656). Purification to homogeneity guided by a transendothelial lymphocyte chemotaxis assay revealed that MCP-1, previously thought to be solely a monocyte chemoattractant, is a major lymphocyte chemoattractant. An activated subset of memory lymphocytes respond to MCP-1. In the same assay, lymphocytes respond to RANTES and MIP-1α but less so than to MCP-1 (C—C chemokines) and not at all to IL-8 or IP-10 (C—X—C chemokines). This physiologically relevant assay suggests that C—C chemokines tend to attract both monocytes and lymphocytes. In agreement with the observation that lymphocyte migration into inflammatory sites is accompanied by migration of monocytes, MCP-1 is abundantly expressed at sites of antigen challenge and autoimmune disease and, together with other chemokines, is an excellent candidate to provide the Step B signal required to activate integrin adhesiveness and migration of lymphocytes in vivo (Springer, *Cell* 1194; 76:301–314).

SUMMARY OF THE INVENTION

Accordingly, the present invention provides, methods and compounds for the treatment of chemokine associated disorders, such as chronic or acute inflammatory disease, atherosclerosis, restenosis, rheumatoid arthritis, chronic or acute immune disorders, and transplant rejection in subjects in need thereof comprising administering to such patient an effective amount of a compound of the invention. In a first embodiment, compounds of the invention are defined by Formula I or II, and pharmaceutically acceptable salts of Formulas I or II:

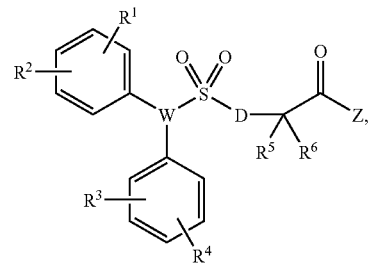

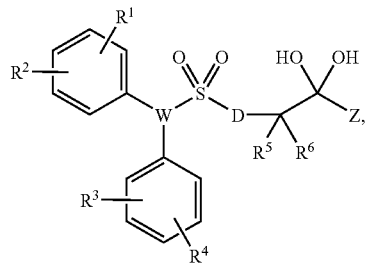

wherein: D is $(CH_2)_n$, where n is 0 or 1; $R^1$, $R^2$, $R^3$, and $R^4$ are each independently selected from the group consisting of: H, $C_1$–$C_6$ alkyl, $C_3$–$C_6$ cycloalkyl, $C_3$–$C_6$ heterocycloalkyl, halogen, and $CF_3$; W is N, CH, or CF; $R^5$ and $R^6$ are each independently H or F; Z is selected from the group consisting of: $C_1$–$C_6$ alkyl, $CH_2Br$, $CH_2Cl$, $CF_3$, $CH_2F$, $CHF_2$, $CH_2R^7$, $CFR^7R^8$, $CF_2R^7$, $CH_2OR^7$, $CHFOR^7$, $CF_2OR^7$, $C(O)NR^7R^8$, $CO_2R^7$,

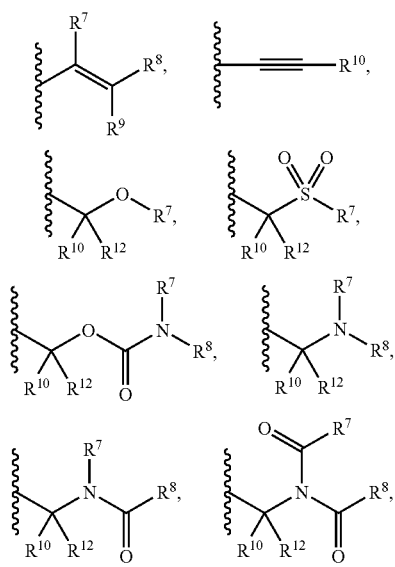

phenyl, $C_6$–$C_{12}$aryl, and $C_5$–$C_{12}$heteroaryl; $R^7$, $R^8$, and $R^9$, are independently selected from the group consisting of H, $C_1$–$C_6$alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_1$–$C_6$alkyl-; and $R^{10}$ and $R^{12}$ are independently selected from the group consisting of F, H, $C_1$–$C_6$ alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroary-$C_1$–$C_6$alkyl-, wherein 2-(diphenyl-methanesulfonyl)-1-pyridin-2-yl-ethanone is not included. In certain embodiments, D is 0; W is CH; and $R^1$, $R^2$, $R^3$, and $R^4$ are each independently selected from the group consisting of: H, $C_1$–$C_6$alkyl, and halogen. In other embodiments, Z may be selected from the group consisting of: $CF_3$, $CH_2Cl$, $CH_2F$, $CHF_2$, $CH_2R^7$, $CFR^7R^8$, $CF_2R^7$, $CH_2OR^7$, $CHFOR^7$, and $CF_2OR^7$. In still other embodiments, $R^{10}$ and $R^{12}$ are H or F; and Z is selected from the group consisting of:

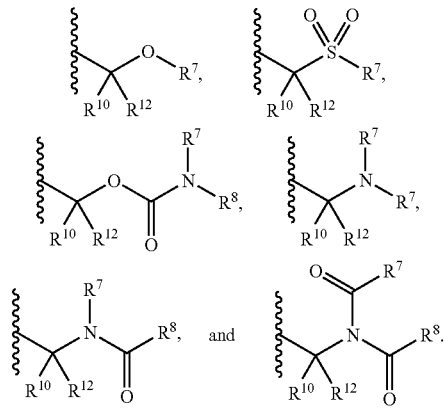

Compounds of the present invention include, but are not limited to:

1-[Bis-(4-chloro-phenyl)-methanesulfonyl]-propan-2-one;
1-[Bis-(4-chloro-phenyl)-methanesulfonyl]-butan-2-one;
1-[Bis-(4-chloro-phenyl)-methanesulfonyl]-3-bromo-propan-2-one;
3-[Bis-(4-chloro-phenyl)-methanesulfonyl]-1,1,1-trifluoro-propan-2-one;
2-[Bis-(4-chloro-phenyl)-methanesulfonyl]-1-furan-2-yl-ethanone;
1-[Bis-(4-chloro-phenyl)-methanesulfonyl]-pent-3-yn-2-one;
3-[Bis-(4-chloro-phenyl)-methanesulfonyl]-1-fluoro-propan-2-one;
3-[Bis-(4-chloro-phenyl)-methanesulfonyl]-1,1-difluoro-propan-2-one;
1-[Bis-(4-chloro-phenyl)-methanesulfonyl]-3-phenyl-propan-2-one;
1-[Bis-(4-chloro-phenyl)-methanesulfonyl]-3-phenoxy-propan-2-one;
1-[Bis-(4-chloro-phenyl)-methanesulfonyl]-3-(4-methoxy-phenoxy)-propan-2-one;
1-[Bis-(4-chloro-phenyl)-methanesulfonyl]-3-(4-chloro-phenoxy)-propan-2-one;
1-[Bis-(4-chloro-phenyl)-methanesulfonyl]-3-(2,4-difluoro-phenoxy)-propan-2-one;
1-[Bis-(4-chloro-phenyl)-methanesulfonyl]-3-methoxy-propan-2-one;
1-[Bis-(4-chloro-phenyl)-methanesulfonyl]-pent-3-ene-2-one;
2-[Bis-(4-chloro-phenyl)-methanesulfonyl]-1-(1-methyl-1H-imidazol-2-yl)-ethanone;
5-(2-[Bis-(4-chloro-phenyl)-methanesulfonyl]-acetyl)-thiophene-2-carboxylic acid dimethylamide;
2-[Bis-(4-chloro-phenyl)-methanesulfonyl]-1-thiophen-2-yl-ethanone;
1-[Bis-(4-chloro-phenyl)-methanesulfonyl]-3,3-dimethyl-butan-2-one;
1-[Bis-(4-chloro-phenyl)-methanesulfonyl]-4-phenyl-butan-2-one;
4-[Bis-(4-chloro-phenyl)-methanesulfonyl]-3-oxo-butyric acid methyl ester;
4-[Bis-(4-chloro-phenyl)-methanesulfonyl]-N-(2-chloro-phenyl)-3-oxo-butyramide;
4-[Bis-(4-chloro-phenyl)-methanesulfonyl]-butan-2-one;
Acetic acid 3-[bis-(4-chloro-phenyl)-methanesulfonyl]-2-oxo-propyl ester;
1-[Bis-(4-chloro-phenyl)-methanesulfonyl]-4,4,4-trifluoro-butan-2-one;
1-[Bis-(4-chloro-phenyl)-methanesulfonyl]-3-phenyl-methanesulfonyl-propan-2-one;
3-[Bis(4-fluorophenyl)methanesulfonyl]-1,1,1-trifluoropropane-2,2-diol;
3-[Bis(4-trifluoromethyl-phenyl)methanesulfonyl]-1,1,1-trifluoropropane-2,2-diol;
3-[(4-Chlorophenyl)-(3,4-dichlorophenyl)methanesulfonyl]-1,1,1-trifluoropropane-2,2-diol;
3-[Biphen-4-yl-(4-chlorophenyl)methanesulfonyl]-1,1,1-trifluoropropane-2,2-diol;
3-[(4-Chlorophenyl)-(4-isobutylphenyl)methanesulfonyl]-1,1,1-trifluoropropane-2,2-diol;
3[(4-Chlorophenyl)-(4-isobutylphenyl)methanesulfonyl]-1,1,1-trifluoropropan-2-one;
1-[Bis-(4-chloro-phenyl)-methanesulfonyl]-3-(4-fluoro-phenyl)-propan-2-one;
2-[Bis-(4-chloro-phenyl)-methylsulfonyl]-1-pyridin-2-yl-ethanone;
1-[Bis-(4-chloro-phenyl)-methanesulfonyl]-1-fluoro-propan-2-one;
3-[Bis-(4-chloro-phenyl)-methanesulfonyl]-3,3-difluoro-butan-2-one;
1-[Bis-(4-chloro-phenyl)-methanesulfonyl]-3-fluoro-butan-2-one;
(R)-1-[Bis-(4-chloro-phenyl)-methanesulfonyl]-3,3-difluoro-4-phenyl-pentan-2-one;
(S)-1-[Bis-(4-chloro-phenyl)-methanesulfonyl]-3,3-difluoro-4-phenyl-pentan-2-one;
1-[Bis-(4-chloro-phenyl)-methanesulfonyl]-4-(3,4-dimethoxy-phenyl)-3,3-difluoro-butan-2-one;
3-[Bis-(4-chloro-phenyl)-methanesulfonyl]-N,N-dimethyl-2-oxo-propionamide;
1-[Bis-(4-chloro-phenyl)-methanesulfonyl]-3-hydroxy-propan-2-one;
1-[Bis-(4-chloro-phenyl)-methanesulfonyl]-3-methoxy-propan-2-one;
3-[Bis-(4-chloro-phenyl)-methanesulfonyl]-1,1-difluoro-1-methoxy-propan-2-one;
1-[Bis-(4-chloro-phenyl)-methanesulfonyl]-3,3-difluoro-butan-2-one;
1-[Bis-(4-chloro-phenyl)-methanesulfonyl]-4,4,4-trichloro-3,3-difluoro-butan-2-one;
1-[Bis-(4-chloro-phenyl)-methanesulfonyl]-3,3-difluoro-butan-2-one;
1-[Bis-(4-chloro-phenyl)-methanesulfonyl]-3,3-difluoro-4-methyl-pentan-2-one;
6-[Bis-(4-chloro-phenyl)-methanesulfonyl]-4,4-difluoro-5-oxo-hexanoic acid methyl ester;
3-[1-(4-Chloro-phenyl)-1-(3,4-dichloro-phenyl)-methanesulfonyl]-1,1,1-trifluoro-propan-2-one;
3-[Bis-(3,4-dichloro-phenyl)-methanesulfonyl]-1,1,1-trifluoro-propan-2-one;
1-Benzyloxy-3-[bis-(4-chloro-phenyl)-methanesulfonyl]-propan-2-one;

1-[1-(4-Chloro-phenyl)-1-(3,4-dichloro-phenyl)-methane-sulfonyl]-4-(3,4-dimethoxy-phenyl)-3,3-difluoro-butan-2-one;
1-[Bis-(3,4-dichloro-phenyl)-methanesulfonyl]-4-(3,4-dimethoxy-phenyl)-3,3-difluoro-butan-2-one;
3,3,3-Trifluoro-2-oxo-propane-1-sulfonic acid bis-(4-chloro-phenyl)-amide;
4-(3,4-Dimethoxy-phenyl)-3,3-difluoro-2-oxo-butane-1-sulfonic acid bis-(4-chloro-phenyl)-amide;
4-(3,4-Dimethoxy-phenyl)-3,3-difluoro-2-oxo-butane-1-sulfonic acid (4-chloro-phenyl)-(3,4-dichloro-phenyl)-amide;
2-[Bis-(4-chloro-phenyl)-methanesulfonyl]-1-(5-methyl-furan-2-yl)-ethanone;
2-[Bis-(4-chloro-phenyl)-methanesulfonyl]-1-(5-nitro-furan-2-yl)-ethanone;
2-[Bis-(4-chloro-phenyl)-methanesulfonyl]-1-[5-(2,4-difluoro-phenyl)-furan-2-yl]-ethanone;
2-[Bis-(4-chloro-phenyl)-methanesulfonyl]-1-oxazol-2-yl-ethanone;
2-[Bis-(4-chloro-phenyl)-methanesulfonyl]-1-(5-phenyl-isoxazol-3-yl)-ethanone;
2-[Bis-(4-chloro-phenyl)-methanesulfonyl]-1-[5-(3,4-dichloro-phenyl)-isoxazol-3-yl]-ethanone;
2-[Bis-(4-chloro-phenyl)-methanesulfonyl]-1-[5-(2,4-dichloro-phenyl)-isoxazol-3-yl]-ethanone;
2-[Bis-(4-chloro-phenyl)-methanesulfonyl]-1-[3-(4-chloro-phenyl)-isoxazol-5-yl]-ethanone;
2-[Bis-(4-chloro-phenyl)-methanesulfonyl]-1-[3-(3-trifluoromethyl-phenyl)-isoxazol-5-yl]-ethanone;
2-[Bis-(4-chloro-phenyl)-methanesulfonyl]-1-[3-(2,4-dichloro-phenyl)-isoxazol-5-yl]-ethanone;
2-[Bis-(4-chloro-phenyl)-methanesulfonyl]-1-[3-(3-chloro-5-trifluoromethyl-pyridin-2-yl)-isoxazol-5-yl]-ethanone;
2-[Bis-(4-chloro-phenyl)-methanesulfonyl]-1-(5-nitro-thiophen-2-yl)-ethanone;
5-{2-[Bis-(4-chloro-phenyl)-methanesulfonyl]-ethanoyl}-thiophene-2-carboxylic acid dimethylamide;
5-{2-[Bis-(4-chloro-phenyl)-methanesulfonyl]-ethanoyl}-thiophene-2-carbonitrile;
2-[Bis-(4-chloro-phenyl)-methanesulfonyl]-1-thiazol-2-yl-ethanone;
2-[Bis-(4-chloro-phenyl)-methanesulfonyl]-1-(4,5-dihydro-thiazol-2-yl)-ethanone;
2-[Bis-(4-chloro-phenyl)-methanesulfonyl]-1-(1-oxo-4,5-dihydro-1H-1λ4-thiazol-2-yl-ethanone;
2-[Bis-(4-chloro-phenyl)-methanesulfonyl]-1-(dioxo-4,5-dihydro-1H-1λ6-thiazol-2-yl-ethanone;
2-[Bis-(4-chloro-phenyl)-methanesulfonyl]-1-(2-phenyl-thiazol-4-yl]-ethanone;
2-[Bis-(4-chloro-phenyl)-methanesulfonyl]-1-[2-(4-trifluoromethyl-phenyl)-thiazol-4-yl]-ethanone;
2-[Bis-(4-chloro-phenyl)-methanesulfonyl]-1-pyridin-2-yl-ethanone;
2-[Bis-(4-chloro-phenyl)-methanesulfonyl]-1-pyridin-4-yl-ethanone;
2-[Bis-(4-chloro-phenyl)-methanesulfonyl]-1-pyrimidin-2-yl-ethanone;
1-Benzofuran-2-yl-2-[bis-(4-chloro-phenyl)-methanesulfonyl]-ethanone;
2-[Bis-(4-chloro-phenyl)-methanesulfonyl]-1-[5-nitro-benzofuran-2-yl)-ethanone;
2-[Bis-(4-chloro-phenyl)-methanesulfonyl]-1-(7-hydroxy-benzofuran-2-yl)-ethanone;
1-[Bis-(4-chloro-phenyl)-methanesulfonyl]-3-(4-trifluoromethyl-phenoxy)-propan-2-one;
1-[Bis-(4-chloro-phenyl)-methanesulfonyl]-3-(4-methane-sulfonyl-phenoxy)-propan-2-one;
Ethyl-carbamic acid 3-[bis-(4-chloro-phenyl)-methane-sulfonyl]-2-oxo-propyl ester;
N-{3-[Bis-(4-chloro-phenyl)-methanesulfonyl]-2-oxo-propyl}-acetamide;
N-{3-[Bis-(4-chloro-phenyl)-methanesulfonyl]-2-oxo-propyl}-benzamide;
Benzyl-carbamic acid 3-[bis-(4-chloro-phenyl)-methane-sulfonyl]-2-oxo-propyl ester;
1-[Bis-(4-chloro-phenyl)-methanesulfonyl]-3-methane-sulfonyl-propan-2-one;
1-benzenesulfonyl-3-[bis-(4-chloro-phenyl)-methanesulfonyl]-propan-2-one;
1-[Bis-(4-chloro-phenyl)-methanesulfonyl]-3-phenyl-propan-2-one;
1-[Bis-(4-chloro-phenyl)-methanesulfonyl]-3-phenoxy-propan-2-one;
and pharmaceutically acceptable salts of the foregoing compounds.

In another aspect, the present invention provides for methods of treating a chemokine associated disorder in a subject comprising administering to the subject an effective amount of a compound of Formula I or II, or a pharmaceutically acceptable salt of I or II:

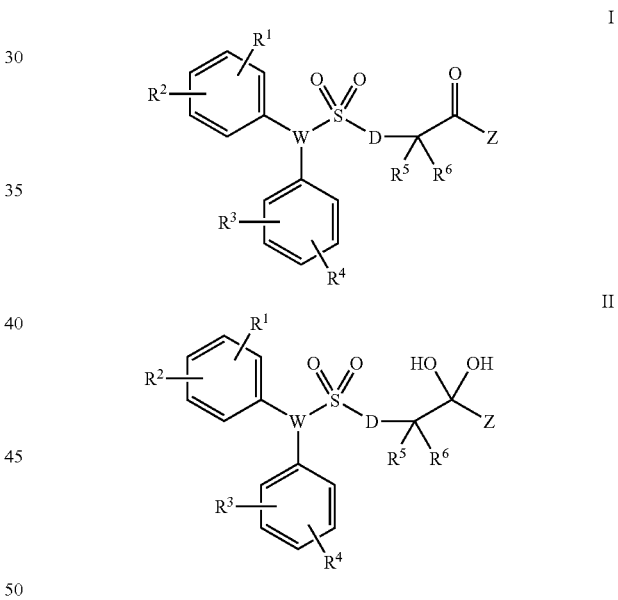

wherein: D is $(CH_2)_n$, where n is 0 or 1; $R^1$, $R^2$, $R^3$, and $R^4$ are each independently selected from the group consisting of: H, $C_1$–$C_6$alkyl, $C_3$–$C_6$cycloalkyl, $C_3$–$C_6$ heterocycloalkyl, halogen, and $CF_3$; W is N, CH, or CF; $R^5$ and $R^6$ are each independently H or F; Z is selected from the group consisting of: $C_1$–$C_6$alkyl, $CH_2Br$, $CH_2Cl$, $CF_3$, $CH_2F$, $CHF_2$, $CH_2R^7$, $CFR^7R^8$, $CF_2R^7$, $CH_2OR^7$, $CHFOR^7$, $CF_2OR^7$, $C(O)NR^7R^8$, $CO_2R^7$,

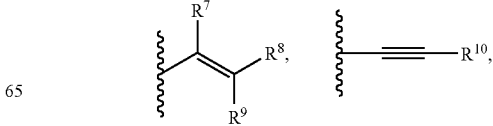

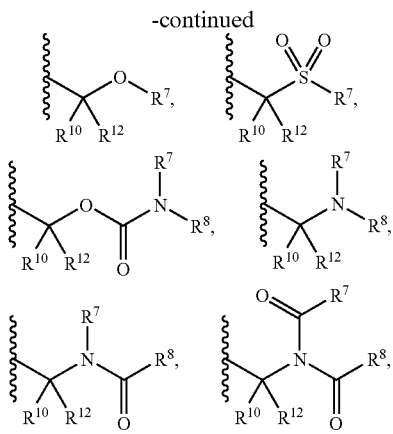

phenyl, $C_6$–$C_{12}$aryl, and $C_5$–$C_{12}$heteroaryl; $R^7$, $R^8$, and $R^9$, are independently selected from the group consisting of H, $C_1$–$C_6$ alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_{1-6}$alkyl-; and $R^{10}$ and $R^{12}$ are independently selected from the group consisting of F, H, $C_1$–$C_6$alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_1$–$C_6$alkyl-, wherein 2-(diphenyl-methanesulfonyl)-1-pyridin-2-yl-ethanone is not included, for the treatment of a chemokine associated disorders. In certain embodiments, the chemokine-associated disorder is rheumatoid arthritis. In other embodiments, the chemokine-associated disorder is atherosclerosis.

In another embodiment, the present invention includes the uses of compounds of Formula I or Formula II in the manufacture of a medicament for the treatment of a chemokine-associated disorder.

In yet another embodiment, the present invention pertains to a composition comprising a compound of Formula I or II, and a pharmaceutically acceptable carrier, excipient, or diluent.

DETAILED DESCRIPTION OF THE INVENTION

The invention pertains to CCR2 antagonists (or MCP-1 Receptor antagonists) which are useful in the treatment of a chemokine-associated disorder. Thus, these compounds are useful as agents for the treatment of inflammatory diseases, especially those associated with lymphocyte and/or monocyte accumulation, such as arthritis, atherosclerosis, and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

1. Definitions

Before further description of the invention, certain terms employed in the specification, examples and appended claims are, for convenience, collected here.

The term "alkyl group" or "alkyl" includes straight and branched carbon chain radicals. For example, a "$C_{1-6}$ alkyl" is an alkyl group having from 1 to 6 carbon atoms. Examples of straight-chain alkyl groups include, but are not limited to, methyl, ethyl, n-propyl, n-butyl, n-pentyl, n-hexyl, n-heptyl, n-octyl, n-nonyl, n-decyl, etc. Examples of branched-chain alkyl groups include, but are not limited to, isopropyl, tert-butyl, isobutyl, etc.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, $C_1$–$C_6$-alkenyl, $C_1$–$C_6$-alkynyl, halogen, I, Br, Cl, F, hydroxyl, $C_1$–$C_6$-alkylcarbonyloxy, $C_6$–$C_{12}$-arylcarbonyloxy, $C_1$–$C_6$-alkoxycarbonyloxy, $C_6$–$C_{12}$-aryloxycarbonyloxy, COOH, $C_1$–$C_6$-alkylcarbonyl, $C_6$–$C_{12}$-arylcarbonyl, $C_1$–$C_6$-alkoxycarbonyl, aminocarbonyl, $C_1$–$C_6$-alkylaminocarbonyl, (di-$C_1$–$C_6$-alkyl)aminocarbonyl, $C_1$–$C_6$-alkylthiocarbonyl, $C_1$–$C_6$-alkoxy, cyano, amino (including $C_1$–$C_6$-alkyl amino, di-$C_1$–$C_6$-alkylamino, $C_6$–$C_{12}$-arylamino, di-$C_6$–$C_{12}$-arylamino, and $C_1$–$C_6$-alkyl-$C_6$–$C_{12}$-arylamino), acylamino (including $C_1$–$C_6$-alkylcarbonylamino and $C_6$–$C_{12}$-arylcarbonylamino), sulfhydryl, $C_1$–$C_6$-alkylthio, $C_6$–$C_{12}$-aryl, $C_6$–$C_{12}$-arylthio, $C_1$–$C_6$-alkylsulfinyl, nitro, trifluoromethyl, $C_5$–$C_{12}$-heteroaryl, or $C_1$–$C_6$-alkyl-$C_6$–$C_{12}$-aryl. Typical substituted alkyl groups thus are aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl.

"Alkoxy" refers to the alkyl groups mentioned above bound through oxygen, examples of which include methoxy, ethoxy, isopropoxy, tert-butoxy, and the like. In addition, alkoxy refers to polyethers such as O—$(CH_2)_2$—O—$CH_3$, and the like. The term "alkoxy" is intended to include both substituted and unsubstituted alkoxy groups. Alkoxy groups can be substituted with groups such as those set out above for alkyl. Typical substituted alkoxy groups include aminomethoxy, trifluoromethoxy, 2-diethylaminoethoxy, 2-ethoxycarbonylethoxy, 3-hydroxypropoxy, and the like.

"Alkanoyl" groups are alkyl linked through a carbonyl, e.g., $C_1$–$C_6$alkyl-C(O)—. Such groups include formyl, acetyl, propionyl, butyryl, and isobutyryl. The term "alkanoyl" is intended to include both substituted and unsubstituted alkanoyl groups. Alkanoyl groups can be substituted with groups such as those set out above for alkyl.

"Acyl" means an alkyl or aryl (Ar) group bonded through a carbonyl group, i.e., R—C(O)—. For example, acyl includes a $C_1$–$C_6$ alkanoyl, including substituted alkanoyl. The term "acyl" is intended to include both substituted and unsubstituted acyl groups. Acyl groups can be substituted with groups such as those set out above for alkyl.

"Halo" includes fluoro, chloro, bromo, and iodo.

"Alkenyl" means straight and branched hydrocarbon radicals having two or more carbon atoms and comprising at least one double bond and includes ethenyl, 3-buten-1-yl, 2-ethenylbutyl, 3-hexen-1-yl, and the like. The term "alkenyl" is intended to include both substituted and unsubstituted alkenyl groups. A "$C_2$–$C_6$-alkenyl" is an alkenyl group having from from 2 to 6 carbon atoms. Alkenyl groups can be substituted with groups such as those set out above for alkyl.

"Alkynyl" means straight and branched hydrocarbon radicals having two or more carbon atoms and comprising at least one triple bond and includes ethynyl, 3-butyn-1-yl, propynyl, 2-butyn-1-yl, 3-pentyn-1-yl, and the like. The term "alkynyl" is intended to include both substituted and unsubstituted alkynyl groups. Alkynyl groups can be substituted with groups such as those set out above for alkyl.

Examples of substituted alkynyl groups include 2-methoxyethynyl, 2-ethylsulfanyethynyl, 3-diethylamino-3-butynyl, 4-chloro-3-butynyl, 4-cyclobutyl-4-hexenyl, and the like. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

"Carbocycle" or "Cycloalkyl" means a mono or bicyclic carbocyclic ring functional group including, but not limited to, cyclopropyl, cyclobutyl, cyclopentyl, cyclohexyl, cycloheptyl, cyclooctyl, cyclononyl, bicyclo[2.2.1]heptanyl, bicyclo[3.2.1]octanyl and bicyclo[5.2.0]nonanyl; wherein the cycloalkyl group may optionally contain 1 or 2 double bonds (i.e., a cycloalkylene) including, but not limited to, cyclopentenyl, cyclohexenyl and cycloheptenyl. The term "cycloalkyl" is intended to include both substituted and unsubstituted cycloalkyl groups. Cycloalkyl groups can be substituted with groups such as those set out above for alkyl. Unless otherwise indicated, the term "($C_3$–$C_6$)cycloalkyl" refers to a cycloalkyl group containing from 3 to 6 carbons.

A "heterocycloalkyl group" or "heterocycloalkyl" is a "cycloalkyl" in which 1 to 3 heteroatoms replace carbons in the ring. The heteroatoms are independently selected from O, S, or N. Embraced within the term "heterocycloalkyl" are 5-membered rings having one double bond in the ring (e.g., 2-pyrrolinyl, 3-pyrrolinyl, etc.) and 6-membered rings having one double bond in the ring (e.g., 2H-pyranyl, 1,2,3,4-tetrahydropyridine, 3,4-dihydro-2H-[1,4]oxazine, etc.).

Unless otherwise indicated, the term "($C_3$–$C_6$)heterocycloalkyl" refers to a cyclic functional groups containing from 3 to 6 carbon atoms and 1 to 3 heteroatoms selected from the group consisting of N, O, and S. The term "heterocycloalkyl" is intended to include both substituted and unsubstituted heterocycloalkyl groups. Heterocycloalkyl groups can be substituted with groups such as those set out above for alkyl. Examples of heterocycloalkyls include, but are not limited to, 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Unless otherwise indicated, the foregoing heterocycloalkyls can be C-attached or N-attached where such is possible. For example, piperidinyl can be piperidin-1-yl (N-attached) or piperidin-4-yl (C-attached).

An aryl group is an aromatic hydrocarbon radical. Furthermore, the term "aryl" includes multicyclic aryl groups, eg, tricyclic, and bicyclic, e.g., naphthyl. Typical aryl groups include phenyl, 3-chlorophenyl, 2,6-dibromophenyl, 2,4,6-tribromophenyl, naphthyl, 4,7-dichloronaphthyl, and the like. Typical substituted aryl groups include 2,6-dichlorophenyl, 3-methoxyphenyl, 4-trifluoromethylphenyl, 3-amino-4-nitrophenyl, 3,5-dihydroxyphenyl, and the like. Unless otherwise indicated, the term "($C_6$–$C_{12}$)aryl". means aromatic functional groups containing from 6 to 12 carbons. The term "aryl" is intended to include both substituted and unsubstituted aryl groups. An aryl or ($C_6$–$C_{12}$)aryl can be optionally substituted on any ring carbon atom by one to four functional groups per ring, wherein the substituents are set out above for alkyl.

An "arylalkyl" moiety is an alkyl substituted with an aryl (e.g., phenylmethyl benzyl).

Phenyl may be unsubstituted or substituted at one or more positions with a substituent such as, but not limited to, those substituents described above for alkyl. The term "aryl" is intended to include both substituted and unsubstituted phenyl groups.

Those aryl groups having heteroatoms in the ring structure are referred to as "aryl heterocycles," "heterocycles," "heteroaryls," or "heteroaromatics." Heteroaryl groups are aromatic hydrocarbon radicals containing from 1 to 4 heteroatoms independently selected from the group consisting of: N, S, or O. Heteroaryls include 5- or 6-membered mono- or 10-, 11-, 12-, 13-membered bicyclic ring structures which may contain one or more heteroatoms such as N, S, or O. Unless otherwise indicated, a $C_{5-12}$-heteroaryl is a mono-, bi-, or tricyclic heteroaryl group containing from 5 to 12 carbons in the ring, wherein from 1 to 4 of which are independently selected from the group consisting of O, S, and N. For example, heteroaryl groups can comprise 1 or 2 heteroatoms in a 5- or 6-membered aromatic ring. A heteroaryl can also include ring systems substituted with one or more —(C=O)— functional groups. Examples of heteroaryls include, but are not limited to, benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furanyl, 2-furanyl, 3-furanyl, furazanyl, furopyridinyl, furyl, imidazolyl, indazolyl, indolinyl, indolizinyl, indolyl, or 2-, 3-, 4-, 5-, 6-, or 7-indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, 3- or 4-pyridazinyl, 2-pyrazinyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, quinazolinyl, quinolinyl, quinoxalinyl, tetrazolyl, thiazolyl, thiadiazolyl, thienyl, 2-thienyl, 3-thienyl, triazinyl and triazolyl. The term "heteroaryl" encompasses unsubstituted and substituted heteroaryls. A substituted heteroaryl can be substituted on any atom(s) capable of forming an additional bond by one or two substituents. Unless otherwise indicated, the foregoing heteroaryls can be C-attached, S-attached, or N-attached where such is possible. For instance, pyrrolyl can be pyrrol-1-yl (N-attached) or pyrrol-3-yl (C-attached). The heteroaryl group can be substituted at a carbon on one or more ring positions with such substituents as described above for alkyl, and CHO, $COR_{22}$, $OR_{22}$, $COOR_{22}$, $C(O)NR_{22}R_{24}$, $(CH_2)_nNR_{22}R_{24}$, $(CH_2)_nOR_{22}$, $SR_{22}$, $SOR_{22}$, $SO_2R_{22}$, $NHSO_2R_{22}$, $NR_{22}R_{24}$, $NHCOR_{22}$, $O(CR_{22}R_{24})_{0-3}CF_3$, $O(R_{22}R_{24})_{0-3}CCl_3$, or $SO_2NR_{22}R_{24}$, $SCF_3$, $SCCl_3$, wherein $R_{22}$ and $R_{24}$ are independently hydrogen, substituted or unsubstituted $C_1$–$C_6$alkyl, substituted or unsubstituted $C_2$–$C_6$alkenyl, substituted or unsubstituted $C_1$–$C_6$alkynyl, substituted or unsubstituted $C_6$–$C_{12}$aryl-$C_1$–$C_6$alkyl.

The term "halogen" includes fluoro, bromo, chloro, and iodo.

The term "heteroatom" includes nitrogen, oxygen, and sulfur.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The term "subject" includes organisms which are capable of having or have a chemokine mediated disorder. Preferred examples include humans and animals, including cows, sheep, pigs, dogs, cats, rats, ferrets, bears, rabbits, etc.

The term "treatment" includes the diminishment or alleviation of at least one symptom associated or caused by the disorder being treated. For example, treatment can include diminishment of several symptoms of a disorder or complete eradication of a disorder.

The language "chemokine associated disorder" includes disorders characterized by the participation of chemokines or association with chemokines. The language also includes disorders characterized by aberrant chemokine expression. Chemokines have a wide variety of functions. They are able to elicit chemotactic migration of distinct cell types, such as monocytes, neutrophils, T lymphocytes, basophils, and fibroblasts. Many chemokines have proinflammatory activity and are involved in multiple steps during an inflammatory reaction. These activities include stimulation of histamine release, lysosomal enzyme and leukotriene release, increased adherence of target immune cells to endolethial cells, enhanced binding of complement proteins, induced expression of granulocyte adhesion molecules and complement receptors, and respiratory burst. In addition to their involvement in inflammation, certain chemokines have been shown to exhibit other activities. Chemokines have been proposed to participate in a number of physiological and disease conditions, including, for example, lymphocyte trafficking, wound healing, hemapoietic regulation and disorders such as asthma, atherosclerosis, restenosis, rheumatoid arthritis, and transplant rejection. In a further embodiment, the chemokine mediated disorder is associated with the chemokine MCP-1, MCP-2, MCP-3, or MCP-4.

The language "chemokine associated disorder characterized by inflammation" includes disorders having inflammation as at least one of its symptoms. Examples of such disorders include anaphylaxis, systemic necrotizing vasculitis, systemic lupus erthyematosus, serum sickness syndromes, psoriasis, arthritis, rheumatoid arthritis, osteoarthritis, inflammatory bowel diseases, Crohn's disease, ulcerative colitis, adult respiratory distress syndrome (ARDS), allergic rhinitis, atopic dermatitis, asthma and other allergic responses, and reperfusion injury occurring after periods of ischemia such as in myocardial infarction or shock. Other chemokine associated disorders include neurological related disorders, immunological related disorders and disorders characterized by unwanted cellular proliferation, e.g., cancer.

The language "neurological related disorders" includes disorders of the nervous system, including, but not limited to those involving the brain, the central and peripheral nervous system, and the interfaces between muscles and the nerves. Some examples of neurological related disorders include Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease. "Neurological related disorders" also includes neurological disorders associated with inflammation, e.g., stroke, traumatic injury to the brain, traumatic injury to the spinal cord, spinal crush, and central and peripheral nervous system trauma.

The language "immunological related disorder" includes both organ-specific and systemic immunological disorders. Some examples of immunological disorders include immune thyroiditis, hyperthyroidism, type 1 diabetes mellitus, insulin related diabetes, Addison's disease, autoimmune oophoritis, autoimmune orchitis, AIDS, autoimmune hemolytic anemia, paroxysmal cold hemoglobinuria, autoimmune thrombocytopenia, autoimmune neutropenia, pernicious anemia, autoimmune coagulopathies, myasthenia gravis, multiple sclerosis, experimental allergic encephalomyelitis, pemphigus and other bullous diseases, rheumatic carditis, Goodpasture's syndrome, postcardiotomy syndrome, systemic lupus erythematosus, arthritis, rheumatoid arthritis, osteoarthritis, keratitis, parotitis, polymositis, dermatomyositis, and scleroderma. In an embodiment, the immunological disorder is AIDS, multiple sclerosis, rheumatoid arthritis, or lupus.

Other chemokine associated disorders include, but are not limited to, idiopathic pulmonary fibrosis, graft rejection, allograft rejection, allergic hypersensitivity disorders, psoriasis, chronic contact dermatitis, sarcoidosis, dermatomyositis, skin pemphigoid, pemphigus vulgaris, p. foliacious, p. erythematosus, glomerulonephritides, vasculitides including necrotizing, cutaneous and hypersensitivity vasculitis; hepatitis, diabetes, systemic lupus erythematosus, myasthenia gravis, dermatitis, eczema, atopic dermatitis, allergic contact dermatitis, urticaria, and reperfusion injury.

The language "effective amount" of the compound is that amount necessary or sufficient to treat or prevent a chemokine associated state, e.g., prevent the various morphological and somatic symptoms of a chemokine associated state. The effective amount can vary depending on such factors as the size and weight of the subject, the type of illness, or the particular compound of the invention. For example, the choice of the compound of the invention can affect what constitutes an "effective amount." One of ordinary skill in the art would be able to study the aforementioned factors and make the determination regarding the effective amount of a compound of the invention without undue experimentation.

The term "antagonist" includes compounds which bind to the CCR-2 such that the binding of a second compound to CCR-2 is modulated. In a further embodiment, the ability of the second compound to interact with CCR-2 is inhibited or decreased.

2. Compounds of the Invention

The invention pertains, at least in part, to compounds having Formula I and II, and pharmaceutically acceptable salts of I and II:

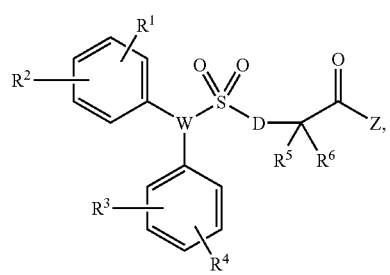

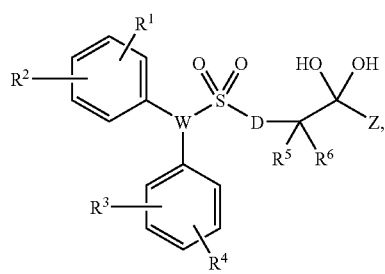

II wherein: D is $(CH_2)_n$, where n is 0 or 1; $R^1$, $R^2$, $R^3$, and $R^4$ are each independently selected from the group consisting of: H, $C_1$–$C_6$alkyl, $C_3$–$C_6$cycloalkyl, $C_3$–$C_6$heterocycloalkyl, halogen, and $CF_3$; W is N, CH, or CF; $R^5$ and $R^6$ are each independently H or F; Z is selected from the group consisting of: $C_1$–$C_6$alkyl, $CH_2Br$, $CH_2Cl$, $CF_3$, $CH_2F$, $CHF_2$, $CH_2R^7$, $CFR^7R^8$, $CF_2R^7$, $CH_2R^7$, $CH_2OR^7$, $CHFOR^7$, $CF_2OR^7$, $C(O)NR^7R^8$, $CO_2R^7$,

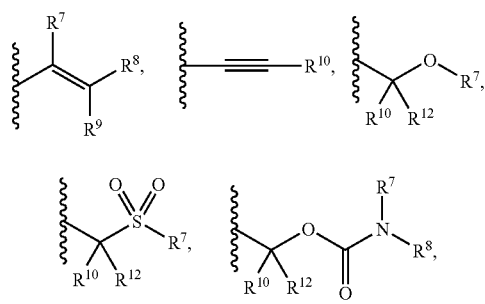

phenyl, $C_6$–$C_{12}$aryl, and $C_5$–$C_{12}$heteroaryl; $R^7$, $R^8$, and $R^9$, are independently selected from the group consisting of H, $C_1$–$C_6$alkyl, $CF_3$, $CCl_3$, aryl, aryl-$C_1$–$C_6$alkyl-, $C_5$–$C_{12}$heteroaryl, and $C_5$–$C_{12}$heteroaryl-$C_1$–$C_6$alkyl-; and $R^{10}$ and $R^{12}$ are independently selected from the group consisting of F, H, $C_1$–$C_6$alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_1$–$C_6$alkyl-, wherein 2-(diphenyl-methanesulfonyl)-1-pyridin-2-yl-ethanone is not included.

Examples of Z for compounds of Formula I and II include, without limitation, $C_1$–$C_6$alkyl, $CH_2Br$, $CH_2Cl$, $CF_3$, $CH_2F$, $CHF_2$, $CH_2R^7$, $CFR^7R^8$, $CF_2R^7$, $CH_2R^7$, $CHFOR^7$, $CF_2OR^7$, $CF_2OR^7$, $C(O)NR^7R^8$, $CO_2R^7$,

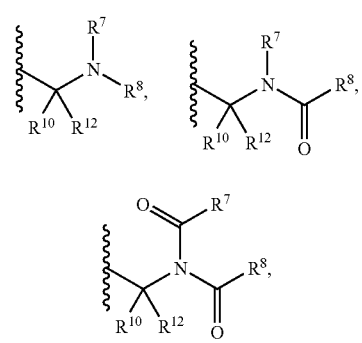

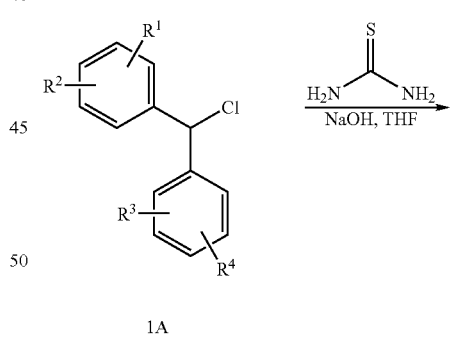

phenyl, $C_6$–$C_{12}$aryl, and $C_5$–$C_{12}$heteroaryl.

General Synthesis:

Compounds of Formula I and II can be prepared by applying synthetic methodology known in the art and synthetic methodology outlined in Schemes 1 to 20 set forth below.

Scheme 1

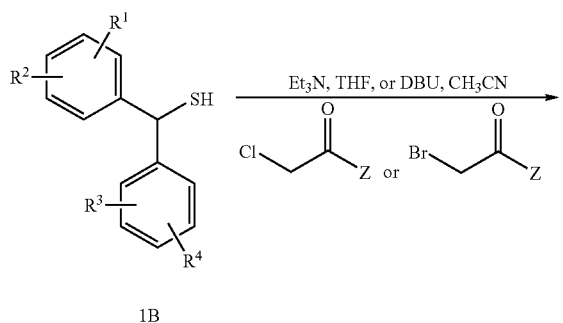

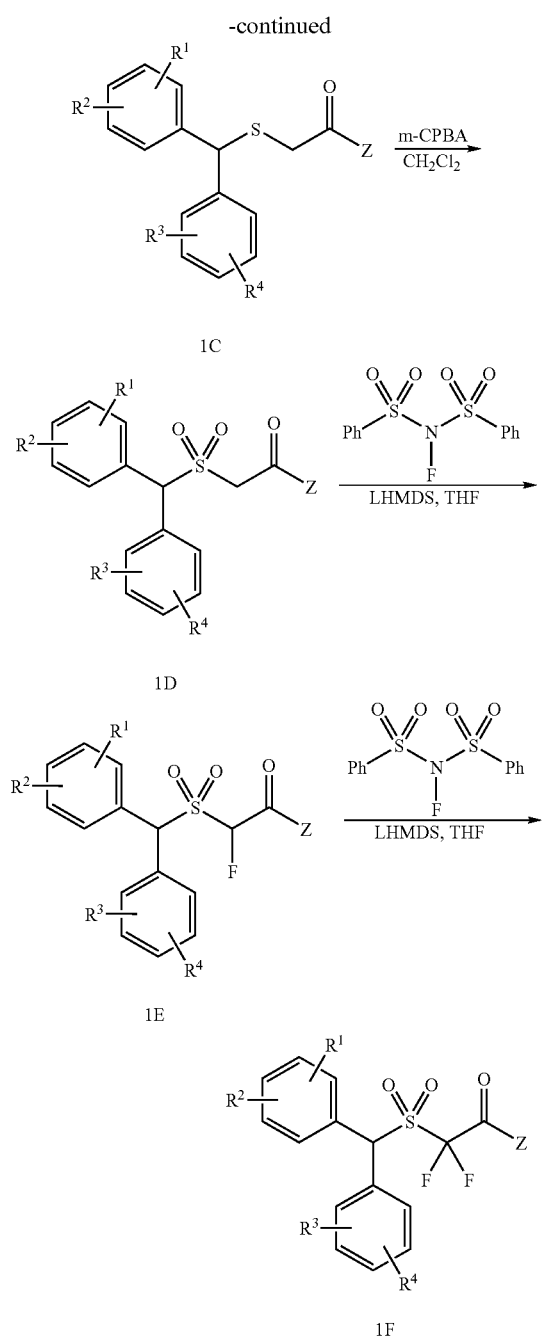

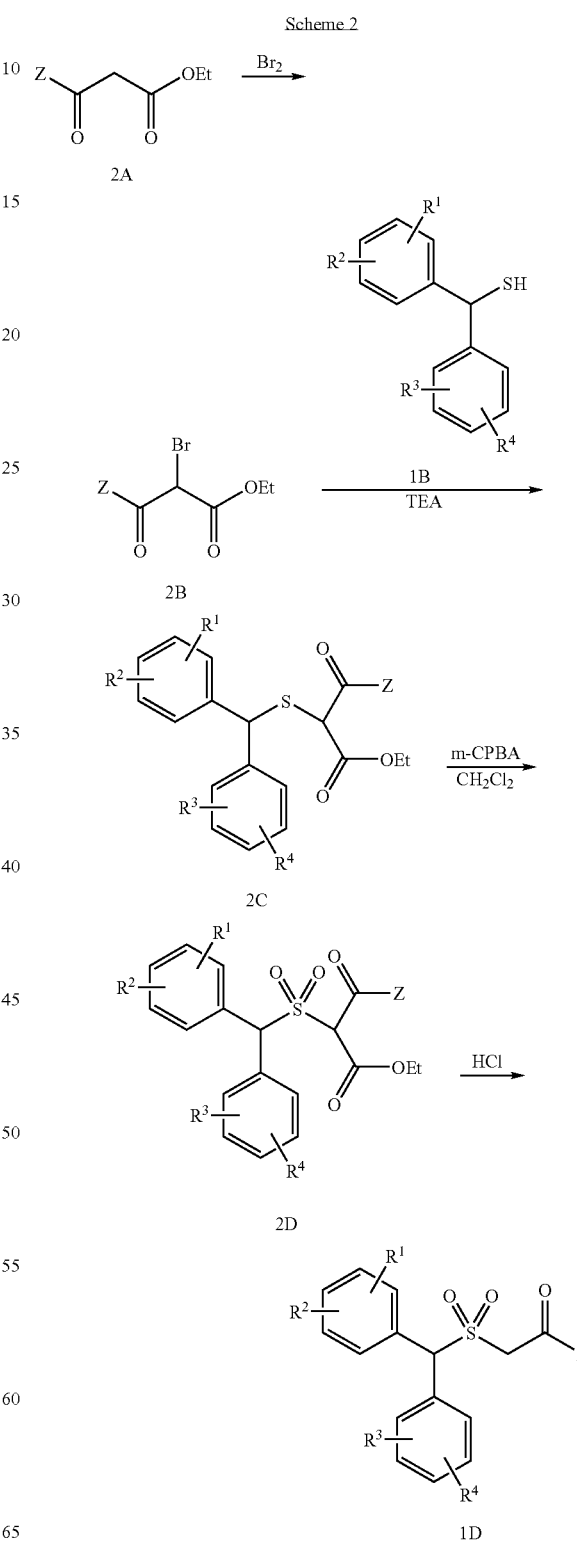

acid. Compounds 1D can be de-protonated using lithium hexamethyldisilazide (LHMDS) or lithium diisopropylamide (LDA) in THF, and treated with a fluorinating agent such as N-fluorobenzenesulfonimide to give 1E. Compounds 1E can be typically further fluorinated under the same reaction condition to yield 1F.

Substituted benzhydryl halides 1A (Scheme 1) are commercially available or may be prepared by well-known methods, such as those described by Kice J. L. and Rudzinski J. J., *J. Am. Chem. Soc.* 1987; 109:2414. Reaction of 1 with thiourea in THF (tetrahydrofuran) at reflux, then treatment with a solution of 50% NaOH in water generally gives 1B (Klenk M. M.; Suter C. M., Archer S., *JACS* 1948; 70:3846). Compounds 1B react with α-chloro- or bromoketones in THF in presence of triethylamine, or in presence of 1,8-diazabicyclo[5.4.0]undec-7-ene (DBU) in acetonitrile affording 1C. The α-chloro- or bromoketones are either commercially available or may be prepared by well-known methods, such as those disclosed in WO 99/35130 and H. McKennis et al., *JOC,* 1963; 28:383. Compounds 1D can be obtained by oxidation of 1C using mCPBA (3-chloroperoxybenzoic acid) in $CH_2Cl_2$ or hydrogen peroxide in acetic Compounds 1D can also be obtained by another synthetic route outlined in Scheme 2. Compounds 2A are commercially available or may be prepared by well-known methods. Reaction of β-ketoesters 2A with bromine gives compounds 2B. Displacement reaction of 2B with 1B in the presence of a base such as triethylamine typically affords compounds 2C. Oxidation of compounds 2C with hydrogen peroxide in acetic acid or with 3-chloroperoxybenzoic acid (m-CPBA) in dichloromethane gives 2D. Hydrolysis and decarboxylation of 2D, following known procedures such as those described by Heffner R. J. et al., *Synth. Commun.* 1991; 21,2231–2256, affords the desired products 1D.

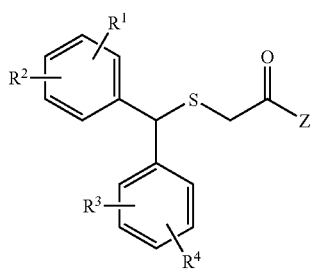

1C

Another synthetic approach to compounds 1C is shown in Scheme 3. Substituted benzhydrols 3A are readily prepared (Khurana J. M. et al. G. C. *J. Chem. Soc. Perkin Trans,* 1996; 1:2213) and react with thioglycolic acid in trifluoroacetic acid or in dichloromethane with zinc iodide catalysis to give thioethers 3B (Carceller E. et al., *J. Med. Chem.* 1993; 36:2984; and Babu S. D. et al., *Can. J. Chem.* 1989; 67:1071). Acids 3B can be converted to Weinreb amides 3D via acid chloride intermediates 3C using standard methods well known in the art of organic chemistry. Weinreb amides 3D can also be obtained using a one step reaction involving a coupling reagent (Dhainaut A. et al., *J. Med. Chem.* 2000; 43:2165–2175). Ketones 1C can be formed by reacting compounds 3D with an appropriate Grignard reagent (e.g., Newman, *J. Org. Chem.* 1948; 13:592; Edwards. *J. Org. Chem.* 1964; 29:913; Olah, *Synthesis* 1984:228), or reacting compounds 3B with an appropriate lithium reagent (e.g., Hlasta, *Tetrahedron Lett.* 1989; 30:1773; Nahm, *Tetrahedron Lett.* 1981; 22:3815). Oxidation of 1C to yield 1D can be carried out using m-CPBA in dichloromethane as described in Scheme 1.

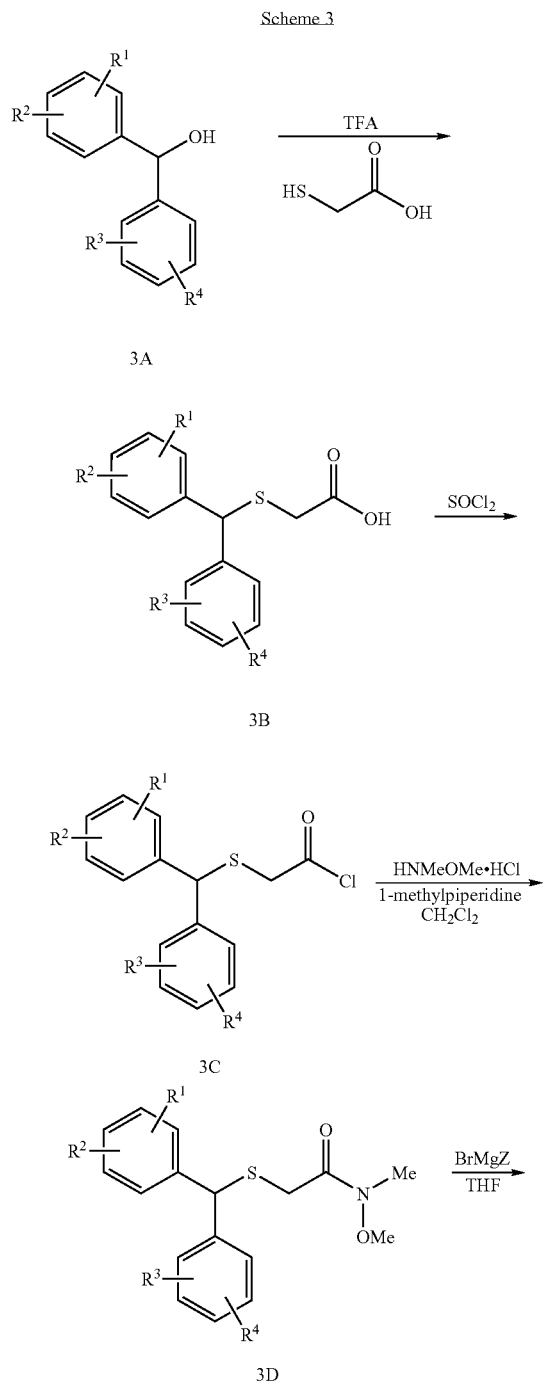

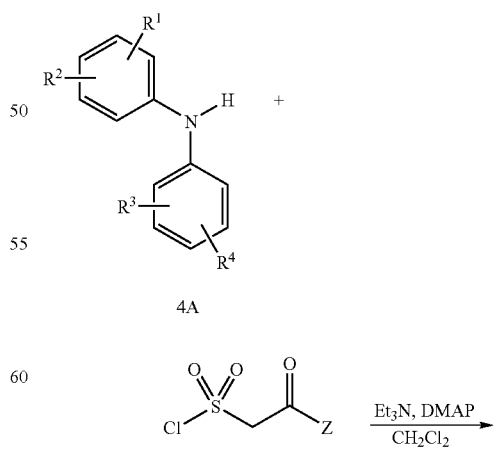

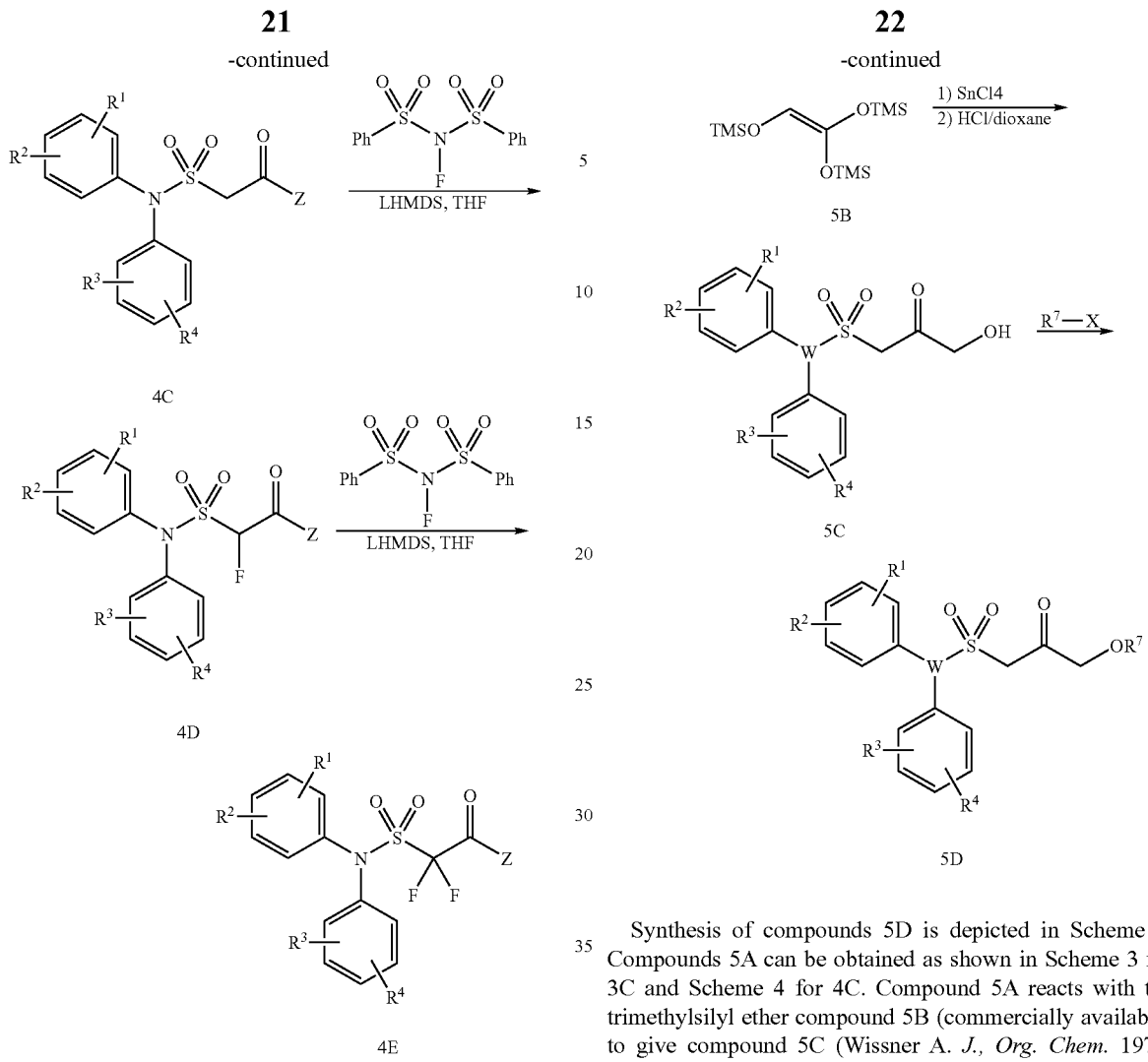

A synthetic scheme for amides of 4E is shown in Scheme 4. Compounds 4A are commercially available or may be prepared by well-known methods. Compounds 4B can be prepared using known procedures, such as those described by Ogura F., et al., *Bull. Chem. Soc. Jpn* 1983; 56:1257–1258. The coupling reaction of 4A and 4B in the presence of a base such as triethylamine and optionally 4-(N,N-dimethylamino)pyridine usually gives compound 4C (Reverdin and Crepieux, *Chem. Ber.* 1902; 35:1441). Compounds 4D and 4E can be obtained from 4C via fluorinations (e.g., with N-fluorobenzenesulfonimide) as discussed above in Scheme 1.

Synthesis of compounds 5D is depicted in Scheme 5. Compounds 5A can be obtained as shown in Scheme 3 for 3C and Scheme 4 for 4C. Compound 5A reacts with the trimethylsilyl ether compound 5B (commercially available) to give compound 5C (Wissner A. *J., Org. Chem.* 1979; 44:4617–4622). The O-alkylation of 5C with a compound of $R^7$—X, where X is Cl, Br, F, or I using well-known methods usually gives the desired products 5D. Examples of $R^7$—X include alkyl halides (e.g., $CH_3CH_2Br$).

Scheme 5

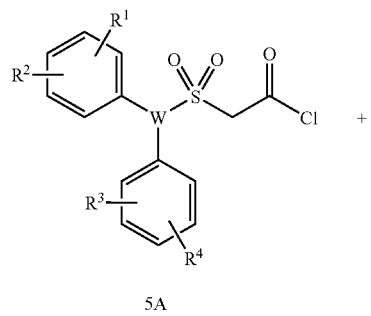

Scheme 6

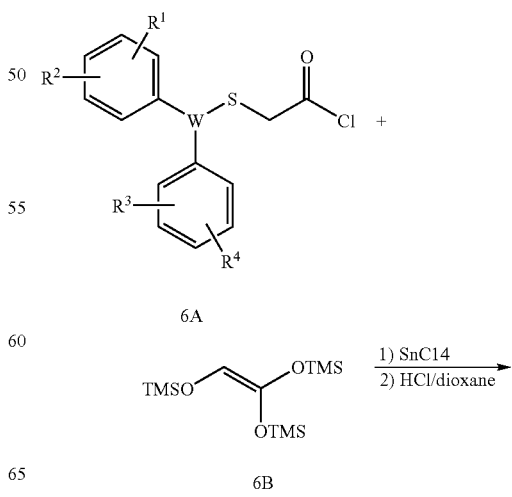

-continued

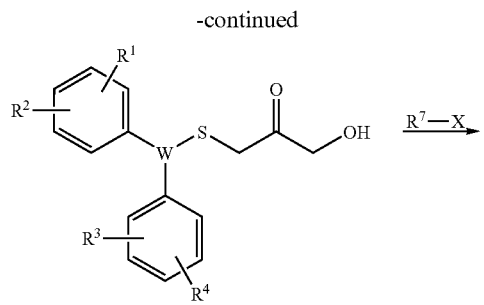

6C

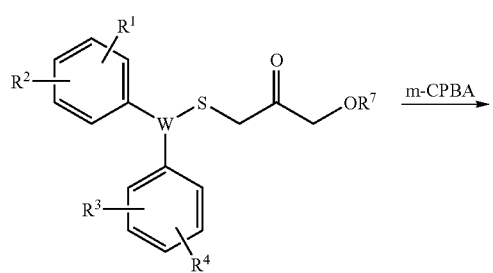

6D

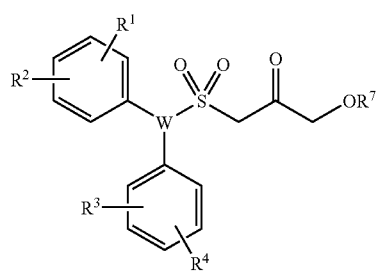

5D

As shown in Scheme 6, the same chemistry as depicted in Scheme 5 can be performed on the thioether (sulfanyl) compounds 6A to get 6D, which can be oxidized to give desired compound 5D.

-continued

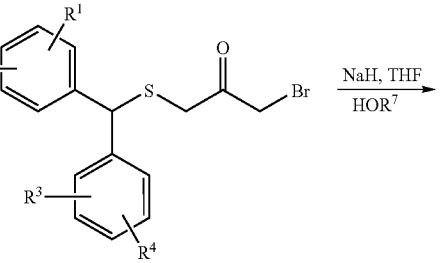

7A

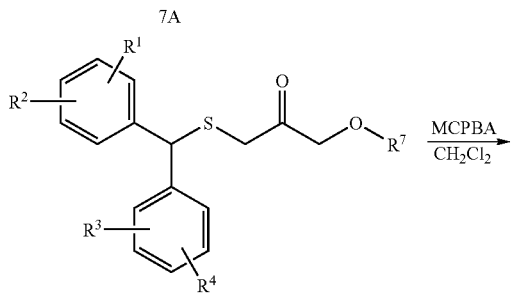

7B

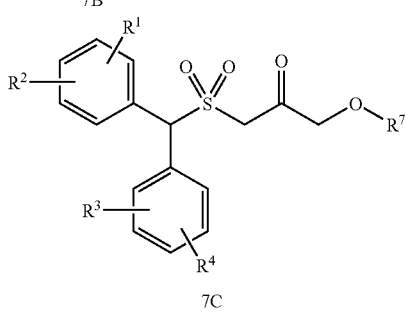

7C

Compounds 1B can be alkylated with 1,3-dibromoacetone (Scheme 7) or 1,3-dichloroacetone (Scheme 8) to give compounds 7A or 8A in the presence of a base such as triethylamine (Et$_3$N) in THF. Both acetone derivatives are available from ACROS Organics Inc, Belgium. Compounds 7A or 8A can then react with an appropriate alcohol (e.g., HOR$^7$) in the presence of a base such as NaH in THF to give compounds 7B (Langer P. et al., *Syn. Lett.* 2000; 6:844–846). The oxidation of compounds 7B with m-CPBA typically give compounds 7C as discussed above.

Scheme 7

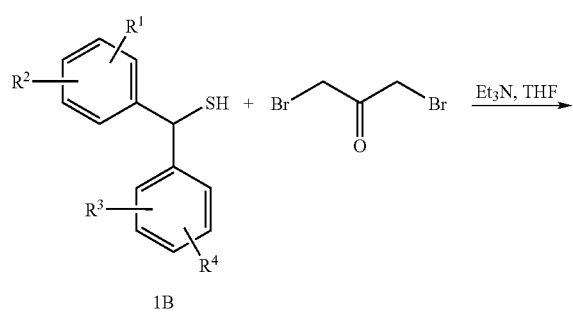

1B

Scheme 8

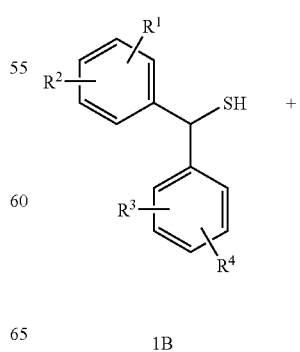

1B

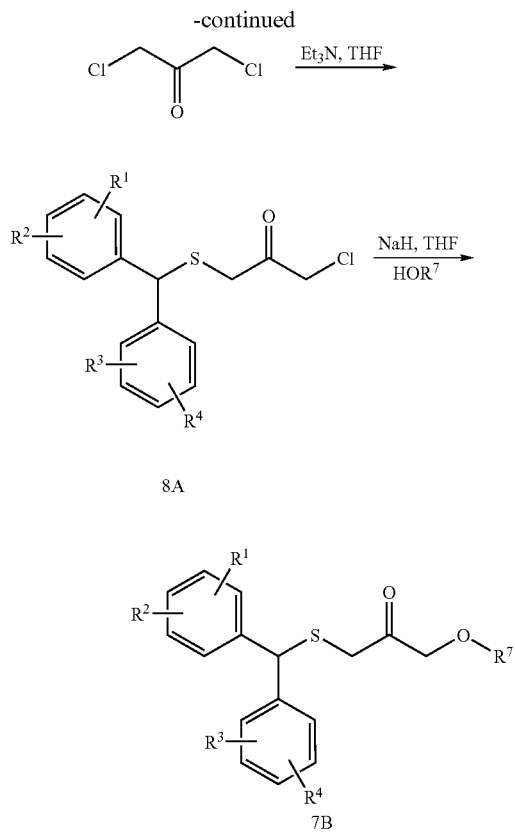
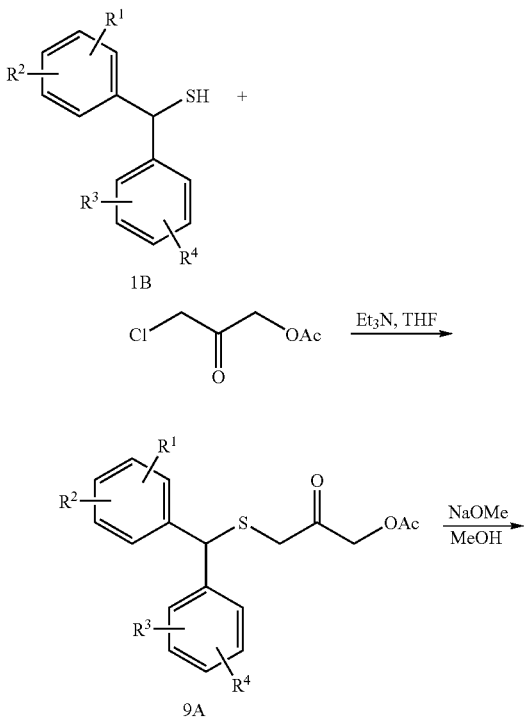
Scheme 9
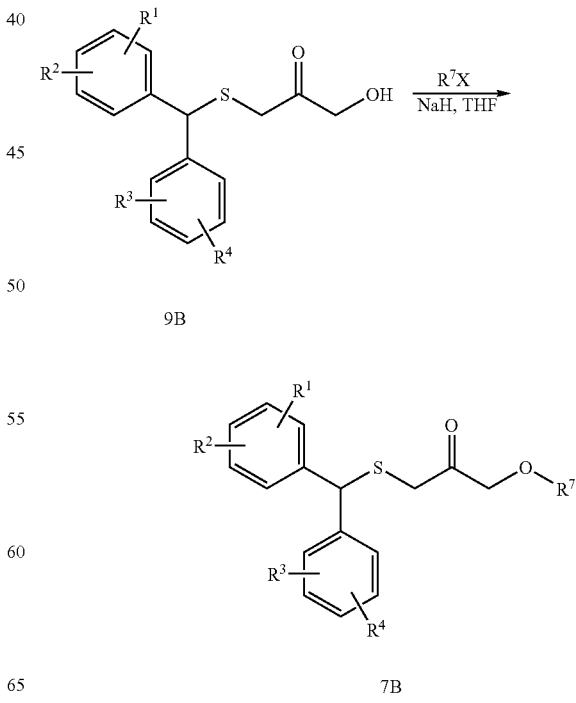
As shown in Scheme 9, compound 1B can be alkylated with 1-acetoxy-3-chloroacetone (commercially available from TCI America, Portland, Oreg.) as discussed above to give compounds 9A. Reaction of 9A with sodium methoxide usually gives 9B. Alcohols 9B can react with an appropriate isocyanate in presence of CuCl in DMF to give compounds 9C (Hirschmann R., *J. Org. Chem.* 2000; 65:8307–8316).
Scheme 10

In addition to Schemes 7 and 8, an alternative synthetic scheme to arrive at 7B is the alkylation of 9B with a compound of $R^7$—X, where X is Cl, Br, F, or I. Examples of $R^7$—X include alkyl halides using well-known synthetic methods (Scheme 10).

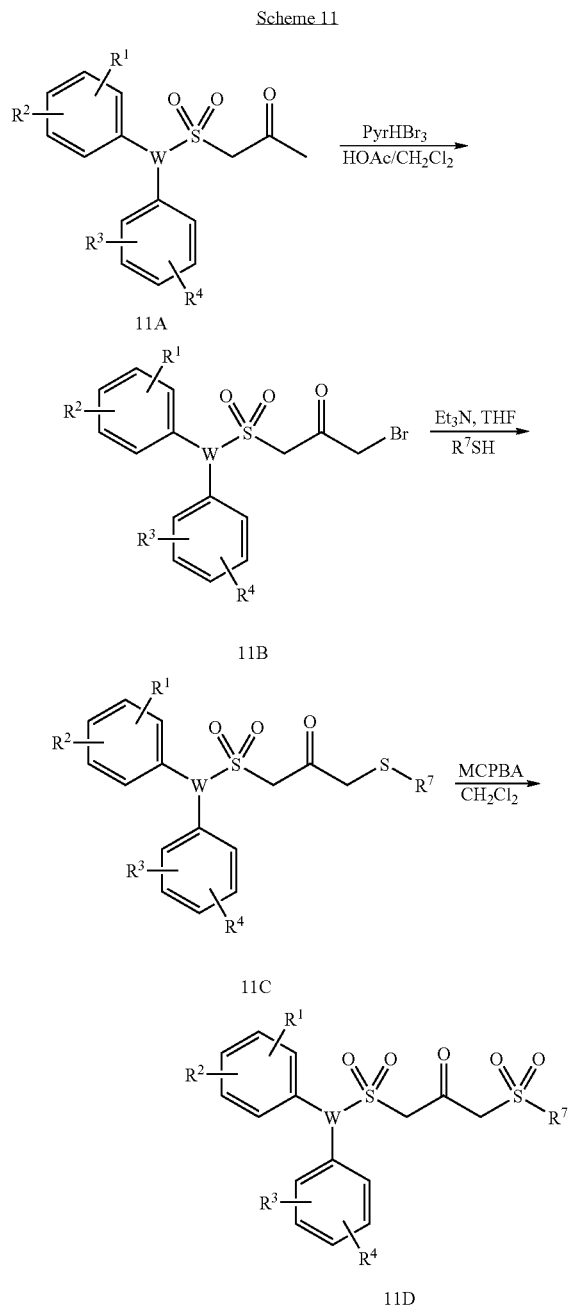

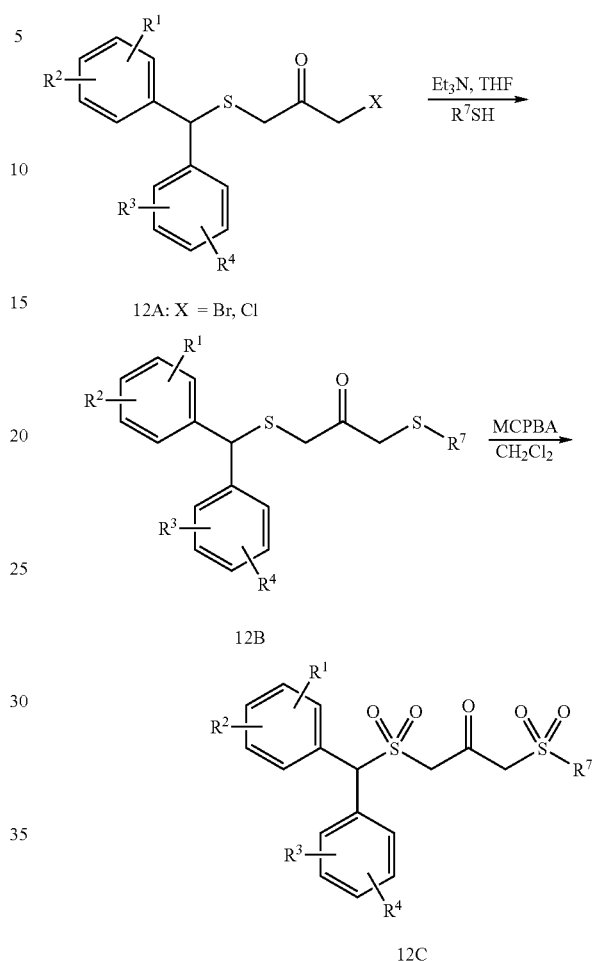

A synthetic pathway to 12C is depicted in Scheme 12. The starting compounds 12A can be synthesized using the same methods to make compounds 7A (Scheme 7) and compounds 8A (Scheme 8). 12A is then reacted with an appropriate mercaptan (e.g., $R^7$SH) in a displacement reaction. The reaction is typically carried out in the presence of a base such as triethylamine to yield 12B. The oxidation of 12B to arrive at 12C using m-CPBA can be carried out as described above.

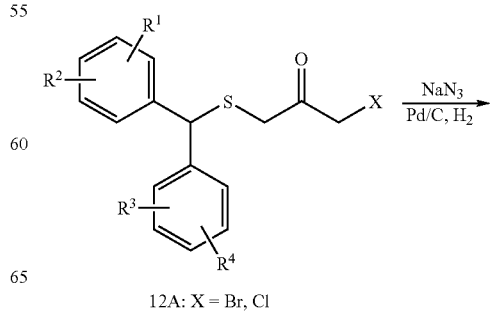

As shown in Scheme 11, methyl ketones 11A can be converted to α-bromomethyl ketones 11B using many known bromination reactions (e.g., such as Grossert J. S. et al., *Can. J. Chem.* 1984; 62:798). For example, 11A can be brominated with pyridinium bromide (PyrHBr$_3$). Reaction of 11B with an appropriate mercaptan (e.g., $R^7$SH) followed by an oxidation step with a reagent such as m-CPBA typically gives 11D.

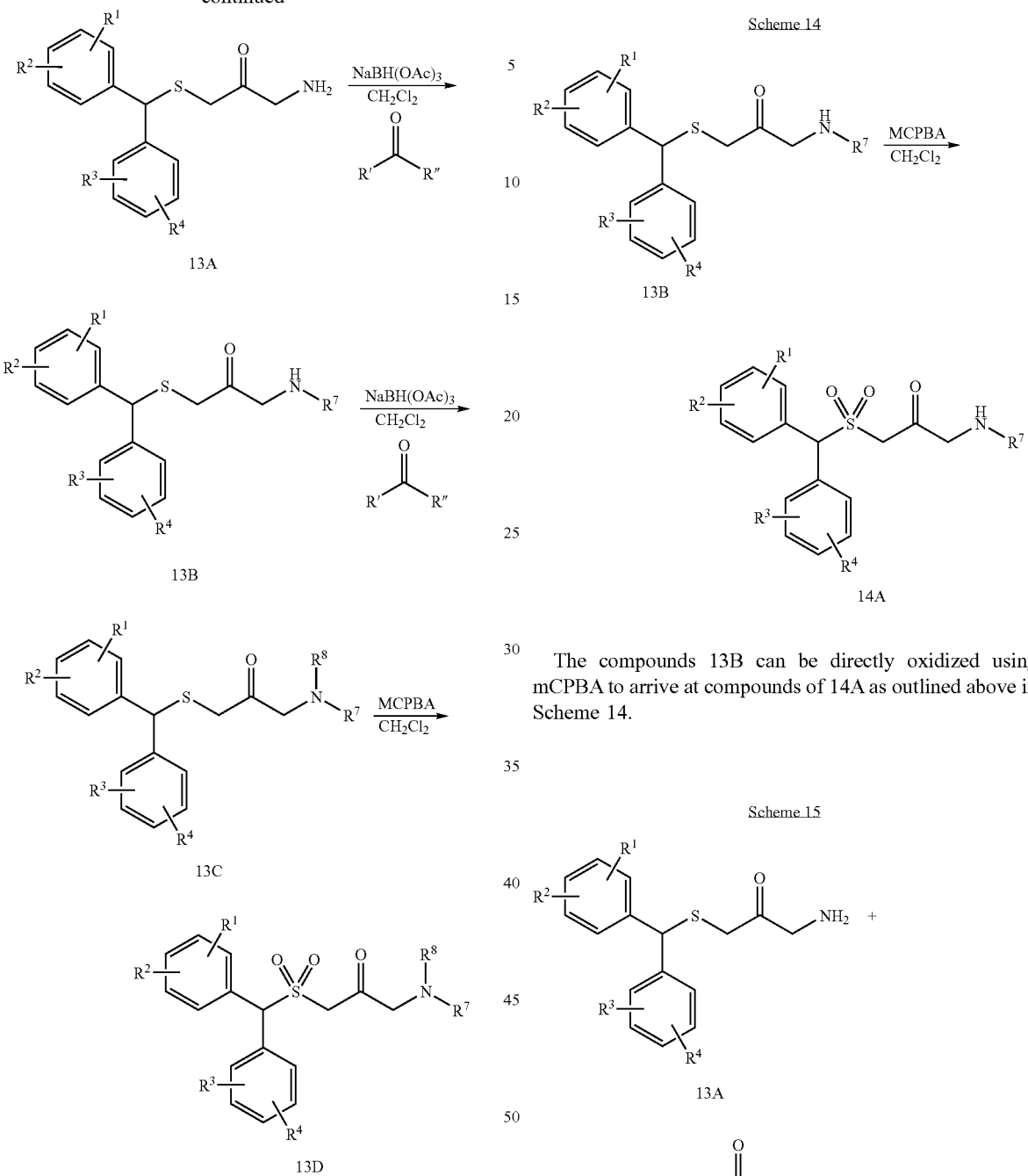

The compounds 13B can be directly oxidized using mCPBA to arrive at compounds of 14A as outlined above in Scheme 14.

A synthetic scheme for the α-aminoketones 13D is set out in Scheme 13. Compounds 12A can be converted to compounds 13A using NaN₃ following known procedures such as those described in Kiyoaki K., et al. *Bioorg. Med. Chem. Lett.* 1996; 6:2601–2606. The reductive alkylation of 13A with an appropriate ketone (R"C(O)R') or aldehyde (R"C(O)R', (i.e., where R'=H) in the presence of a reducing agent such as sodium triacetoxyborohydride (NaBH(OAc)₃) yields secondary amines 13B (Abdel-Magid A. F. et al., *J. Org. Chem.* 1996; 61:3849–3862). Under the same reaction conditions, tertiary amines 13C can be obtained from 13B. Oxidation of 13C with mCPBA gives 13D.

-continued

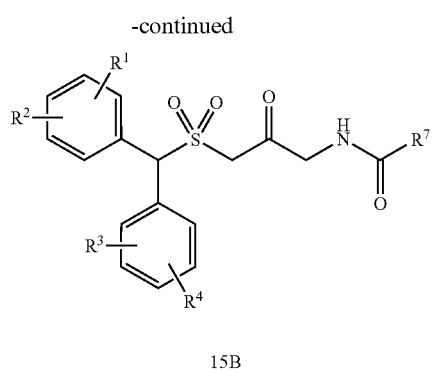

15B

The reaction of 13A with an appropriate acid chloride typically gives 15A using well-known methods. The oxidation using mCPBA 15A usually gives 15B.

Scheme 16

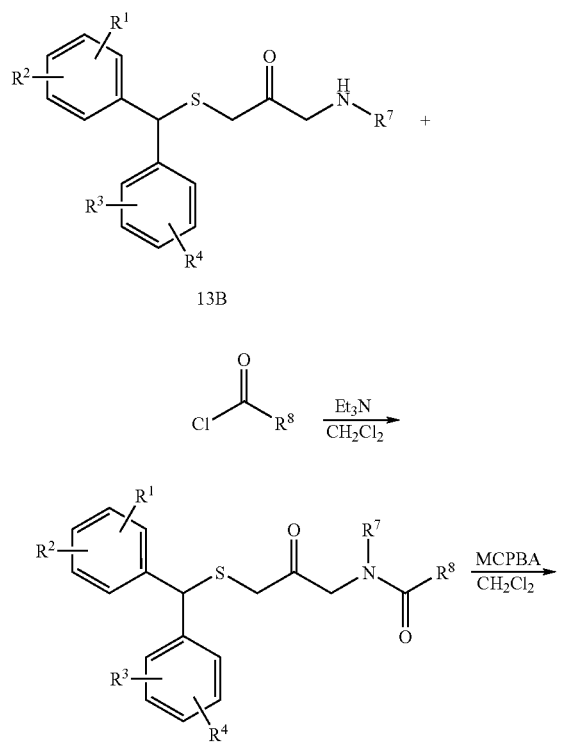

Similar to Scheme 15, 13B can be reacted with an appropriate acid chloride (e.g., Cl—C(O)—R⁸) to yield 16A. 16A can then be oxidized to yield compounds 16B using mCPBA as described herein.

Scheme 17

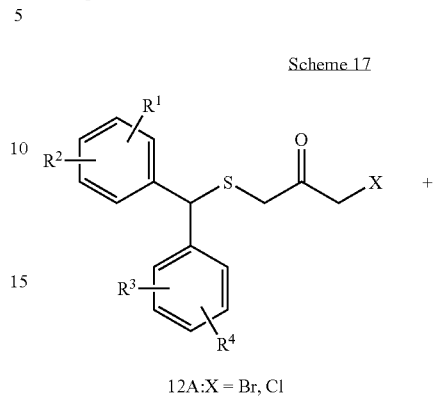

12A: X = Br, Cl

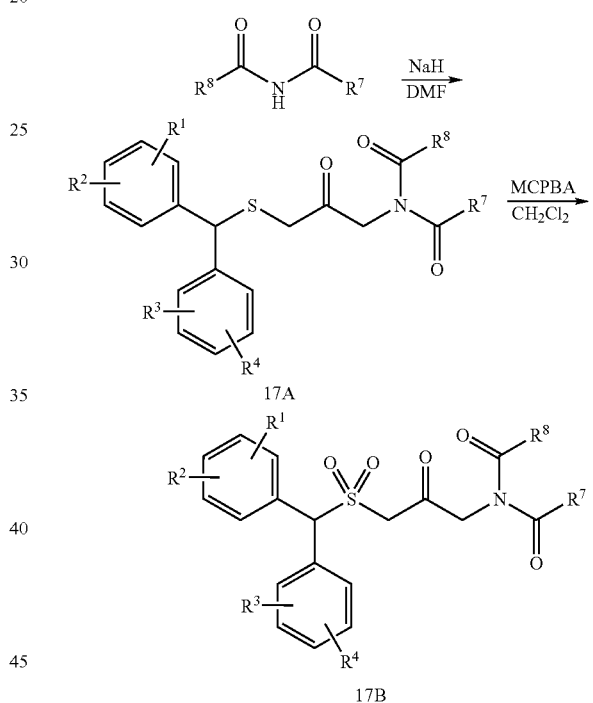

Reaction of 12A with an imine (e.g., R⁸—C(O)—NH—C(O)—R⁷) in presence of a base such as NaH in DMF usually gives compounds 17A using standard alkylation methods such as those described in Malinka W., *Pol. J. Chem.* 1995; 69:95–102. The oxidation of 17A with mCPBA typically affords 17B.

Scheme 18

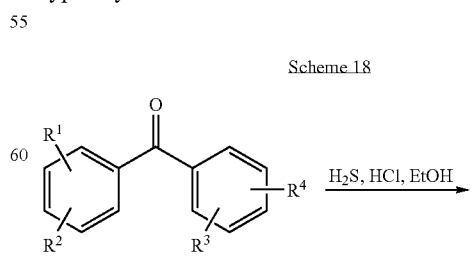

18A

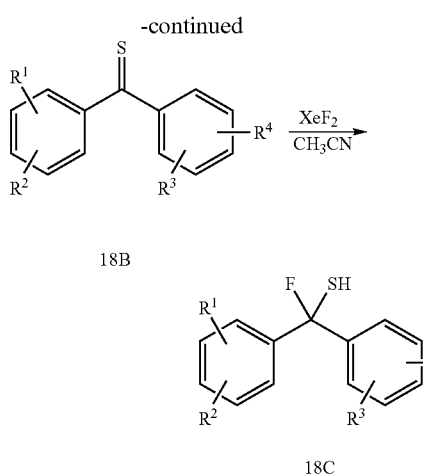

18B

18C

Synthesis of intermediates 18C is shown in Scheme 18. Compounds 18C can be used in the same way as 1B in the synthesis outlined above to yield compounds of Formula I where W=C—F. The ketones 18A can be transformed to 18B using known methods such as those described in Staudinger and Freudenberger, *Chem. Ber.* 1928; 61:1581. Compounds 18C may be synthesized from 18B using known fluorinating conditions such as those described in Gibson J. A. et al., *Can J. Chem.* 1975; 53:3044–3052.

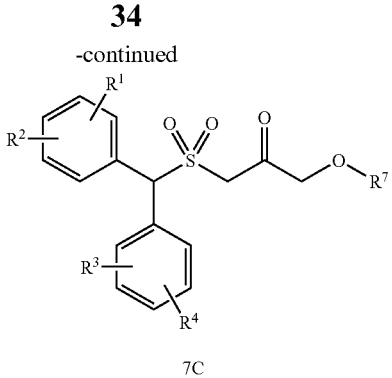

7C

An alternative synthetic scheme to produce 7B is illustrated in Scheme 19. Compound 1B reacts with an epoxide 19A to give the intermediate compounds 19B, which are usually formed in acetonitrile with tetrabutylammonium fluoride trihydrate ((t-but)$_4$N$^+$F$^-$) as a catalyst (Domenico et al., *Synthesis* 1994:34–36 and Kraynack and Pedersen *JOC* 1993; 58(22); 6114–6117). Oxidation of 19B with DMSO and acetic hydride usually gives 7B (Schmidt et al., *Synthesis* 1987:896). Further oxidation of 7B usually provides 7C by the method as described in Scheme 7. Similarly, compounds 20A, 20B, and 20C (Scheme 20) are formed by the same conditions described in Scheme 19.

Scheme 19

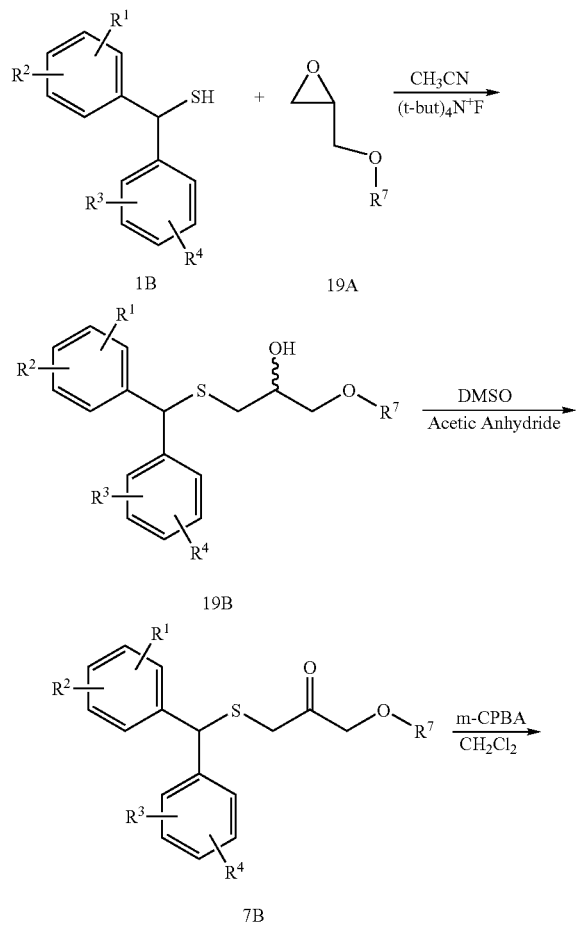

Scheme 20

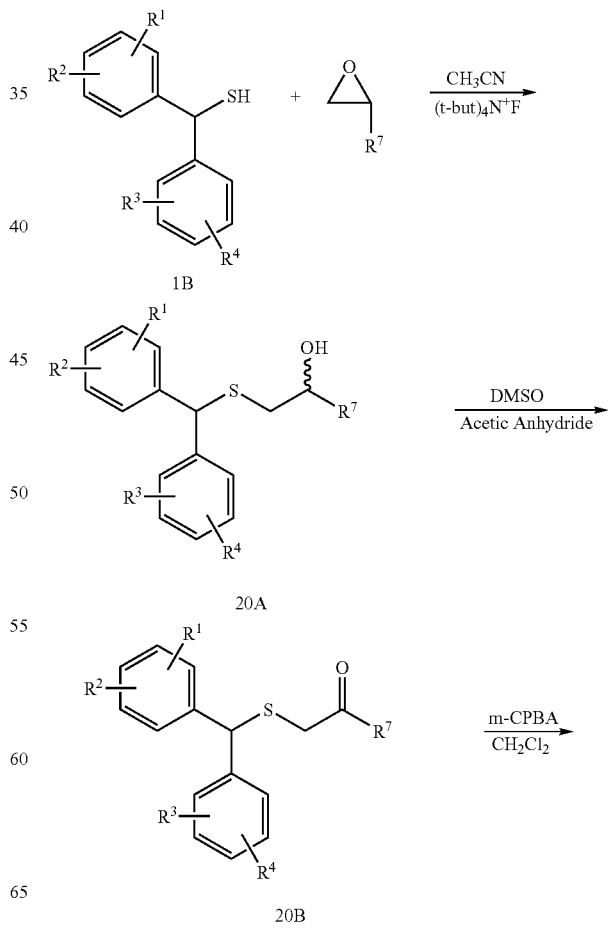

-continued

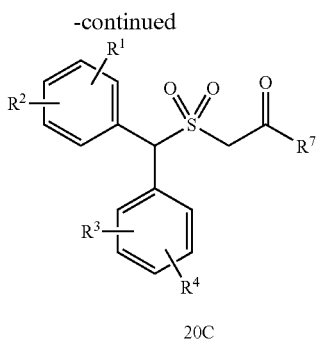

20C

3. Therapeutic Methods of the Invention

The compounds of the invention can be used to treat chemokine associated disorders in a subject. For example, the compounds, e.g., the sulfone derivatives, are valuable agents for the treatment of inflammatory diseases or conditions, atherosclerosis, restenosis, and autoimmune disorders such as arthritis and transplant rejection.

The invention pertains, at least in part, to methods for treating a chemokine associated disorders in a subject. The method includes administering to the subject an effective amount of a compound of Formula I or II, or a pharmaceutically acceptable salt of I or II:

A compound of the invention, e.g., a compound of any one of Formula I or Formula II can be administered to a patient or subject (e.g., a human) alone or in conjunction with (before, along with, or subsequent to) one or more other (compounds of the invention or another agent to be administered.

In a preferred embodiment, the disease or condition is one which is associated with lymphocyte and/or monocyte infiltration of tissues (including recruitment and/or accumulation in tissues), such as arthritis (e.g., rheumatoid arthritis), inflammatory bowel diseases (e.g., Crohn's disease, ulcerative colitis), multiple sclerosis, idiopathic pulmonary fibrosis, and graft rejection (e.g., in transplantation), including allograft rejection or graft-versus-host disease. In addition, diseases characterized by basophil activation and/or eosinophil recruitment, including allergic hypersensitivity disorders such as asthma and allergic rhinitis can be treated according to the present invention.

Other diseases that may be treated with the compounds of Formula I or Formula II are: psoriasis, chronic contact dermatitis, sarcoidosis, dermatomyositis, skin pemphigoid and related diseases (e.g., pemphigus vulgaris, p. foliacious, and p. erythematosus), glomerulonephritides, vasculitides (e.g., necrotizing, cutaneous, and hypersensitivity vasculitis), hepatitis, diabetes, systemic lupus erythematosus, and myasthenia gravis. In addition to psoriasis, other inflammatory dermatoses such as dermatitis, eczema, atopic dermatitis, allergic contact dermatitis, urticaria and reperfusion injury can also be treated.

Other chemokine associated disorders include, but are not limited to, idiopathic pulmonary fibrosis, graft rejection, allograft rejection, allergic hypersensitivity disorders, psoriasis, chronic contact dermatitis, sarcoidosis, dermatomyositis, skin pemphigoid, pemphigus vulgaris, p. foliacious, p. erythematosus, glomerulonephritides, vasculitides including necrotizing, cutaneous and hypersensitivity vasculitis; hepatitis, diabetes, systemic lupus erythematosus, myasthenia gravis, dermatitis, eczema, atopic dermatitis, allergic contact dermatitis, urticaria, and reperfusion injury. These diseases also may be treated using any one, or combination of compounds of the present invention.

The invention also pertains to a method of inhibiting the binding of a chemokine to CCR-2 by administering an effective inhibiting amount of a compound of the invention, eg, a compound of Formula I or Formula II such that the binding of a chemokine to CCR-2 is inhibited. In an embodiment, the chemokine is MCP-1, MCP-2, MCP-3, MCP-4, or combinations thereof. In another embodiment, the receptor is in a subject, e.g., a human, e.g., a human suffering from a chemokine mediated disorder.

4. Pharmaceutical Compositions

The invention also pertains, at least in part, to pharmaceutical compositions comprising an effective amount of one or more of compounds of Formula I or Formula II and a pharmaceutically acceptable carrier. The compounds of the present invention can be prepared and administered in a wide variety of routes of administration such as parenteral, oral, topical, rectal, inhalation, and the like. Formulations will vary according to the route of administration selected. Examples are oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. The following dosage forms may comprise as the active component, a compound of Formula I or Formula II or a corresponding pharmaceutically acceptable salt of a compound of Formula I or Formula II. For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in a pharmaceutically acceptable carrier, such as, aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water or another suitable carrier with viscous material, such as natural or synthetic gums, resins, methylcellulose, sodium carboxymethylcellulose, and other well-known suspending agents. Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg, or from 1% (w/w) to 95% (w/w), according to the particular application and the potency of the active component. The composition can, if desired, also contain other compatible therapeutic agents.

In therapeutic use as agents for the treatment of inflammatory diseases, inflammatory diseases, atherosclerosis, restenosis, and immune disorders such as arthritis and transplant rejection, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Some of the compounds of the invention, e.g., compounds of Formula I or Formula II are capable of further forming both pharmaceutically acceptable acid addition and/or base salts. All of these forms are within the scope of the present invention.

Pharmaceutically acceptable non-toxic acid addition salts of the compounds of Formula I or Formula II include nontoxic salts derived from inorganic acids such as hydrochloric, nitric, phosphoric, sulfuric, hydrobromic, hydriodic, hydrofluoric, phosphorous, and the like, as well as nontoxic salts derived from organic acids, such as aliphatic mono- and dicarboxylic acids, 2-phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., Pharmaceutical Salts. *J. Pharma. Sci.* 1977:66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms can differ from their respective salt forms somewhat in certain physical properties such as solubility in polar solvents.

Pharmaceutically acceptable non-toxic base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, supra., 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms can differ from their respective salt forms somewhat in certain physical properties such as solubility in polar solvents.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate mixtures thereof.

In an embodiment, the effective amount is effective to treat a chemokine associated disorder in a subject. Examples of chemokine associated disorders include anaphylaxis, systemic necrotizing vasculitis, systemic lupus erthyematosus, serum sickness syndromes, psoriasis, arthritis, rheumatoid arthritis, osteoarthritis, inflammatory bowel diseases, Crohn's disease, ulcerative colitis, adult respiratory distress syndrome, allergic rhinitis, atopic dermatitis, asthma and other allergic responses, and reperfusion injury occurring after periods of ischemia such as in myocardial infarction, shock, cancer, Alzheimer's disease, dementias related to Alzheimer's disease, Pick's disease, Parkinson's, Lewy diffuse body diseases, multiple sclerosis, amyotrophic lateral sclerosis, progressive supranuclear palsy, epilepsy, and Jakob-Creutzfieldt disease, stroke, traumatic injury to the brain, traumatic injury to the spinal cord, spinal crush, central and peripheral nervous system trauma, immune thyroiditis, hyperthyroidism, type 1 diabetes mellitus, insulin related diabetes, Addison's disease, autoimmune oophoritis, autoimmune orchitis, AIDS, autoimmune hemolytic anemia, paroxysmal cold hemoglobinuria, autoimmune thrombocytopenia, autoimmune neutropenia, pernicious anemia, autoimmune coagulopathies, myasthenia gravis, multiple sclerosis, experimental allergic encephalomyelitis, pemphigus and other bullous diseases, rheumatic carditis, Goodpasture's syndrome, postcardiotomy syndrome, erythematosus, arthritis, rheumatoid arthritis, osteoarthritis, keratitis, parotitis, polymositis, scleroderma, idiopathic pulmonary fibrosis, graft rejection, allograft rejection, allergic hypersensitivity disorders, psoriasis, chronic contact dermatitis, sarcoidosis, dermatomyositis, skin pemphigoid, pemphigus vulgaris, p. foliacious, p. erythematosus, glomerulonephritides, vasculitides, hepatitis, systemic lupus erythematosus, myasthenia gravis, dermatitis, eczema, atopic dermatitis, allergic contact dermatitis, urticaria, and reperfusion injury. In an advantageous embodiment, the chemokine associated disorder is atherosclerosis or rheumatoid arthritis.

EXAMPLES

The following nonlimiting examples illustrate preferred methods for preparing compounds of the invention.

Example 1

1-[Bis-(4-chloro-phenyl)-methanesulfonyl]-propan-2-one

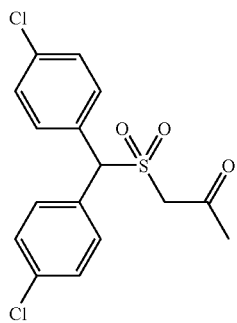

Step A: 2-[Bis-(4-chloro-phenyl)-methylsulfanyl]-N-methoxy-N-methyl-acetamide

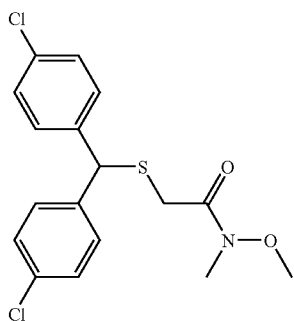

Prepared as an oil in 57% yield from [bis-(4-chlorophenyl)-methylsulfanyl]-acetic acid (Boschelli D. H., et al. U.S. Pat. No. 5,571,825) by the procedure described below. A suspension of (diphenyl-methanesulfonyl)-acetic acid (Carceller E. et al., *J. Med. Chem.* 1993; 36:2984–2997; 0.50 g, 1.7 mmol) and 3 drops of N,N-dimethylformamide in dichloromethane (5.0 mL) was cooled to 0° C. and treated dropwise via syringe with oxalyl chloride (0.18 mL, 0.26 g, 2.1 mmol). The mixture was stirred at 0° C. for 1 hour, then at room temperature for an additional 3 hours. The reaction mixture was evaporated to give 4.2 g (100%) of the crude acid chloride intermediate. A solution of this intermediate (0.53 g, 1.7 mmol) in dichloromethane (10.0 mL) was added dropwise to a mixture of N,O-dimethylhydroxylamine hydrochloride (0.20 g, 2.1 mmol) and 1-methylpiperidine (0.74 mL, 0.60 g, 6.1 mmol) in 10.0 mL of dichloromethane maintained at 0° C. during the addition. The mixture was stirred at 0° C. for 1 hour, then at room temperature for an additional 18 hours. The reaction mixture was evaporated, and the residue was dissolved in 150 mL of ethyl acetate. The solution was washed with three 50 mL portions of 1.0N hydrochloric acid, two 50 mL portions of 5% aqueous sodium bicarbonate solution, and 50 mL of brine. The organic layer was dried (sodium sulfate) and evaporated. The residue was purified by chromatography (eluting with 50% ethyl acetate/hexane) to yield 0.32 g (56%) of product; mp 136–137° C.; MS (APCI-) and $^1$H NMR consistent with desired product structure.

Step B: 1-[Bis-(4-chloro-phenyl)-methylsulfanyl]-propan-2-one

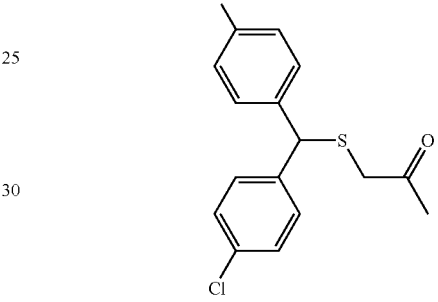

To a cold (0° C.) solution of 2-[bis-(4-chloro-phenyl)-methylsulfanyl]-N-methoxy-N-methyl-acetamide (4.1 g, 11.1 mmol) in 75 mL of anhydrous tetrahydrofuran was added 14.8 mL of methylmagnesium bromide (44.5 mmol) at such a rate as to maintain the reaction temperature at 0° C. The reaction mixture was stirred at 0° C. for 2 hours and then at room temperature for 18 hours. The excess Grignard reagent was quenched with 40 mL of saturated aqueous ammonium chloride. The mixture was diluted with 200 mL of saturated ammonium chloride solution and then extracted with three 100 mL portions of ethyl acetate. The organic layers were combined, dried (sodium sulfate), filtered, and then the filtrate was evaporated to give an oil, which was flash chromatographed (silica gel, 20% ethyl acetate in hexane) to afford 1.6 g (44%) of a colorless oil; $^1$H NMR (deuterochloroform): δ 2.21 (s, 3H), 3.09 (s, 2H), 5.09 (s, 1H), 7.26–7.31 (m, 8H); ms: m/z 323 (m–1) APCI-.

Step C: To a solution of 1-[bis-(4-chloro-phenyl)-methylsulfanyl]-propan-2-one (1.6 g, 4.9 mmol) in 100 mL of anhydrous dichloromethane was added 3-chloroperbenzoic acid (3.4 g, 19.7 mmol). The reaction mixture was stirred at room temperature for 18 hours. The reaction mixture was diluted with 200 mL of dichloromethane and washed three times with 100 mL portions of 5% sodium bicarbonate and then once with 100 mL of brine. The organic layer was dried (sodium sulfate), filtered, and the filtrate was evaporated to give an oil, which was chromatographed (silica gel, 30% ethyl acetate in hexane) to afford 1.5 g (83%) of a white solid with mp 114–115° C.; $^1$H NMR (deuterochloroform): δ 2.34 (s, 3H), 3.87 (s, 2H), 5.29 (s, 1H), 7.37–7.40 (m, 4H), 7.56–7.59 (m, 4H); ms: m/z 355 (m–1) APCI-.

Example 2

1-[Bis-(4-chloro-phenyl)-methanesulfonyl]-butan-2-one

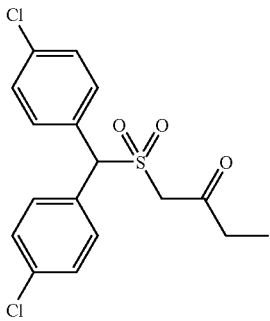

Step A: 1-[Bis-(4-chloro-phenyl)-methylsulfanyl]-butan-2-one

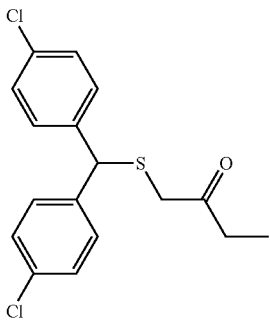

Prepared in 21% yield from 2-[bis-(4-chloro-phenyl)-methylsulfanyl]-N-methoxy-N-methyl-acetamide (Example 1, Step A, 2.1 g, 5.6 mmol) and 7.5 mL of ethylmagnesium bromide (22.4 mmol) by the procedure described in Example 1, Step B; $^1$H NMR (deuterochloroform): δ 1.02 (t, J=7.3 Hz, 3H), 2.50 (q, J=7.4 Hz, 2H), 3.06 (s, 2H), 5.10 (s, 1H), 7.23–7.30 (m, 8H); ms: m/z 337 (m−1) APCI-.

Step B:

Prepared in 86% yield from 1-[bis-(4-chloro-phenyl)-methylsulfanyl]-butan-2-one (0.34 g, 0.99 mmol) by the procedure described in Example 1, Step C; $^1$H NMR (deuterochloroform): δ 1.05 (t, J=7.1 Hz, 3H), 2.59 (q, J=7.1 Hz, 2H), 3.83 (s, 2H), 5.74 (s, 1H), 7.32–7.38 (m, 4H), 7.53–7.59 (m, 4H); ms: m/z 369 (m−1) APCI-.

Example 3

1-[Bis-(4-chloro-phenyl)-methanesulfonyl]-3-bromo-propan-2-one

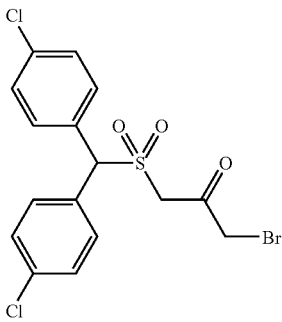

To a solution of 1-[bis-(4-chloro-phenyl)-methanesulfonyl]-propan-2-one (Example 1, 0.63 g, 1.7 mmol) in a mixture of 10 mL of acetic acid and 60 mL of dichloromethane was added pyridine hydrobromide perbromide (0.62 g, 1.9 mmol) using a procedure such as those described in Grossert J. S. et al., *Can. J. Chem.* 1984; 62:798. The reaction mixture was stirred at room temperature for 18 hours and then evaporated to give an oil. The oil was dissolved in 200 mL of ethyl acetate, washed with three 50 mL portions of 5% aqueous sodium bicarbonate and then with 50 mL of brine. The organic layer was separated, dried (sodium sulfate), filtered, and then evaporated to afford an oil, which was chromatographed (silica gel, eluting with 30% ethyl acetate in hexane) to give 0.37 g (48%) of a white solid with mp 122–123° C.; $^1$H NMR (deuterochloroform): δ 4.03 (s, 2H), 4.09 (s, 2H), 5.64 (s, 1H), 7.33–7.41 (m, 4H), 7.51–7.58 (m, 4H); ms: m/z 435 (m−1) APCI-.

Example 4

3-[Bis-(4-chloro-phenyl)-methanesulfonyl]-1,1,1-trifluoro-propan-2-one

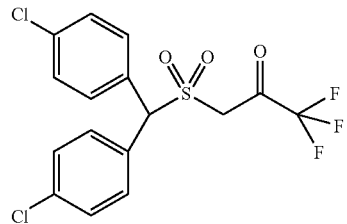

Step A: 3-[Bis-(4-chloro-phenyl)-methylsulfanyl]-1,1,1-trifluoro-propan-2-one

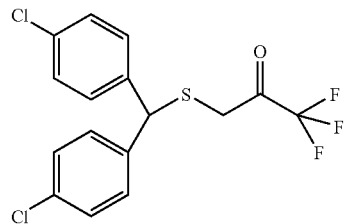

To a mixture of bis-(4-chloro-phenyl)-methanethiol prepared according to the literature procedure (Fukuda, *Yakugaku Zasshi* 1952; 72:1472, or *Chem. Abstr.*, 1953: 8706, 1 g, 3.71 mmol) in ethanol (15 mL) was added potassium tert-butoxide (417 mg, 3.71 mmol) in an ice-bath under a nitrogen atmosphere. The mixture was stirred for 10 minutes and then 3-bromo-1,1,1-trifluoroacetone (0.77 mL, 7.42 mmol) was added dropwise. The resulting mixture was stirred at room temperature for 2 hours. TLC was showed that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–12% ethyl acetate in hexanes) to give 1.05 g (75%) of the desired product as a white solid: mp 82–84° C.; $^1$H NMR (400 MHz, CDCl$_3$): 65% hydra form: δ 2.73 (s, 2H, —OH), 3.87 (s, 2H, CH$_2$), 5.54 (s, 1H, CH), 7.32–7.35 (m, 8H, ArH), and 35% ketone form: δ 3.34 (s, 2H, CH$_2$), 5.11 (s, 1H, CH), 7.32–7.35 (m, 8H, ArH); MS(APCI-): m/z 378.0 (M−H); Anal. Calcd for C$_{16}$H$_{11}$Cl$_2$F$_3$O$_1$S$_1$.0.75H$_2$O: C, 48.93; H, 3.21; S, 8.16, F, 14.51. Found: C, 48.97; H, 3.13; S, 8.06, F, 14.32.

Step B:

To a solution of 3-[bis-(4-chloro-phenyl)-methylsulfanyl]-1,1,1-trifluoro-propan-2-one from Step A (500 mg, 1.32 mmol) in methylene chloride (30 mL) was added mCPBA (683 mg, 3.96 mmol) in portions in an ice-bath under a nitrogen atmosphere. The mixture was stirred at room temperature for 1 hour. TLC and MS demonstrated that the reaction was complete. The mixture was partitioned between ethyl acetate and saturated $NaHCO_3$ solution. The organic phase was washed with water and brine, dried over $Na_2SO_4$ and filtered. The filtrate was concentrated in vacuo to give a residue, which was purified by chromatography (2%–15% ethyl acetate in hexanes) to give 161 mg (30%) of the desired product as a white foam: mp 60–62° C.; $^1$H NMR (400 MHz, $CDCl_3$): 93% hydrate form: δ 3.26 (s, 2H, —OH), 4.95 (s, 2H, $CH_2$), 5.91 (s, 1H, CH), 7.40–7.58 (m, 8H, ArH) and 7% ketone form: δ 4.16 (s, 2H, $CH_2$), 5.75 (s, 1H, CH), 7.40–7.58 (m, 8H, ArH); MS(APCI-): m/z 410.0 (M–H); Anal. Calcd for $C_{16}H_{11}Cl_2F_3O_3S_1 \cdot 0.6H_2O$: C, 45.53; H, 2.91; S, 7.60; F, 13.50. Found: C, 45.55; H, 3.19; S, 7.49; F, 13.88.

Example 5

2-[Bis-(4-chloro-phenyl)-methanesulfonyl]-1-furan-2-yl-ethanone

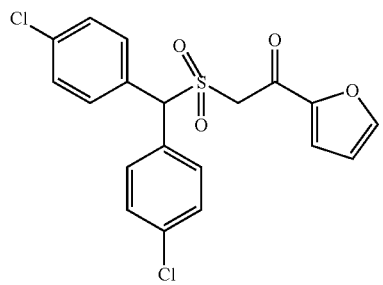

Step A: 2-[Bis-(4-chloro-phenyl)-methylsulfanyl]-1-furan-2-yl-ethanone

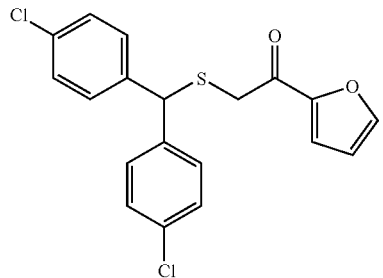

A solution of [bis-(4-chloro-phenyl)-methanethiol (Fukuda, *Yakugaku Zasshi* 1952; 72:1472; 1.3 g, 4.8 mmol) and 2-bromo-1-furan-2-yl-ethanone (Bennett G. A., Mullen G. B., Mitchell J. T., Jones W. E., Allen S. D., Kinsolving C. R., St. Georgiev V., *Eur. J. Med. Chem.*, 1989; 24:579; 1.0 g, 5.3 mmol) in 15 mL of acetonitrile was cooled in ice and treated slowly with 1,8-diazabicyclo[5.4.0]undec-7-ene (DBU; 0.75 mL, 0.76 g, 5.0 mmol), and the mixture was stirred at room temperature for 18 hours. The reaction mixture was added to 200 mL of brine, and the new mixture was extracted with four 75 mL portions of ethyl acetate. The combined organic layers were washed with two 200 mL portions of brine. The organic layer was dried (sodium sulfate) and evaporated. The residue was purified by chromatography (eluting with 50% ethyl acetate/hexane) to yield 1.0 g (56%) of product; mp 84–85° C.; MS (APCI-), m/z 377; $^1$H NMR consistent with desired product structure.

Step B:

A suspension of 2-[bis-(4-chloro-phenyl)-methylsulfanyl]-1-furan-2-yl-ethanone (0.93 g, 2.5 mmol) in 10 mL of glacial acetic acid was treated slowly with 1.5 mL (13.2 mmol) of 30% aqueous hydrogen peroxide solution, and the mixture was stirred at room temperature for 45 minutes. An additional 20 mL of acetic acid was added, followed by 1.5 mL (13.2 mmol) of fresh 30% aqueous hydrogen peroxide solution. The reaction mixture was stirred at room temperature for 18 hours and added in portions to 250 mL of cold saturated sodium bisulfite solution. An additional 100 mL of water was added, and the mixture was stirred for 1 hour. The precipitated solid was filtered and stirred in a solution of 100 mL of 5% aqueous sodium bicarbonate and 20 mL of methanol. The solid was again filtered, and the crude product was purified by chromatography (eluting with 25% hexane in dichloromethane) to yield 0.76 g (76%) of product. A sample recrystallized from ethyl acetate/hexane had a mp of 138–139° C.; MS (APCI-), m/z 409; $^1$H NMR consistent with desired product structure.

Example 6

1-[Bis-(4-chloro-phenyl)-methanesulfonyl]-pent-3-yn-2-one

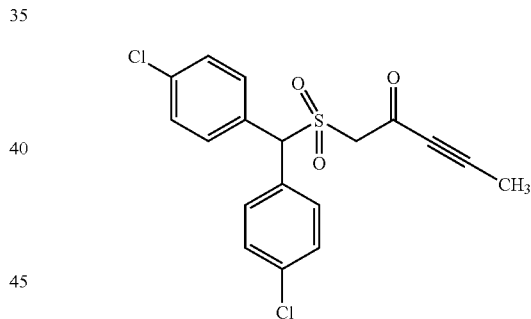

Step A:

To a stirring solution of the Weinreb amide (Example 1, Step A; 1.0 g, 2.7 mmol) in dry THF (10 mL), under nitrogen at 0° C., was added 1-propynyl magnesium bromide (0.5 M in THF, 16 mL, 0.1 mol) over a 10-minute period. It was then stirred overnight while slowly warming to room temperature, and after 18 hours the mixture was diluted with saturated sodium bicarbonate and extracted with ethyl acetate. The organic layer was dried on sodium sulfate, filtered, and concentrated under reduced pressure to give an oil which was used without further purification.

Step B:

To a stirring solution of the sulfide obtained from the Step A of Example 6 (0.3 g, 8.5 mmol) in dry methylene chloride (10 mL), under nitrogen at 0° C. was added m-CPBA (0.44 g, 2.6 mmol) and the mixture stirred for 2 hours without warming. It was then concentrated under reduced pressure, diluted with saturated sodium bicarbonate and extracted with ethyl acetate. The organic layer was dried on sodium sulfate, filtered and concentrated under reduced pressure to give an oil which was purified on silica with 10%–20% ethyl acetate-hexane to give 0.150 g (46%) of 1-[Bis-(4-chloro-phenyl)-methanesulfonyl]-pent-3-yn-2-one as a colorless oil. Anal Calc for $C_{18}H_{14}C_{12}O_3S_1$: Calc: C, 56.70; H, 3.70; S; 8.41. Found: C, 56.74; H, 4.02; S, 8.23. $^1$H NMR (400 MHz, CDCl$_3$): δ 2.1 (s, 3H), 4.0 (s, 2H), 5.8 (s, 1H), 7.4 (d, 4H, J=8.6 Hz), 7.55 (d, 4H, J=8.6 Hz).

Example 7

3-[Bis-(4-chloro-phenyl)-methanesulfonyl]-1-fluoro-propan-2-one

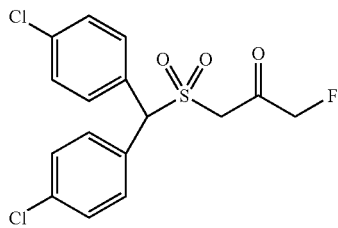

Step A: 3-[Bis-(4-chloro-phenyl)-methylsulfanyl]-1-fluoro-2-propanol

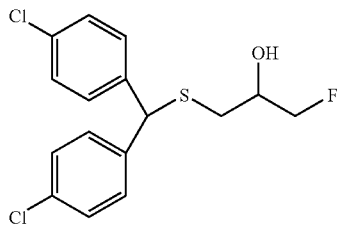

To a mixture of bis-(4-chloro-phenyl)-methanethiol, prepared according to Fukuda, *Yakugaku Zasshi* 72; 1952:1472; Chem. Abstr., 1953:8706, (1 g, 3.71 mmol) in ethanol (15 mL) was added potassium tert-butoxide (416 mg, 3.71 mmol) in an ice-bath under a nitrogen atmosphere. The mixture was stirred for 10 minutes and then 1-chloro-3-fluoro-2-propanol (417 mg, 3.71 mmol) was added dropwise. The resulting mixture was heated at reflux for 2 hours. A TLC analysis indicated that that the reaction was complete. The mixture was partitioned between ethyl acetate and saturated NaHCO$_3$ solution. The organic phase was washed with water and brine, dried over Na$_2$SO$_4$ and filtered. The filtrate was concentrated in vacuo to give a residue, which was purified by chromatography (2%–20% ethyl acetate in hexanes) to give 1.2 g (94%) of the desired product as a syrup: $^1$H NMR (400 MHz, DMSO-6d): δ 2.33–2.44 (m, 2H, CH$_2$), 3.71 (m, 1H, CH), 4.20–4.32 (m, 2H, CH$_2$F), 5.29 (d, J=5.1 Hz, 1H, OH), 5.41 (s, 1H, CH) 7.35–7.40 (m, 8H, ArH); MS(APCI-): m/z 343.0 (M–H);

Step B: 3-[Bis-(4-chloro-phenyl)-methylsulfanyl]-1-fluoro-propan-2-one

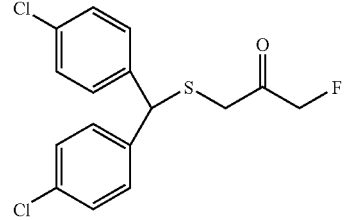

To a mixture of 3-[bis-(4-chloro-phenyl)-methylsulfanyl]-1-fluoro-2-propanol prepared from Step A (0.96 g, 2.78 mmol) in methylene chloride (50 mL) was added pyridinium dichromate (2.1 g, 5.56 mmol). The mixture was heated at reflux for 3 hours. TLC was showed that the reaction was complete. The mixture was filtered and the filtrate was partitioned between ethyl acetate and water. The organic phase was washed with water and brine, dried over Na$_2$SO$_4$, and filtered. The filtrate was concentrated in vacuo to give a residue, which was purified by chromatography (2%–20% ethyl acetate in hexanes) to give 420 mg (44%) of the desired product as a syrup: $^1$H NMR (400 MHz, DMSO-6d): δ 3.28 (s, 2H, CH$_2$), 5.04 (d, J=46.6 Hz, 2H, CH$_2$F), 5.31 (s, 1H, CH), 7.35–7.40 (m, 8H, ArH); MS(APCl-): m/z 341.0 (M–H); Anal. Calcd for $C_{16}H_{13}Cl_2F_1O_1S_1$: C, 55.99; H, 3.82; S, 9.34; F, 5.53. Found: C, 56.16; H, 3.47; S, 9.50; F, 5.92.

Step C: 3-[Bis-(4-chloro-phenyl)-methanesulfonyl]-1-fluoro-propan-2-one

To a solution of 3-[bis-(4-chloro-phenyl)-methylsulfanyl]-1-fluoro-propan-2-one prepared from Step B (360 mg, 1.05 mmol) in methylene chloride (30 mL) was added mCPBA (543 mg, 3.15 mmol) in portions in an ice-bath under a nitrogen atmosphere. The mixture was stirred at room temperature for 1 hour. TLC and MS demonstrated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–25% ethyl acetate in hexanes) to give 265 mg (67%) of the desired product as a white foam: mp 55–58° C.; $^1$H NMR (400 MHz, DMSO-6d): δ 4.26 (s, 2H, CH$_2$), 5.02 (d, J=4 Hz, 2H, CH$_2$F), 6.08 (s, 1H, CH), 7.46–7.62 (m, 8H, ArH); MS(APCI-): m/z 373.0 (M–H); Anal. Calcd for $C_{16}H_{13}Cl_2F_1O_3S_1$: C, 51.21; H, 3.49; S, 8.54. Found: C, 51.44; H, 3.48; S, 8.31.

Example 8

3-[Bis-(4-chloro-phenyl)-methanesulfonyl]-1,1-difluoro-propan-2-one

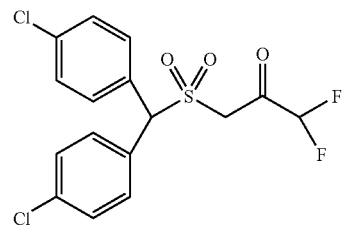

Step A: 2-Bromo-4,4-difluoro-3-oxo-butyric acid ethyl ester

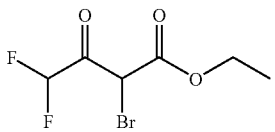

To a mixture of 4,4-difluoro-3-oxo-butyric acid ethyl ester (3 g, 18.6 mmol) and calcium carbonate (2.17 g, 21.7 mmol) in methanol (50 mL) was added bromine (0.93 mL, 18.06 mmol) dropwise in an ice-bath. After adding, the mixture was stirred for 30 minutes at room temperature and then filtered. The filtrate was concentrated in vacuo to give a residue, which was triturated with diethyl ether three times. The combined diethyl ether was dried over $Na_2SO_4$ and filtered. The filtrate was concentrated in vacuo to give 4.4 g (100%) of the crude product as a syrup: MS(APCI-): m/z 245.0 (M–H). The material was taken to the next step without further purification.

Step B: 2-[Bis-(4-chloro-phenyl)-methylsulfanyl]-4,4-difluoro-3-oxo-butyric acid ethyl ester

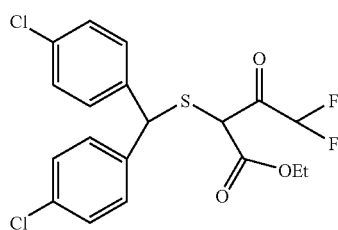

To a mixture of bis-(4-chloro-phenyl)-methanethiol (Fukuda, *Yakugaku Zasshi* 1952; 72:1472, or *Chem. Abstr.,* 1953:8706) (3 g, 11.1 mmol) in dry THF (50 mL) was added triethylamine (2.3 mL, 16.7 mmol) in an ice-bath under a nitrogen atmosphere. The mixture was stirred for 10 minutes and then a solution of the crude 2-bromo-4,4-difluoro-3-oxo-butyric acid ethyl ester (4.4 g) prepared from Step A in dry THF (5 mL) was added dropwise. The resulting mixture was stirred at room temperature for 30 minutes. TLC was showed that the reaction was complete. The mixture was partitioned between ethyl acetate and saturated $NaHCO_3$ solution. The organic phase was washed with water and brine, dried over $Na_2SO_4$, and filtered. The filtrate was concentrated in vacuo to give a residue, which was purified by chromatography (2%–20% ethyl acetate in hexanes) to give 1.49 g (16%) of the desired product as a syrup: MS(APCI-): m/z 431.0 (M–H); Anal. Calcd for $C_{19}H_{16}Cl_2F_2O_3S_1$: C, 52.67; H, 3.72; S, 7.40. Found: C, 52.74; H, 3.35; S, 7.34.

Step C: 3-[Bis-(4-chloro-phenyl)-methylsulfanyl]-1,1-difluoro-propan-2-one

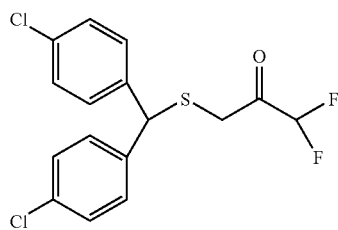

To a solution of 2-[bis-(4-chloro-phenyl)-methylsulfanyl]-4,4-difluoro-3-oxo-butyric acid ethyl ester prepared from Step B (1.2 g, 2.78 mmol) in DMF (6 mL) was added concentrated hydrochloric acid (3 mL). The mixture was heated at 100° C. for 3 hours. TLC and MS demonstrated that the reaction was complete. The mixture was partitioned between ethyl acetate and water. The organic phase was washed with water three times and brine, dried over $Na_2SO_4$, and filtered. The filtrate was concentrated in vacuo to give a residue, which was purified by chromatography (2%–10% ethyl acetate in hexanes) to give 572 mg (57%) of the desired product as a syrup: $^1$H NMR (400 MHz, DMSO-6d): δ 3.54 (s, 2H, $CH_2$), 5.28 (s, 1H, CH), 6.30 (t, J=53.0 Hz, 1H, $CHF_2$) 7.35–7.40 (m, 8H, ArH); MS(APCI-): m/z 359.0 (M–H); Anal. Calcd for $C_{16}H_{12}Cl_2F_2O_1S_1 \cdot 0.1H_2O$: C, 52.93; H, 3.39; S, 8.83. Found: C, 52.68; H, 3.16; S, 8.74.

Step D: 3-[Bis-(4-chloro-phenyl)-methanesulfonyl]-1,1-difluoro-propan-2-one

To a solution of 3-[bis-(4-chloro-phenyl)-methylsulfanyl]-1,1-difluoro-propan-2-one from Step C (540 mg, 1.5 mmol) in methylene chloride (40 mL) was added mCPBA (777 mg, 4.5 mmol) in portions in an ice-bath under a nitrogen atmosphere. The mixture was stirred at room temperature for 1 hour. TLC and MS demonstrated that the reaction was complete. The mixture was partitioned between ethyl acetate and saturated $NaHCO_3$ solution. The organic phase was washed with water and brine, dried over $Na_2SO_4$, and filtered. The filtrate was concentrated in vacuo to give a residue, which was purified by chromatography (2%–25% ethyl acetate in hexanes) to give 312 mg (53%) of the desired product as a syrup: $^1$H NMR (400 MHz, $CDCl_3$): 37% hydra form: δ 3.26 (s, 2H, $CH_2$), 4.64 (s, 2H, —OH), 5.50 (t, J=55.1 Hz, 1H, $CHF_2$), 5.93 (s, 1H, CH), 7.38–7.58 (m, 8H, ArH) and 63% ketone form: δ 4.15 (s, 2H, $CH_2$), 5.67 (s, 1H, CH), 5.88 (t, J=53.3 Hz, 1H, $CHF_2$), 7.38–7.58 (m, 8H, ArH); MS(APCI-): m/z 391.0 (M–H); Anal. Calcd for $C_{16}H_{12}Cl_2F_2O_3S_1$: C, 48.87; H, 3.08; F, 9.66; S, 8.15. Found: C, 48.60; H, 3.23; F, 9.48; S, 7.91.

Example 9

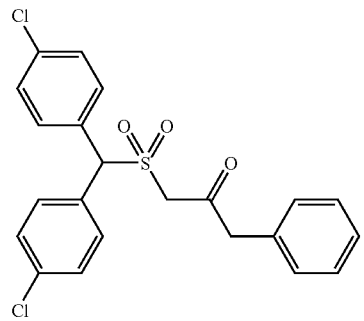

Step A: 1-[Bis-(4-chloro-phenyl)-methylsulfanyl]-3-phenyl-propan-2-ol

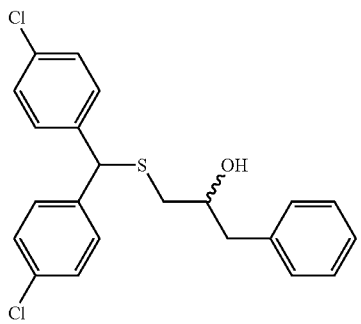

To a solution of bis-(4-chloro-phenyl)-methanethiol (Fukuda, *Yakugaku Zasshi* 1952; 72:1472; 5.0 g, 1.2 mmol) in 20 mL of acetonitrile was added tetrabutylammonium fluoride trihydrate (0.49 g, 1.6 mmol). The reaction mixture was heated to 50° C. for 5 minutes and then the reaction mixture was cooled to room temperature. A solution of 2-benzyl-oxirane (2.1 g, 15.5 mmol) in 20 mL of acetonitrile was added to the reaction mixture and then the final mixture was stirred at room temperature for 18 hours. The reaction mixture was evaporated to give an oil, which was purified by flash chromatography (silica gel, eluting with 20% ethyl acetate in hexane) to provide 4.9 g (79%) of product as a light green oil. MS (APCI-), m/z 401 (m−1); $^1$H NMR is consistent with the desired product structure.

Step B: 1-[Bis-(4-chloro-phenyl)-methylsulfanyl]-3-phenyl-propan-2-one

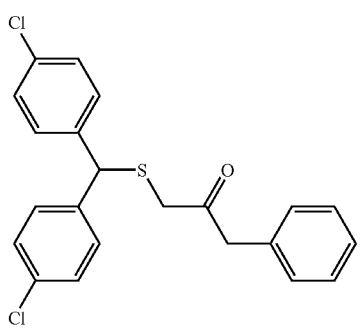

To a suspension of 1-[bis-(4-chloro-phenyl)-methylsulfanyl]-3-phenyl-propan-2-ol (3.1 g, 8.6 mmol) was added 23 mL of dimethyl sulfoxide, 10 beads of molecular sieves, followed by 15 mL of acetic anhydride. The reaction mixture was stirred at room temperature for 18 hours and then poured into 1500 mL of water. The yellow precipitate, which formed, was triturated for 30 minutes. The mixture was filtered and dried to give a solid, which was purified by flash chromatography (silica gel, eluting with 50% dichloromethane in hexane) to provide 1.7 g (57%) of product as a yellow oil. MS (APCI-), m/z 399 (m−1); $^1$H NMR is consistent with the desired product structure.

Step C: 1-[Bis-(4-chloro-phenyl)-methanesulfonyl]-3-phenyl-propan-2-one

To a solution of 1-[bis-(4-chloro-phenyl)-methylsulfanyl]-3-phenyl-propan-2-one (0.45 g, 1.1 mmol) in 25 mL of dichloromethane was added 3-chloroperoxybenzoic acid (0.78 g, 4.4 mmol). The reaction mixture was stirred at room temperature for 18 hours and then diluted up to 100 mL with dichloromethane. The organic solution was washed with 5% aqueous sodium bicarbonate (3×50 mL), followed by 50 mL of brine. The organic layer was separated, dried (sodium sulfate), filtered, and then evaporated. The residue was purified by flash chromatography (silica gel, eluting with dichloromethane) to provide 0.30 g (62%) of product as a white solid with mp 54–56° C.; MS (APCI-), m/z 431 (m−1); $^1$H NMR is consistent with the desired product structure.

Example 10

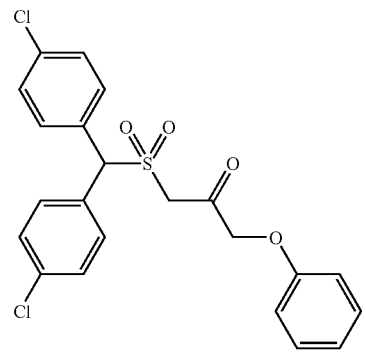

Step A: 1-[Bis-(4-chloro-phenyl)-methylsulfanyl]-3-phenoxy-propan-2-ol

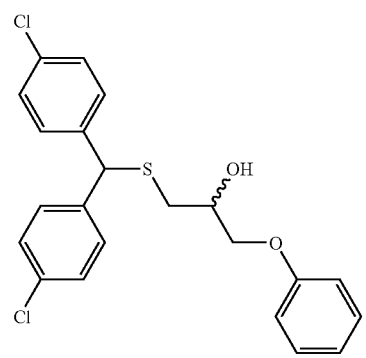

Prepared from bis-(4-chloro-phenyl)-methanethiol (5.0 g, 18.6 mmol) and 2-phenoxymethyl-oxirane (2.3 g, 15.5 mmol) by the same method as described in Step A of Example 9. Purification by flash chromatography (silica gel, eluting with 20% ethyl acetate in hexane) provided 5.5 g (70%) of product as a green oil. MS (APCI-), m/z 417 (m−1); $^1$H NMR is consistent with the desired product structure.

Step B: 1-[Bis-(4-chloro-phenyl)-methylsulfanyl]-3-phenoxy-propan-2-one

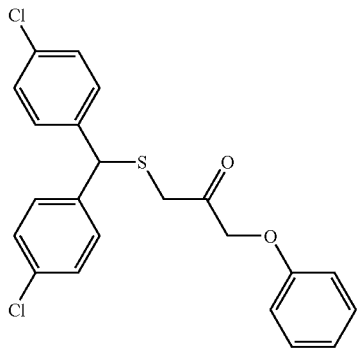

Prepared from 1-[bis-(4-chloro-phenyl)-methylsulfanyl]-3-phenoxy-propan-2-ol (1.1 g, 2.6 mmol) as described in Step B of Example 9. Purification by flash chromatography (silica gel, eluting with 50% dichloromethane in hexane) afforded 0.69 g (64%) of product as a white solid with mp 104–105° C.; MS (APCI-), m/z 415 (m–1); $^1$H NMR is consistent with the desired product structure.

Step C: 1-[Bis-(4-chloro-phenyl)-methanesulfonyl]-3-phenoxy-propan-2-one

Prepared from 1-[bis-(4-chloro-phenyl)-methylsulfanyl]-3-phenoxy-propan-2-one (0.61 g, 1.5 mmol) as described in Step C of Example 9. Purification by flash chromatography (silica gel, eluting with dichloromethane) afforded 0.32 g (48%) of product as a white solid with mp 110–112° C.; MS (APCI-), m/z 447 (m–1); $^1$H NMR is consistent with the desired product structure.

Example 11

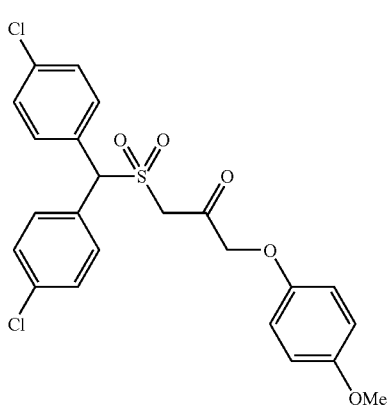

Step A: 1-[Bis-(4-chloro-phenyl)-methylsulfanyl]-3-(4-methoxy-phenoxy)-propan-2-ol

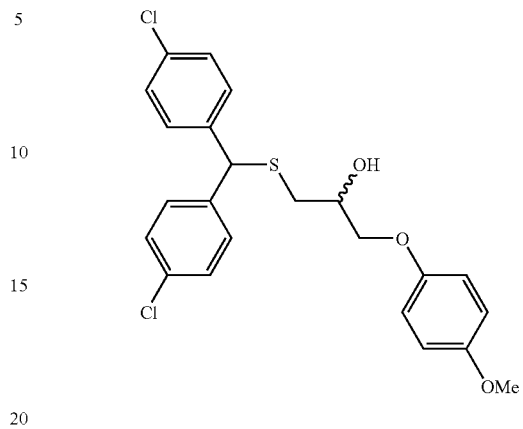

Prepared from bis-(4-chloro-phenyl)-methanethiol (5.0 g, 18.6 mmol) and 2-(4-methoxy-phenoxymethyl)-oxirane (2.8 g, 15.5 mmol) by the same method as described in in Step A of Example 9. Purification by flash chromatography (silica gel, eluting with 30% ethyl acetate in hexane) provided 5.6 g (80%) of product as a yellow solid with mp 89–91° C.; MS (APCI-), m/z 447 (m–1); $^1$H NMR is consistent with the desired product structure.

Step B: 1-[Bis-(4-chloro-phenyl)-methylsulfanyl]-3-(4-methoxy-phenoxy)-propan-2-one

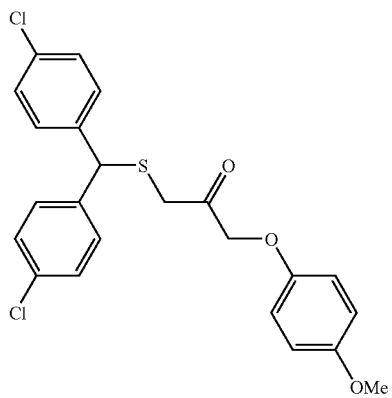

Prepared from 1-[bis-(4-chloro-phenyl)-methylsulfanyl]-3-(4-methoxy-phenoxy)-propan-2-ol (4.8 g, 10.7 mmol) by the same method as described in in Step B of Example 9. Purification by flash chromatography (silica gel, eluting with 70% dichloromethane in hexane) afforded 3.4 g (71%) of product as a white solid with mp 104–105° C.; MS (APCI-), m/z 445 (m–1); $^1$H NMR is consistent with the desired product structure.

Step C: 1-[Bis-(4-chloro-phenyl)-methanesulfonyl]-3-(4-methoxy-phenoxy)-propan-2-one Prepared from 1-[bis-(4-chloro-phenyl)-methylsulfanyl]-3-(4-methoxy-phenoxy)-propan-2-one (3.3 g, 7.3 mmol) by the same method as described in Step C of Example 9. Purification by flash chromatography (silica gel, eluting with dichloromethane) afforded 2.5 g (71%) of product as a white solid. A sample recrystallized from ethyl acetate/hexane had mp 116–117° C.; MS (APCI-), m/z 477 (m–1); $^1$H NMR is consistent with the desired product structure.

Example 12

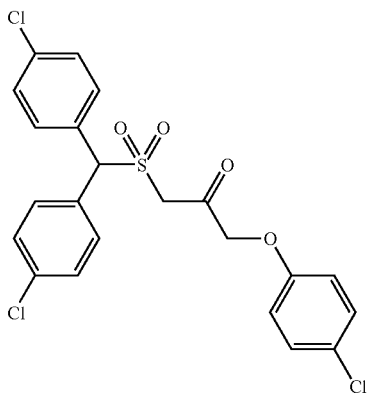

Step A: 1-[Bis-(4-chloro-phenyl)-methylsulfanyl]-3-(4-chloro-phenoxy)-propan-2-ol

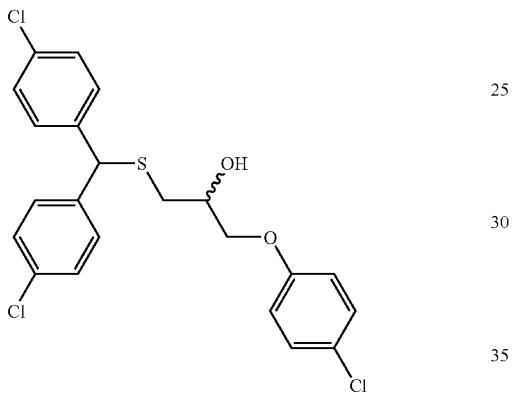

Prepared from bis-(4-chloro-phenyl)-methanethiol (5.0 g, 18.6 mmol) and 2-(4-chloro-phenoxymethyl)-oxirane (2.9 g, 15.5 mmol) by the same method as described in Step A of Example 9. Purification by flash chromatography (silica gel, eluting with 80% dichloromethane in hexane) provided 5.3 g (76%) of product as an oil. MS (APCI-), m/z 451 (m−1); $^1$H NMR is consistent with the desired product structure.

Step B: 1-[Bis-(4-chloro-phenyl)-methylsulfanyl]-3-(4-chloro-phenoxy)-propan-2-one

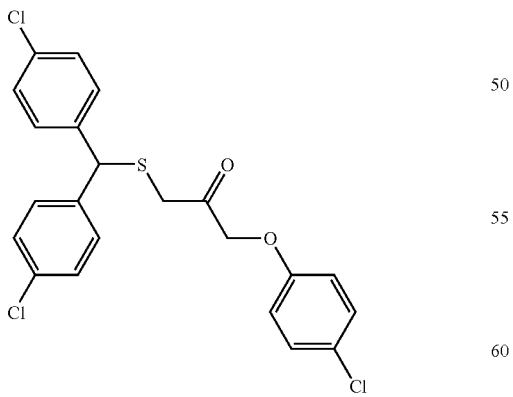

Prepared from 1-[bis-(4-chloro-phenyl)-methylsulfanyl]-3-(4-chloro-phenoxy)-propan-2-ol (5.1 g, 11.2 mmol) by the same method as described in Step B of Example 9. Purification by flash chromatography (silica gel, eluting with 50% dichloromethane in hexane) afforded 3.4 g (68%) of product as a white solid with mp 109–110° C.; MS (APCI-), m/z 449 (m−1); $^1$H NMR is consistent with the desired product structure.

Step C: 1-[Bis-(4-chloro-phenyl)-methanesulfonyl]-3-(4-chloro-phenoxy)-propan-2-one Prepared from 1-[bis-(4-chloro-phenyl)-methylsulfanyl]-3-(4-chloro-phenoxy)-propan-2-one (3.0 g, 6.7 mmol) by the same method as described in in Step C of Example 9. Purification by flash chromatography (silica gel, eluting with 80% dichloromethane in hexane) afforded 2.1 g (66%) of product as a white solid. A sample recrystallized from ethyl acetate/hexane had mp 105–107° C.; MS (APCI-), m/z 481 (m−1); $^1$H NMR is consistent with the desired product structure.

Example 13

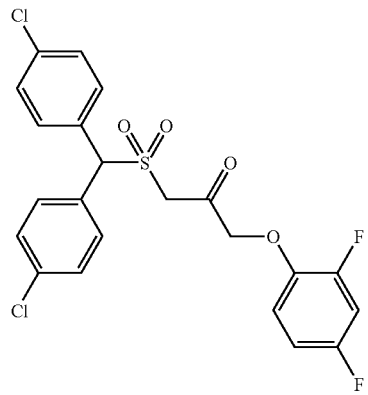

Step A: 1-[Bis-(4-chloro-phenyl)-methylsulfanyl]-3-(2,4-difluoro-phenoxy)-propan-2-ol

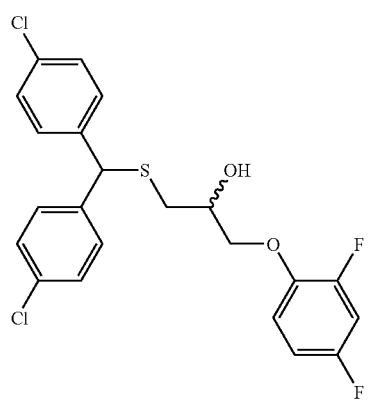

Prepared from bis-(4-chloro-phenyl)-methanethiol (2.4 g, 9.0 mmol) and 2-(2,4-difluoro-phenoxymethyl)-oxirane (2.0 g, 10.7 mmol) by the same method as described in Step A of Example 9. Purification by flash chromatography (silica gel, eluting with 70% dichloromethane in hexane) provided 3.3 g (81%) of product as an oil. MS (APCI-), m/z 453 (m−1); $^1$H NMR is consistent with the desired product structure.

Step B: 1-[Bis-(4-chloro-phenyl)-methylsulfanyl]-3-(2,4-difluoro-phenoxy)-propan-2-one

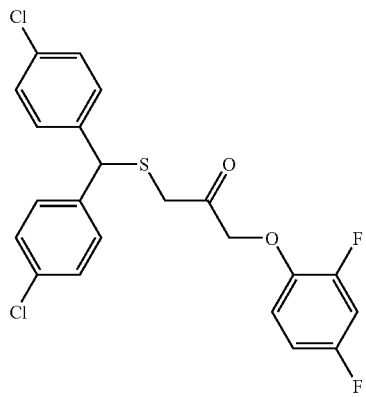

Prepared from 1-[bis-(4-chloro-phenyl)-methylsulfanyl]-3-(2,4-difluoro-phenoxy)-propan-2-ol (3.2 g, 7.0 mmol) by the same method as described in Step B of Example 9. Purification by flash chromatography (silica gel, eluting with 50% dichloromethane in hexane) afforded 2.0 g (62%) of product as a yellow solid with mp 76–78° C.; MS (APCI-), m/z 451 (m−1); $^1$H NMR is consistent with the desired product structure.

Step C: 1-[Bis-(4-chloro-phenyl)-methanesulfonyl]-3-(2,4-difluoro-phenoxy)-propan-2-one Prepared from 1-[bis-(4-chloro-phenyl)-methylsulfanyl]-3-(2,4-difluoro-phenoxy)-propan-2-one (1.8 g, 4.0 mmol) by the same method as described in Step C of Example 9. Purification by flash chromatography (silica gel, eluting with 20% ethyl acetate in hexane) afforded 0.74 g (38%) of product as an off-white solid with mp 54–56° C.; MS (APCI-), m/z 483 (m−1); $^1$H NMR is consistent with the desired product structure.

Example 14

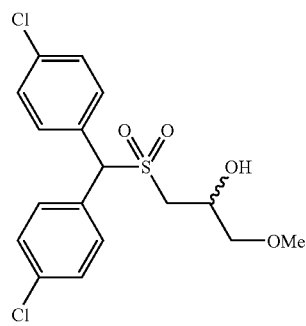

Step A: 1-[Bis-(4-chloro-phenyl)-methylsulfanyl]-3-methoxy-propan-2-ol

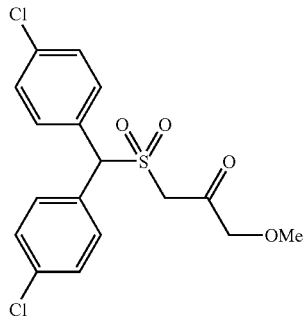

Prepared from bis-(4-chloro-phenyl)-methanethiol (2.0 g, 7.4 mmol) and 2-methoxymethyl-oxirane (0.55 g, 6.2 mmol) by the same method as described in Step A of Example 9. Purification by flash chromatography (silica gel, eluting with 30% ethyl acetate in hexane) provided 1.7 g (66%) of product as a green oil. MS (APCI-), m/z 355 (m−1); $^1$H NMR is consistent with the desired product structure.

Step B: 1-[Bis-(4-chloro-phenyl)-methanesulfonyl]-3-methoxy-propan-2-ol

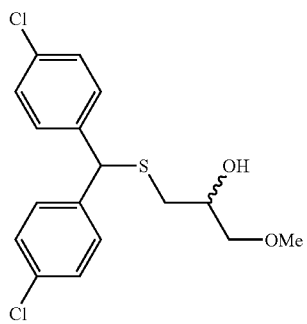

Prepared from 1-[bis-(4-chloro-phenyl)-methylsulfanyl]-3-methoxy-propan-2-ol (0.50 g, 1.4 mmol) by the same method as described in Step C of Example 9. Purification by flash chromatography (silica gel, eluting with 40% ethyl acetate in hexane) afforded 0.51 g (94%) of product as a white solid with mp 124–125° C. MS (APCI-), m/z 387 (m−1); $^1$H NMR is consistent with the desired product structure.

Step C: 1-[Bis-(4-chloro-phenyl)-methanesulfonyl]-3-methoxy-propan-2-one

To a solution of 1-[bis-(4-chloro-phenyl)-methanesulfonyl]-3-methoxy-propan-2-ol (0.80 g, 2.1 mmol) in 20 mL of dichloromethane was added molecular sieves (NMO, 4 angstroms), 4-methylmorpholine 4-oxide (0.42 g, 3.1 mmol), followed by tetrapropylammonium perruthenate (TPAP, 0.14 g, 0.41 mmol). The reaction mixture was stirred at room temperature for 18 hours and then the mixture was filtered through Celite filter aid. The filtrate was evaporated to give a residue, which was flash chromatographed (silica gel, 40% ethyl acetate in hexane) to provide 0.12 g (14%) of product as a tacky white solid. MS (APCI-), m/z 385 (m−1); $^1$H NMR is consistent with the desired product structure.

Example 15

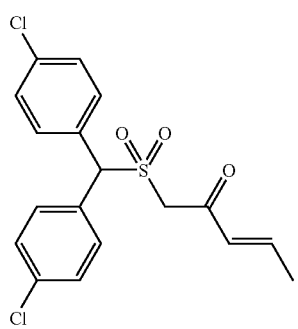

Step A: 1-[Bis-(4-chloro-phenyl)-methylsulfanyl]-pent-3-ene-2-one

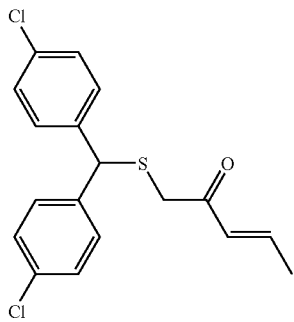

Prepared from 1-[bis-(4-chloro-phenyl)-methylsulfanyl]-N-methoxy-N-methyl-acetamide (4.2 g, 11.3 mmol) and 45 mL (1 Molar in diethyl ether) of allyl magnesium bromide (45 mmol) by the same procedure as described in Example 1, Step B. Purification by flash chromatography (silica gel, eluting with 50% ethyl acetate in hexane) provided 1.5 g (37%) of product as a yellow oil. MS (APCI-), m/z 349 (m–1); $^1$H NMR is consistent with the desired product structure.

Step B: 1-[Bis-(4-chloro-phenyl)-methanesulfonyl]-pent-3-ene-2-one

Prepared from 1-[bis-(4-chloro-phenyl)-methylsulfanyl]-pent-3-ene-2-one (1.1 g, 3.2 mmol) by the same method as described in Step C of Example 9. Purification by flash chromatography (silica gel, eluting with dichloromethane) afforded 0.79 g (64%) of product as a white solid with. A sample recrystallized from ethyl acetate/hexane had mp 114–116° C.; MS (APCI-), m/z 381 (m–1); $^1$H NMR is consistent with the desired product structure.

Example 16

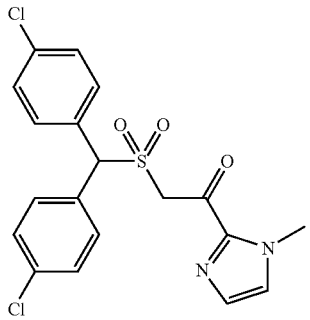

Step A: 2-[Bis-(4-chloro-phenyl)-methylsulfanyl]-1-(1-methyl-1H-imidazol-2-yl)-ethanone

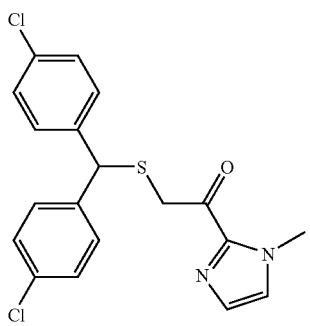

Prepared from bis-(4-chloro-phenyl)-methanethiol (3.9 g, 14.6 mmol) and 2-bromoacetyl-1-methylimidazole hydrobromide (Koike Hiroki et al., WO 99/35130 and H. McKennis et al., *JOC* 1963; 28:383, 16.1 mmol, containing an unspecified amount of pyridine hydrobromide) by the same procedure described for the formation of 5-(2-[bis-(4-chloro-phenyl)-methylsulfanyl]-acetyl)-thiophene-2-carboxylic acid dimethylamide (PD 0337179) the title compound of Example 17. Purification by flash chromatography (silica gel, 30% ethyl acetate in hexane) provided 4.6 g (80%) of product as a yellow-green oil. MS (APCI-), m/z 389 (m–1); $^1$H NMR is consistent with the desired product structure.

Step B: 2-[Bis-(4-chloro-phenyl)-methanesulfonyl]-1-(1-methyl-1H-imidazol-2-yl)-ethanone Prepared from 2-[Bis-(4-chloro-phenyl)-methylsulfanyl]-1-(1-methyl-1H-imidazol-2-yl)-ethanone (3.9 g, 10 mmol) by the same method as described in Step C of Example 9. Purification by flash chromatography (silica gel, eluting with 50% ethyl acetate in hexane, followed by 70% ethyl acetate in hexane) afforded 2.8 g (67%) of product as a white solid with mp 160–161° C. MS (APCI-), m/z 421 (m–1); $^1$H NMR is consistent with the desired product structure.

Example 17

5-(2-[Bis-(4-chloro-phenyl)-methylsulfanyl]-acetyl)-thiophene-2-carboxylic acid dimethylamide

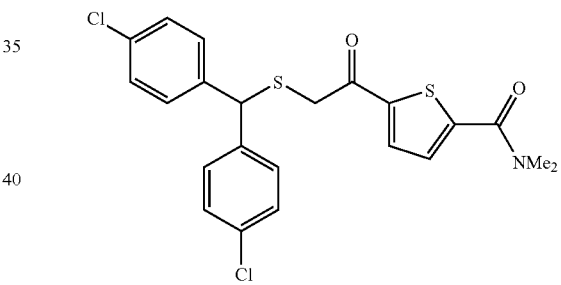

A solution of bis-(4-chloro-phenyl)-methanethiol (Fukuda, *Yakugaku Zasshi* 1952; 72:1472; 1.2 g, 4.5 mmol) and 5-(2-bromo-acetyl)-thiophene-2-carboxylic acid dimethylamide (Oxford A. W., Bradshaw J., and Coates I. H., U.S. Pat. No. 4,316,907; 1.4 g, 5.1 mmol) in 20 mL of acetonitrile was cooled in ice and treated slowly with 1,8-diazabicyclo[5.4.0]undec-7-ene (DBU; 0.75 mL, 0.76 g, 5.0 mmol), and the mixture was stirred at room temperature for 18 hours. The reaction mixture was added to 300 mL of brine, and the new mixture was extracted with four 100 mL portions of ethyl acetate. The combined organic layers were washed with two 250 mL portions of brine. The organic layer was dried (sodium sulfate) and evaporated. The residue was purified by chromatography (eluting with 1:1 ethyl acetate/hexane followed by 2:1 ethyl acetate/hexane plus 1% methanol) to yield 1.1 g (52%) of product. A sample recrystallized from ethyl acetate/hexane had mp 150–151° C.; MS (APCI-), m/z 464; $^1$H NMR consistent with desired product structure.

Example 18

5-(2-[Bis-(4-chloro-phenyl)-methanesulfonyl]-acetyl)-thiophene-2-carboxylic acid dimethylamide

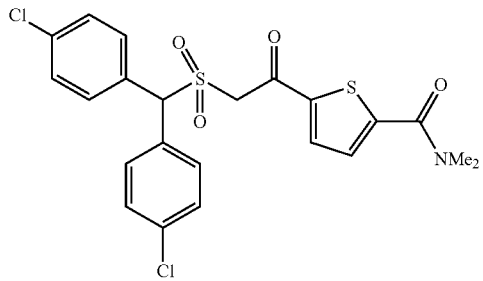

A solution of 5-(2-[bis-(4-chloro-phenyl)-methylsulfanyl]-acetyl)-thiophene-2-carboxylic acid dimethylamide (0.90 g, 1.9 mmol) in 40 mL of dichloromethane was cooled in ice and treated in portions with 3-chloroperoxybenzoic acid (2.0 g of 70%, 8.1 mmol), and the mixture was stirred at room temperature for 18 hours. The reaction mixture was diluted with an additional 150 mL of fresh dichloromethane, and the new mixture was washed with one 150 mL portion of saturated aqueous sodium bisulfite solution, four 200 mL portions of 5% aqueous potassium carbonate solution, and one 200 mL portion of brine. The organic layer was dried (sodium sulfate) and evaporated. The residue was purified by chromatography (eluting with 2:1 ethyl acetate/hexane) to yield 0.80 g (83%) of product. A sample recrystallized from ethyl acetate/hexane had mp 192–194° C.; MS (APCI-), m/z 496; $^1$H NMR consistent with desired product structure.

Example 19

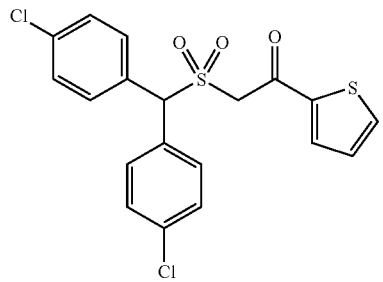

Step A: 2-[Bis-(4-chloro-phenyl)-methylsulfanyl]-1-thiophen-2-yl-ethanone

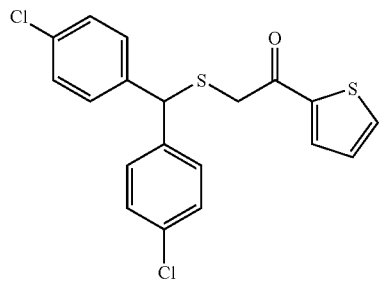

Prepared in 81% yield from bis-(4-chloro-phenyl)-methanethiol and 2-bromo-1-thiophen-2-yl-ethanone (Bagli J. F., Ferdinandi E. *Can. J. Chem.*, 1975; 53:2598) by the procedure described in Example 17. The crude product was purified by chromatography (eluting with 1:1 ethyl acetate/hexane). A sample recrystallized from hexane had mp 93–94° C.; MS (APCI-), m/z 393; $^1$H NMR consistent with desired product structure.

Step B: 2-[Bis-(4-chloro-phenyl)-methanesulfonyl]-1-thiophen-2-yl-ethanone

A suspension of 2-[bis-(4-chloro-phenyl)-methylsulfanyl]-1-thiophen-2-yl-ethanone (2.0 g, 5.1 mmol) in 20 mL of glacial acetic acid was treated slowly with 3.0 mL (26.4 mmol) of 30% aqueous hydrogen peroxide solution, and the mixture was stirred at room temperature for 2 hours. An additional 10 mL of acetic acid was added, followed by 3.0 mL (26.4 mmol) of fresh 30% aqueous hydrogen peroxide solution. The reaction mixture was stirred at room temperature for 72 hours and added in portions to 500 mL of cold saturated sodium bisulfite solution. The new mixture was extracted with four 150 mL portions of ethyl acetate. The combined organic layers were washed with one 300 mL portion of brine, four 300 mL portions of 5% aqueous sodium bicarbonate solution, and brine again. The organic layer was dried (sodium sulfate) and evaporated. The residue was purified by chromatography (eluting with 1:3 ethyl acetate/hexane) to yield 1.5 g (68%) of product. A sample recrystallized from ethyl acetate/hexane had mp 150–151° C.; MS (APCI-), m/z 425; $^1$H NMR consistent with desired product structure.

Example 20

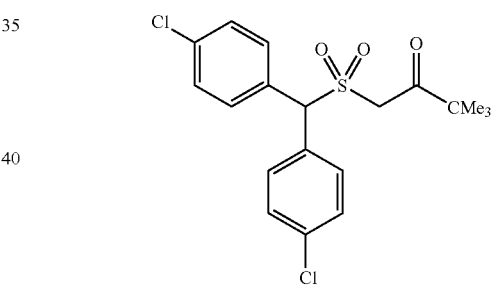

Step A: 1-[Bis-(4-chloro-phenyl)-methylsulfanyl]-3,3-dimethyl-butan-2-one

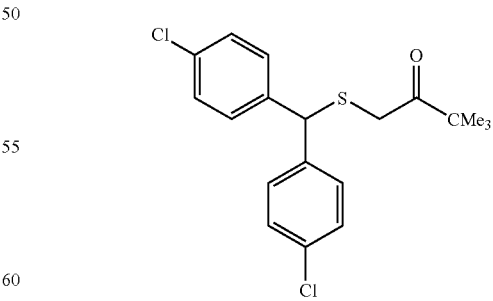

Prepared as an oil in 65% yield from bis-(4-chlorophenyl)-methanethiol and 1-bromo-3,3-dimethyl-butan-2-one by the procedure described in Example 17. The crude product was purified by chromatography (eluting with 5:95 ethyl acetate/hexane); MS (APCI-), m/z 367; $^1$H NMR consistent with desired product structure.

Step B: 1-[Bis-(4-chloro-phenyl)-methanesulfonyl]-3,3-dimethyl-butan-2-one

A solution of 1-[bis-(4-chloro-phenyl)-methylsulfanyl]-3,3-dimethyl-butan-2-one (2.2 g, 6.0 mmol) in 40 mL of dichloromethane was cooled in ice and treated in portions with 3-chloroperoxybenzoic acid (4.5 g of 70%, 18.3 mmol), and the mixture was stirred at room temperature for 18 hours. The reaction mixture was filtered, and the insoluble material was washed several times on the funnel with fresh dichloromethane. The combined filtrates were diluted with an additional 150 mL of fresh dichloromethane. The new solution was washed with one 150 mL portion of saturated aqueous sodium bisulfite solution, four 200 mL portions of 5% aqueous potassium carbonate solution, and one 200 mL portion of brine. The organic layer was dried (sodium sulfate) and evaporated. The residue was purified by chromatography (eluting with 1:9 ethyl acetate/hexane) to yield 2.0 g (83%) of product; mp 128–130° C.; MS (APCI-), m/z 399; $^1$H NMR consistent with desired product structure.

Example 21

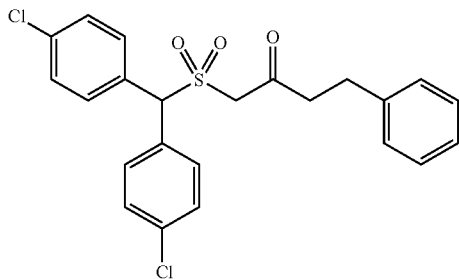

Step A: 1-[Bis-(4-chloro-phenyl)-methylsulfanyl]-4-phenyl-butan-2-one

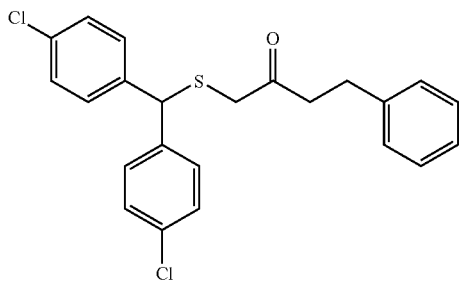

Prepared as an oil in 52% yield from bis-(4-chloro-phenyl)-methanethiol and 1-bromo-4-phenyl-butan-2-one (Moinet C., Sackur C., and Thurieau C., WO 0107424) by the procedure described in Example 17. The crude product was purified by chromatography (eluting with 1:9 ethyl acetate/hexane); MS (APCI-), m/z 415; $^1$H NMR consistent with desired product structure.

Step B: 1-[Bis-(4-chloro-phenyl)-methanesulfonyl]-4-phenyl-butan-2-one

Prepared in 83% yield from 1-[bis-(4-chloro-phenyl)-methylsulfanyl]-4-phenyl-butan-2-one and 3-chloroperoxybenzoic acid by the procedure described in Example 20. The crude product was purified by chromatography (eluting with 15:85 ethyl acetate/hexane). A sample recrystallized from ethyl acetate/hexane had mp 106–107° C.; MS (APCI-), m/z 447; $^1$H NMR consistent with desired product structure.

Example 22

4-[Bis-(4-chloro-phenyl)-methanesulfonyl]-3-oxo-butyric acid methyl ester

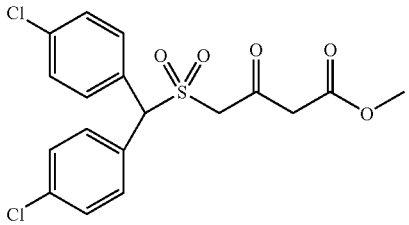

Step A: 4-[Bis-(4-chloro-phenyl)-methylsulfanyl]-3-oxo-butyric acid methyl ester

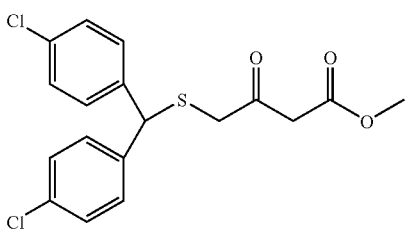

To a mixture of bis-(4-chloro-phenyl)-methanethiol prepared according to the reference[1] (500 mg, 1.86 mmol) in dry THF (20 mL) was added triethylamine (0.39 mL, 2.75 mmol) in an ice-bath under a nitrogen atmosphere. The mixture was stirred for 10 minutes and then 4-chloro-3-oxo-butyric acid methyl ester (0.22 mL, 1.86 mmol) was added dropwise. The resulting mixture was stirred at room temperature for 30 minutes. TLC indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–15% ethyl acetate in hexanes) to give 640 mg (90%) of the desired product as a colorless syrup: $^1$H NMR (400 MHz, DMSO-6d): δ 3.36 (s, 2H, CH$_2$), 3.55 (s, 3H, CH$_3$), 3.63 (s, 2H, CH$_2$), 5.23 (s, 1H, CH), 7.36 (s, 8H, ArH); MS(APCI-): m/z 381.1 (M–H); Anal. Calcd for C$_{18}$H$_{16}$Cl$_2$O$_3$S$_1$.0.1CH$_2$Cl$_2$: C, 55.49; H, 4.17; Cl, 19.91; S, 8.18. Found: C, 55.50; H, 4.16; Cl, 19.62; S, 8.12.

Step B: 4-[Bis-(4-chloro-phenyl)-methanesulfonyl]-3-oxo-butyric acid methyl ester To a solution of 4-[bis-(4-chloro-phenyl)-methylsulfanyl]-3-oxo-butyric acid methyl ester prepared from Step A (550 mg, 1.43 mmol) in methylene chloride (20 mL) was added mCPBA (743 mg, 4.3 mmol) in portions in an ice-bath under a nitrogen atmosphere. The mixture was stirred at room temperature for 1 hour. TLC and MS indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–18% ethyl acetate in hexanes) to give 300 mg (50%) of the desired product as a white foam: mp 76–78° C.; $^1$H NMR (400 MHz, DMSO-6d): δ 3.55 (s, 3H, CH$_3$), 3.66 (s, 2H, CH$_2$), 4.35 (s, 2H, CH$_2$), 6.04 (s, 1H, CH), 7.46–7.61 (m, 8H, ArH); MS(APCI-): m/z 413.1 (M–H); Anal. Calcd for C$_{18}$H$_{16}$Cl$_2$O$_5$S$_1$: C, 52.06; H, 3.88; S, 7.72. Found: C, 52.22; H, 3.96; S, 7.36.

Example 23

4-[Bis-(4-chloro-phenyl)-methanesulfonyl]-N-(2-chloro-phenyl)-3-oxo-butyramide

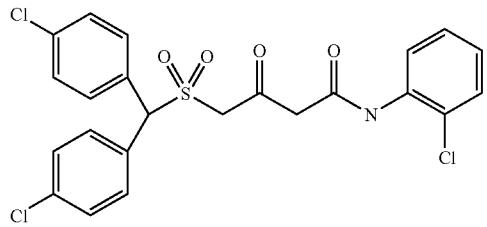

Step A: 4-[Bis-(4-chloro-phenyl)-methylsulfanyl]-N-(2-chloro-phenyl)-3-oxo-butyramide

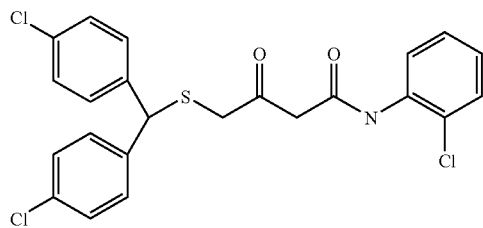

To a mixture of bis-(4-chloro-phenyl)-methanethiol prepared according to the reference[1] (500 mg, 1.86 mmol) in dry THF (20 mL) was added triethylamine (0.39 mL, 2.75 mmol) in an ice-bath under a nitrogen atmosphere. The mixture was stirred for 10 minutes and then 2',4-dichloro-acetoacetanilide (460 mg, 1.86 mmol) was added. The resulting mixture was stirred at room temperature for 1 hour. TLC indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–15% ethyl acetate in hexanes) to give 822 mg (92%) of the desired product as a colorless syrup: $^1$H NMR (400 MHz, DMSO-6d): δ 3.42 (s, 2H, CH$_2$), 3.70 (s, 2H, CH$_2$), 5.27 (s, 1H, CH), 7.11–7.72 (m, 12H, ArH), 9.68 (s, 1H, NH); MS(APCI-): m/z 476.1 (M–H); Anal. Calcd for C$_{23}$H$_{18}$Cl$_3$N$_1$O$_2$S$_1$: C, 57.69; H, 3.79; N, 2.93; S, 6.70. Found: C, 58.07; H, 4.17; N, 2.70; S, 6.42.

Step B: 4-[Bis-(4-chloro-phenyl)-methanesulfonyl]-N-(2-chloro-phenyl)-3-oxo-butyramide To a solution of 4-[bis-(4-chloro-phenyl)-methylsulfanyl]-N-(2-chloro-phenyl)-3-oxo-butyramide prepared from Step A (720 mg, 1.5 mmol) in methylene chloride (30 mL) was added mCPBA (780 mg, 4.5 mmol) in portions in an ice-bath under a nitrogen atmosphere. The mixture was stirred at room temperature for 1 hour. TLC and MS indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–20% ethyl acetate in hexanes) to give 320 mg (42%) of the desired product as a yellowish solid: mp 92–95° C.; $^1$H NMR (400 MHz, DMSO-6d): δ 3.73 (s, 2H, CH$_2$), 4.39 (s, 2H, CH$_2$), 6.07 (s, 1H, CH), 7.13–7.71 (m, 12H, ArH), 9.68 (s, 1H, NH); MS(APCI-): m/z 508.1 (M–H); Anal. Calcd for C$_{23}$H$_{18}$Cl$_3$N$_1$O$_4$S$_1$.0.2Et$_2$O: C, 54.38; H, 3.84; N, 2.66. Found: C, 54.63; H, 3.73; N, 2.57.

Example 24

4-[Bis-(4-chloro-phenyl)-methanesulfonyl]-butan-2-one

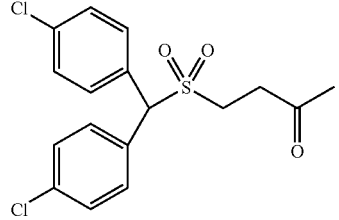

Step A: 4-[Bis-(4-chloro-phenyl)-methylsulfanyl]-butan-2-one

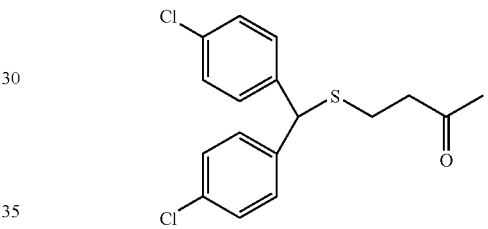

To a mixture of bis-(4-chloro-phenyl)-methanethiol prepared according to the reference (Fukuda, *Yakugaku Zasshi* 1952; 72:1472; Chem. Abstr., 1953:8706) (500 mg, 1.86 mmol) in ethanol (20 mL) was added potassium tert-butoxide (208 mg, 1.86 mmol) in an ice-bath under a nitrogen atmosphere. The mixture was stirred for 10 minutes and then methyl vinyl ketone (0.31 mL, 3.72 mmol) was added dropwise. The resulting mixture was stirred at room temperature for 30 minutes. TLC indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–15% ethyl acetate in hexanes) to give 510 mg (81%) of the desired product as a colorless syrup: $^1$H NMR (400 MHz, DMSO-6d): δ 1.99 (s, 3H, CH$_3$), 2.41 (t, J=7.1 Hz, 2H, CH$_2$), 2.65 (t, J=7.1 Hz, 2H, CH$_2$), 5.37 (s, 1H, CH), 7.33–7.39 (m, 8H, ArH); MS(APCI-): m/z 337.0 (M–H); Anal. Calcd for C$_{17}$H$_{16}$Cl$_2$O$_1$S$_1$: C, 60.18; H, 4.75; S, 9.45. Found: C, 60.06; H, 4.63; S, 9.35.

Step B: 4-[Bis-(4-chloro-phenyl)-methanesulfonyl]-butan-2-one

To a solution of 4-[bis-(4-chloro-phenyl)-methylsulfanyl]-butan-2-one prepared from Step A (400 mg, 1.18 mmol) in methylene chloride (20 mL) was added mCPBA (611 mg, 3.54 mmol) in portions in an ice-bath under a nitrogen atmosphere. The mixture was stirred at room temperature for 1 hour. TLC and MS indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (5%–35% ethyl acetate in hexanes) to give 320 mg (73%) of the desired product as a white solid: mp 103–105° C.; $^1$H NMR (400 MHz, DMSO-6d): δ 2.05 (s, 3H, CH$_3$), 2.82 (t, J=7.4 Hz, 2H, CH$_2$), 3.05 (t, J=7.4 Hz, 2H, CH$_2$), 6.10 (s, 1H, CH), 7.45–7.62 (m, 8H, ArH); MS(APCI-): m/z 369.1 (M–H); Anal. Calcd for C$_{17}$H$_{16}$Cl$_2$O$_3$S$_1$: C, 54.99; H, 4.34; S, 8.64. Found: C, 54.97; H, 4.26; S, 8.66.

Example 25

Acetic acid 3-[bis-(4-chloro-phenyl)-methanesulfonyl]-2-oxo-propyl ester

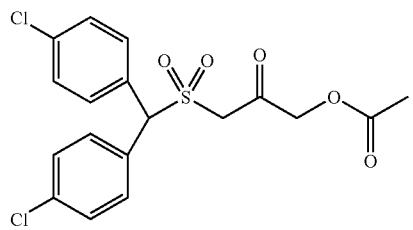

Step A: Acetic acid 3-[bis-(4-chloro-phenyl)-methylsulfanyl]-2-oxo-propyl ester

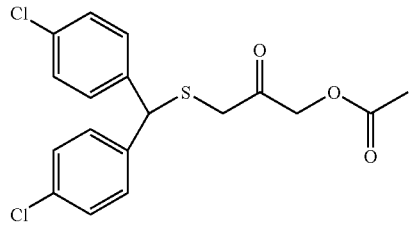

To a mixture of bis-(4-chloro-phenyl)-methanethiol prepared according to the reference (Fukuda: *Yakugaku Zasshi;* 1952; 72:1472; Chem. Abstr., 1953:8706) (2 g, 7.43 mmol) in dry THF (30 mL) was added triethylamine (1.03 mL, 7.43 mmol) in an ice-bath under a nitrogen atmosphere. The mixture was stirred for 10 minutes and then 1-acetoxy-3-chloroacetone (1.12 g, 7.43 mmol) was added dropwise. The resulting mixture was stirred at room temperature for 30 minutes. TLC indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–10% ethyl acetate in hexanes) to give 2.65 g (93%) of the desired product as a colorless syrup: $^1$H NMR (400 MHz, DMSO-6d): δ 2.04 (s, 3H, CH$_3$), 3.28 (s, 2H, CH$_2$), 4.80 (s, 2H, CH$_2$), 5.26 (s, 1H, CH), 7.36 (s, 8H, ArH); MS(APCI-): m/z 381.0 (M–H); Anal. Calcd for C$_{18}$H$_{16}$Cl$_2$O$_3$S$_1$: C, 56.41; H, 4.21; S, 8.37. Found: C, 56.19; H, 4.12; S, 8.08.

Step B: Acetic acid 3-[bis-(4-chloro-phenyl)-methanesulfonyl]-2-oxo-propyl ester To a solution of acetic acid 3-[bis-(4-chloro-phenyl)-methylsulfanyl]-2-oxo-propyl ester prepared from Step A (327 mg, 0.85 mmol) in methylene chloride (20 mL) was added mCPBA (442 mg, 2.56 mmol) in portions in an ice-bath under a nitrogen atmosphere. The mixture was stirred at room temperature for 1 hour. TLC and MS indicated that the reaction was complete. The mixture was partitioned between ethyl acetate and saturated NaHCO$_3$ solution. The organic phase was washed with water and brine, dried over Na$_2$SO$_4$, and filtered. The filtrate was concentrated in vacuo to give a residue, which was purified by chromatography (2%–25% ethyl acetate in hexanes) to give 255 mg (72%) of the desired product as a white foam: mp 57–60° C.; $^1$H NMR (400 MHz, DMSO-6d): δ 2.04 (s, 3H, CH$_3$), 4.33 (s, 2H, CH$_2$), 4.77 (s, 2H, CH$_2$), 6.02 (s, 1H, CH), 7.46–7.60 (m, 8H, ArH); MS(APCI-): m/z 413.0 (M–H); Anal. Calcd for C$_{18}$H$_{16}$Cl$_2$O$_5$S$_1$: C, 52.06; H, 3.88; S, 7.72. Found: C, 52.31; H, 3.91; S, 7.75.

Example 26

1-[Bis-(4-chloro-phenyl)-methanesulfonyl]-4,4,4-trifluoro-butan-2-one

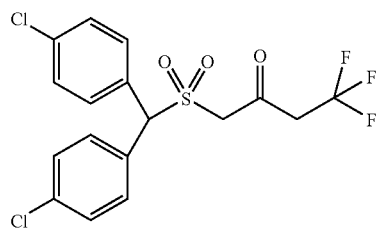

Step A: 1-[Bis-(4-chloro-phenyl)-methylsulfanyl]-4,4,4,-trifluoro-2-butanol

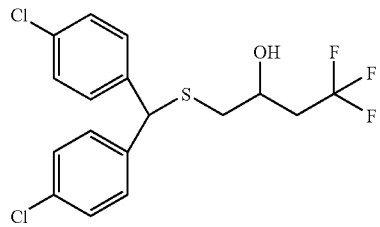

To a mixture of bis-(4-chloro-phenyl)-methanethiol prepared according to the reference (Fukuda, *Yakugaku Zasshi* 1952; 72:1472; Chem. Abstr., 1953:8706) (3 g, 11.1 mmol) in acetonitrile (50 mL) was added tetrabutylammonium fluoride (1.0 M solution in THF, 0.93 mL, 0.93 mmol) under a nitrogen atmosphere. The mixture was stirred at 45° C. for 5 minutes and then cooled down to the room temperature. To the resulting mixture was added 1,1,1-trifluoro-3,4-epoxybutane (1.2 g, 9.3 mmol). The mixture was stirred at room temperature for 1 day and partitioned between ethyl acetate and saturated NaHCO$_3$ solution. The organic phase was washed with water and brine, dried over Na$_2$SO$_4$ and filtered. The filtrate was concentrated in vacuo to give a residue, which was purified by chromatography (2%–15% ethyl acetate in hexanes) to give 2.79 g (76%) of the desired product as a syrup: $^1$H NMR (400 MHz, DMSO-6d): δ 2.17–2.44 (m, 2H, CH$_2$CF$_3$), 2.44 (d, J=2.0 Hz, 2H, CH$_2$), 3.81 (m, 1H, CH), 5.28 (d, J=6.1 Hz, 1H, OH), 5.42 (s, 1H, CH), 7.31–7.42 (m, 8H, ArH); MS(APCI-): m/z 393.1 (M–H).

Step B: 1-[Bis-(4-chloro-phenyl)-methylsulfanyl]-4,4,4-trifluoro-butan-2-one

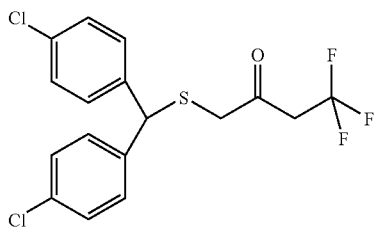

To a mixture of 1-[bis-(4-chloro-phenyl)-methylsulfanyl]-4,4,4,-trifluoro-2-butanol prepared from Step A (1.0 g, 2.53 mmol) in methylene chloride (50 mL) was added pyridinium dichromate (2.85 g, 7.59 mmol). The mixture was heated at reflux for 3 hours. TLC was showed that the reaction was complete. The mixture was filtered and the filtrate was partitioned between ethyl acetate and water. The organic phase was washed with water and brine, dried over $Na_2SO_4$, and filtered. The filtrate was concentrated in vacuo to give a residue, which was purified by chromatography (2%–8% ethyl acetate in hexanes) to give 400 mg (40%) of the desired product as a white foam: mp 56–58° C.; $^1$H NMR (400 MHz, DMSO-6d): δ 3.35 (s, 2H, $CH_2$), 3.75 (q, J=11.0 Hz, 2H, $CH_2CF_3$), 5.26 (s, 1H, CH), 7.35–7.39 (m, 8H, ArH); MS(APCI-): m/z 391.0 (M–H); Anal. Calcd for $C_{17}H_{13}Cl_2F_3O_1S_1$: C, 51.92; H, 3.33; S, 8.15. Found: C, 51.59; H, 3.05; S, 7.80.

Step C: 1-[Bis-(4-chloro-phenyl)-methanesulfonyl]-4,4,4-trifluoro-butan-2-one

To a solution of 1-[bis-(4-chloro-phenyl)-methylsulfanyl]4,4,4,-trifluoro-2-butanol prepared from Step B (358 mg, 0.91 mmol) in methylene chloride (20 mL) was added mCPBA (471 mg, 2.73 mmol) in portions in an ice-bath under a nitrogen atmosphere. The mixture was stirred at room temperature for 1 hour. TLC and MS indicated that the reaction was complete. The mixture was partitioned between ethyl acetate and saturated $NaHCO_3$ solution. The organic phase was washed with water and brine, dried over $Na_2SO_4$, and filtered. The filtrate was concentrated in vacuo to give a residue, which was purified by chromatography (2%–20% ethyl acetate in hexanes) to give 260 mg (67%) of the desired product as a white foam: mp 48–50° C.; $^1$H NMR (400 MHz, DMSO-6d): δ 3.77 (q, J=10.5 Hz, 2H, $CH_2CF_3$), 4.35 (s, 2H, $CH_2$), 6.07 (s, 1H, CH), 7.46–7.61 (m, 8H, ArH); MS(APCI-): m/z 423.0 (M–H); Anal. Calcd for $C_{17}H_{13}Cl_2F_3O_3S_1$: C, 48.02; H, 3.08; Cl, 16.67; S, 7.54. Found: C, 48.15; H, 2.99; Cl, 16.34; S, 7.55.

Example 27

1-[Bis-(4-chloro-phenyl)-methanesulfonyl]-3-phenylmethanesulfonyl-propan-2-one

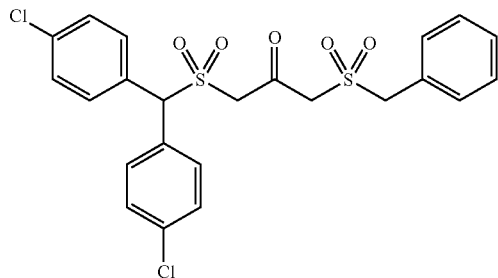

Step A: 1-Benzylsulfanyl-3-[bis-(4-chloro-phenyl)-methanesulfonyl]-propan-2-one

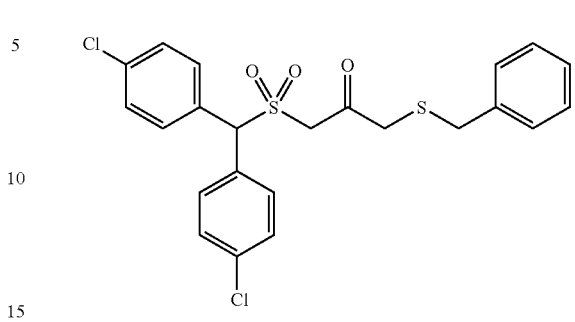

To a solution of 1-[bis-(4-chloro-phenyl)-methanesulfonyl]-3-bromo-propan-2-one (Example 3, 2.24 g, 5.14 mmol) in dry THF (30 mL) cooled in an ice-bath was added triethylamine (0.788 mL, 5.65 mmol) and followed by phenyl-methanethiol (0.603 mL, 5.14 mmol) under a nitrogen atmosphere. The mixture was stirred for 30 minutes, then diluted with EtOAc. The mixture was washed successively with HCl solution (1N), aqueous $NaHCO_3$ (saturated), and brine, dried over $Na_2SO_4$, and filtered. The filtrate was concentrated in vacuo to give a residue, which was purified by chromatography (5%–20% ethyl acetate in hexanes) and crystallization from EtOAc/hexanes to give 1.60 g (65%) of the desired product as white crystals: MS(APCI-): m/z 477.0 (M–H); mp 108–110° C.

Step B:

To a solution of 1-benzylsulfanyl-3-[bis-(4-chloro-phenyl)-methanesulfonyl]-propan-2-one prepared from Step A (488 mg, 1.02 mmol) in methylene chloride (20 mL) cooled in an ice-bath was added mCPBA (502 mg, 2.04 mmol) in portions. The mixture was stirred at room temperature for 1 hour. TLC and MS indicated that the reaction was complete. The mixture was partitioned between ethyl acetate and saturated $NaHCO_3$ solution. The organic phase was washed with water and brine, dried over $Na_2SO_4$, and filtered. The filtrate was concentrated in vacuo to give a residue, which was purified by chromatography (10%–25% ethyl acetate in hexanes) to give 230 mg (44%) of the desired product as a white foam: mp 72–90° C.; MS(APCI-): m/z 509.0 (M–H).

Example 28

3-[Bis(4-fluorophenyl)methanesulfonyl]-1,1,1-trifluoropropane-2,2-diol

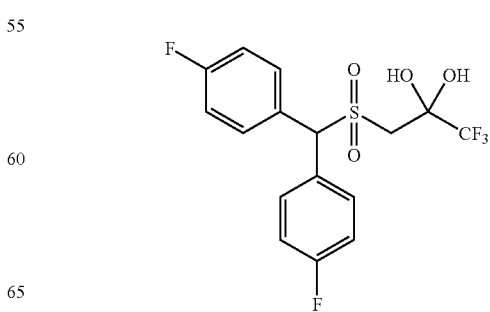

Step A: Bis(4-fluorphenyl)methanethiol

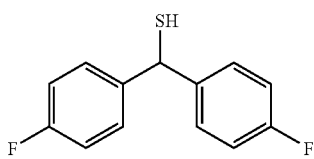

To a slurry of Lawesson's reagent (2.3 g, 5.5 mmol) in DME (50 mL) under nitrogen atmosphere was added 4,4'-difluorobenhydrol (2.2 g, 10 mmol). The resulting mixture was stirred until clear then warmed to reflux and refluxed 4 hours. After cooling, the reaction mixture was concentrated under reduced pressure and the residue purified by flash chromatography on silica gel (EtOAc/Hexane, 1:10) to obtain 1.32 g (56%) of the title compound as a clear oil. $^1$H NMR (CDCl$_3$) δ 2.26 (d, J=5.1 Hz, 1H), 5.41 (d, J=4.9 Hz, 1H), 6.95–7.05 (m, 4H), 7.3–7.36 (m, 4H). MS 235 (M–1).

Step B: 3-[Bis(4-fluorophenyl)methyl sulfanyl]-1,1,1-trifluoropropane-2,2-diol

To a solution of the thiol from Step A (1.2 g, 5.0 mmol) in dichloromethane (20 mL) under a nitrogen atmosphere and cooled in an ice-bath was added 3-bromo-1,1,1-trifluoroacetone (0.55 mL, 5.4 mmol) followed by triethylamine (0.75 m]L, 5.4 mmol) dropwise. The resulting mixture was stirred 1 hour, warmed to room temperature, and stirred 16 hours. The reaction mixture was diluted with dichloromethane (100 mL), then washed with 2N HCl and brine. The organic phase was dried over MgSO$_4$, filtered, and concentrated under reduced pressure. The residue was purified by flash chromatography on silica gel (EtOAc/Hexane, 1:9) to give 1.6 g (91%) of a light brown oil. $^1$H NMR δ 2.72 (s, 2H), 3.89 (s, 2H), 7.00–7.15 (m, 4H), 7.33–7.40 (m, 4H). MS 445 (M–1).

Step C: To a solution of the sulfide (1.6 g, 4.5 mmol) in glacial acetic acid (7.0 mL) was added 30% hydrogen peroxide solution (4 mL) slowly. The resulting mixture was stirred 6 hours, diluted with water (75 mL), and extracted with EtOAc. The combined extracts were washed with water and brine then the organic phase was dried over MgSO$_4$, and concentrated under reduced pressure. The residue was purified by flash chromatography on silica gel (EtOAc/Hexane, 1:9) to give 0.51 g (29%) of the title product and 0.68 g (40%) of the sulfinyl analog. $^1$H NMR δ 3.25 (s, 2H), 4.94 (s, 2H), 5.93 (s, 1H), 7.09–7.16 (m, 4H), 7.59–7.64 (m, 4H). MS 377 (M–1).

Example 29

3-[Bis(4-trifluoromethyl-phenyl)methanesulfonyl]-1,1,1-trifluoropropane-2,2-diol

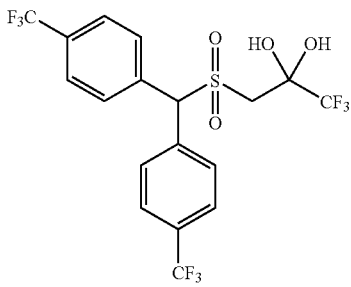

Step A: Bis(4-trifluoromethyl-phenyl)methanol

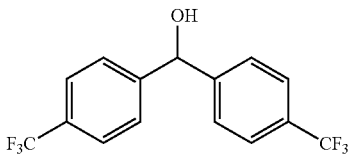

To magnesium turnings (0.93 g, 38 mmol) in ether (60 mL) under nitrogen atmosphere was added 4-bromobenzotrifluoride (0.5 g, 2 mmol) while stirring vigorously, a few drops of iodomethane were added to initiate the reaction. After the reaction was initiated, 4-bromobenzotrifluoride (4.5 g, 20 mmol) was added slowly over 45 minutes at a rate to maintain the reaction. After the addition was complete, the resulting mixture was stirred 2 hours then α,α,α-trifluorotoluene (3.5 g, 20 mmol) was added dropwise. The reaction mixture was stirred 1 hour, carefully quenched with 2N HCl, and diluted with ether (100 mL). The organic phase was washed with saturated aqueous NaHCO$_3$ and brine, dried over MgSO$_4$, then concentrated under reduced pressure. The residue was purified by chromatography on silica gel (EtOAc/Hexane, 1:20) to give 4.6 g (49%) of a white solid. $^1$H NMR CDCl$_3$ δ 2.37 (d, J=3.4 Hz, 1H), 5.94 (d, J=2.4 Hz, 1H), 7.25–7.62 (dd, J=8.1 and 44.4 Hz, 8H). MS 319 (M–1). Anal. (C$_{15}$H$_{10}$F$_6$O) C, H, N.

Step B: Chloro-bis(4-trifluoromethyl-phenyl)methane

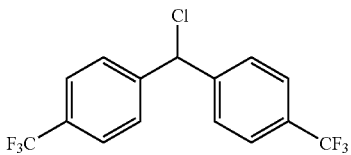

To a solution of bis(4-trifluoromethyl-phenyl)methanol (4.5 g, 14 mmol) in toluene (15 mL) under nitrogen atmosphere was added thionyl chloride (1.6 mL, 22 mmol). The resulting mixture was refluxed 2 hours then concentrated under reduced pressure. The residue was purified by flash chromatography on silica gel (EtOAc/Hexane, 1:20) to give 4.1 g (87%) of a pale yellow oil. $^1$H NMR CDCl$_3$ δ 6.16 (s, 1H), 7.50–7.54 (m, 4H), 7.60–764 (m, 4H). MS 337 (M–1).

Step C: Chloro-bis(4-trifluoromethyl-phenyl)methanethiol

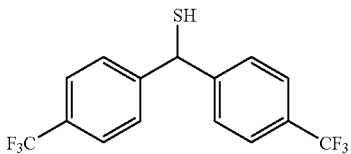

To a solution of the chloride (4.0 g, 12 mmol) in Ethanol (20 mL) was added Thiourea (1.6 g, 12 mmol). The resulting mixture was warmed to reflux, refluxed 2 hours, cooled lightly, and 50% NaOH (1.5 g, 19 mmol) in H$_2$O (4 mL) added. After refluxing an additional 2 hours, the reaction mixture was acidified with 2N HCl and extracted with EtOAc. The combined extracts were washed with H$_2$O and brine, then the organic phase was dried over MgSO$_4$ and concentrated under reduced pressure. The residue was purified by flash chromatography on silica gel (EtOAc/Hexane, 1:9) to give 3.3 g (82%) of a pale yellow oil. $^1$H NMR CDCl$_3$ δ 2.32 (d, J=5.4 Hz, 1H), 5.49 (d, J=5.4 Hz, 1H), 7.49–752 (m, 4H), 7.56–762 (m, 4H). MS 335 (M–1).

Step D: 3-[Bis(4-trifluoromethyl-phenyl)methylsulfanyl]-1,1,1-trifluoropropane-2,2-diol To a solution of the thiol (3.0 g, 8.9 mmol) in dichloromethane (25 mL) under a nitrogen atmosphere and cooled in an ice-bath was added 3-bromo-1,1,1-trifluoroacetone (1.0 mL, 9.1 mmol) followed by triethylamine (1.3 mL, 9.3 mmol) dropwise. The resulting mixture was stirred 1 hour, warmed to room temperature, and stirred 16 hours. The reaction mixture was diluted with dichloromethane (100 mL), then washed with 2N HCl and brine. The organic phase was dried over MgSO$_4$, filtered, and concentrated under reduced pressure. The residue was purified by flash chromatography on silica gel (EtOAc/Hexane, 1:9) to give 1.6 g (91%) of a clear oil which solidified on standing. $^1$H NMR δ 2.76 (s, 2H), 3.86 (s, 2H), 5.71 (s, 1H), 7.51–7.63 (m, 8H). MS 445 (M–H$_2$O).

Step E: To a solution of the sulfide (2.5 g, 5.6 mmol) in glacial acetic acid (7.0 mL) was added 30% hydrogen peroxide solution (4 mL) slowly. The resulting mixture was stirred 16 hours, diluted with water (75 mL), and extracted with EtOAc. The combined extracts were washed with water and brine, then the organic phase was dried over MgSO$_4$ and concentrated under reduced pressure. The residue was purified by flash chromatography on silica gel (EtOAc/Hexane, 1:9) to give 1.6 g (57%) of the title product. $^1$H NMR δ 3.29 (s, 2H), 4.91 (s, 2H), 6.10 (s, 1H), 7.09–7.30 (m, 4H), 7.70–7.80 (m, 4H). MS 477 (M–H$_2$O). Anal. (C$_{18}$H$_{13}$F$_9$O$_4$S) C, H, N.

Example 30

3-[(4-Chlorophenyl)-(3,4-dichlorophenyl)methanesulfonyl]-1,1,1-trifluoropropane-2,2-diol

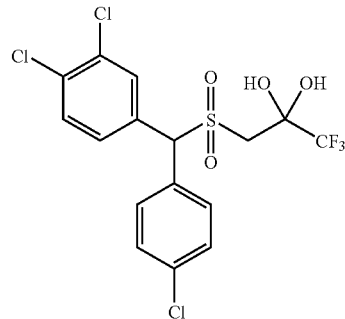

Step A: (4-Chlorophenyl)-(3,4-dichlorophenyl)methanol

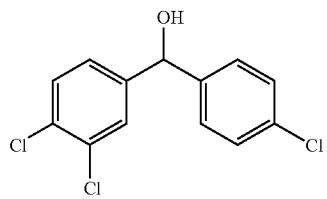

To a solution of 3,4-dichlorobenzaldehyde (5.3 g, 30 mmol) in dry Ether (50 mL) under nitrogen atmosphere cooled in an ice-bath was added a 1 M solution of 4-chlorophenylmagnesium bromide in Ether (33 mL, 33 mmol) dropwise. The resulting mixture was stirred 0.5 hours, warmed to room temperature, stirred 2 hours, warmed to reflux, and refluxed 2 hours. After cooling to room temperature, the reaction mixture was quenched by the careful addition of 2N HCl, diluted with ether (100 mL) and washed with brine. The organic phase was dried over MgSO$_4$ and concentrated under reduced pressure. The residue was purified by flash chromatography (EtOAc/Hexane, 1:9) to give 5.3 g of a white solid. $^1$H NMR CDCl$_3$ δ 2.50 (d, J=3.3 Hz), 5.76 (d, J=3.3 Hz), 7.15–7.47 (m, 7H). MS 286 (M–1). Anal. (C$_{13}$H$_9$Cl$_3$O)C, H, N.

Step B: 1,2-Dichloro-4-[chloro(4-chlorophenyl)methyl]benzene

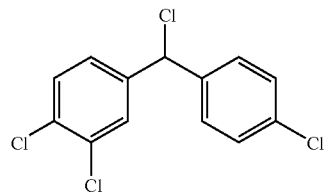

To a solution of (4-chlorophenyl)-(3,4-dichlorophenyl)methanol (5.5 g, 18 mmol) in toluene (40 mL) under nitrogen atmosphere was added thionyl chloride (2.7 mL, 37 mmol). The resulting mixture was stirred 6 hours then concentrated under reduced pressure. The residue was purified by flash chromatography on silica gel (EtOAc/Hexane, 1:20) to give 3.5 g (61%) of a pale yellow oil. $^1$H NMR CDCl$_3$ δ 6.00 (s, 1H), 7.20–7.49 (m, 7H). MS 305 (M–1).

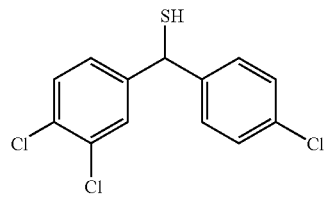

Step C: Chloro-bis(4-trifluoromethyl-phenyl)methanethiol

To a solution of the chloride (3.0 g, 10 mmol) in Ethanol (20 mL) was added Thiourea (0.78 g, 10 mmol). The resulting mixture was warmed to reflux, refluxed 2 hours, cooled lightly, and 50% NaOH (1.0 g, 13 mmol) in H$_2$O (4 mL) added. After refluxing an additional 2 hours, the reaction mixture was acidified with 2N HCl, and extracted with EtOAc. The combined extracts were washed with H$_2$O and brine, then the organic phase was dried over MgSO$_4$ and concentrated under reduced pressure. The residue was purified by flash chromatography on silica gel (EtOAc/Hexane, 1:9) to give 1.43 g (47%) of a pale yellow oil. $^1$H NMR CDCl$_3$ δ 2.27 (d, J=5.4 Hz, 1H), 5.32 (d, J=5.4 Hz, 1H), 7.49–752 (m, 4H), 7.18–7.50 (m, 7H). MS 301 (M–1).

Step D: 3-[(4-Chlorophenyl)-(3,4-dichlorophenyl)methylsulfanyl]-1,1,1-trifluoropropane-2,2-diol To a solution of the thiol (1.4 g, 4.5 mmol) in dry THF (15 mL) under a nitrogen atmosphere and cooled in an ice-bath was added 3-bromo-1,1,1-trifluoroacetone (0.50 mL, 4.8 mmol) followed by triethylamine (0.60 mL, 4.9 mmol) dropwise. The resulting mixture was stirred 1 hour, warmed to room temperature, and stirred 16 hours. The reaction mixture was diluted with dichloromethane (100 mL), then washed with 2N HCl and brine. The organic phase was dried over MgSO$_4$, filtered, and concentrated under reduced pressure. The residue was purified by flash chromatography on silica gel (EtOAc/Hexane, 1:9) to give 1.48 g (79%) of a clear oil. $^1$H NMR δ 2.73 (s, 2H), 3.82 (m, 2H), 5.52 (s, 1H), 7.24–7.49 (m, 7H). MS 423 (M–H$_2$O).

Step E: To a solution of the sulfide (1.5 g, 3.5 mmol) in glacial acetic acid (7.0 mL) was added 30% hydrogen peroxide solution (3 mL) slowly. The resulting mixture was stirred 16 hours, diluted with water (75 mL), and extracted with EtOAc. The combined extracts were washed with water and brine, then the organic phase was dried over MgSO$_4$ and concentrated under reduced pressure. The residue was purified by flash chromatography on silica gel (EtOAc/Hexane, 1:9) to give 0.84 g (54%) of the title product. $^1$H NMR δ 3.25 (m, 1H), 4.18 (q, J=16.1 and 25.7, 1H), 4.69 (m, 1H), 5.02 (s, 1H), 5.80 (d, J=64.7 Hz, 1H), 7.40–7.78 (m, 7H). MS 445 (M−H$_2$O). Anal. (C$_{16}$H$_{12}$Cl$_3$F$_3$O$_4$S)C, H, N.

Example 31

3-[Biphen-4-yl-(4-chlorophenyl)methanesulfonyl]-1,1,1-trifluoropropane-2,2-diol

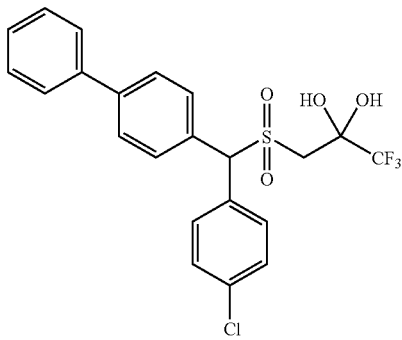

Step A: Biphenyl-4-yl-(4-chlorophenyl)methanol

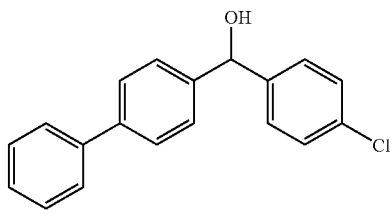

To a solution of 4-biphenylcarboxaldehyde (5.5 g, 30 mmol) in dry Ether (50 mL) under nitrogen atmosphere cooled in an ice-bath was added a 1 M solution of 4-chlorophenylmagnesium bromide in Ether (33 mL, 33 mmol) dropwise. The resulting mixture was stirred 0.5 hours, warmed to room temperature, stirred 2 hours. After cooling to room temperature, the reaction mixture was quenched by the careful addition of 2N HCl, diluted with ether (100 mL) and washed with brine. The organic phase was dried over MgSO$_4$ and concentrated under reduced pressure. The residue was purified by flash chromatography (EtOAc/Hexane, 1:9) to give 7.9 g (90%) of a white solid. $^1$H NMR CDCl$_3$ δ 2.35 (d, J=3.2 Hz), 5.85 (d, J=3.2 Hz), 7.30–7.59 (m, 13H). MS 292 (M−1). Anal. (C$_{19}$H$_{15}$CO)C, H, N.

Step B: 4-[Chloro(4-chlorophenyl)methyl]biphenyl

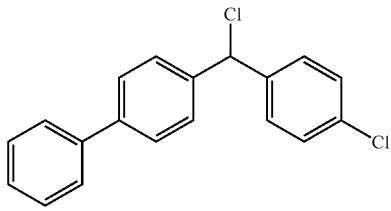

To a solution of biphenyl-4-yl(4-chlorophenyl)methanol (4.0 g, 14 mmol) in toluene (30 mL) under nitrogen atmosphere was added thionyl chloride (1.5 mL, 21 mmol). The resulting mixture was warmed to reflux, refluxed 1 hour, cooled, then concentrated under reduced pressure. The residue was purified by flash chromatography on silica gel (EtOAc/Hexane, 1:20) to give 2.5 g (59%) of a pale white solid. $^1$H NMR CDCl$_3$ δ 6.14 (s, 1H), 7.30–7.587 (m, 13H). MS 311 (M−1).

Step C: Biphen-4-yl(4-chlorophenyl)methanethiol

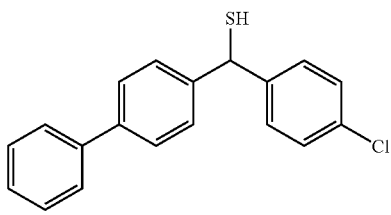

To a solution of the chloride (2.5 g, 8.0 mmol) in Ethanol (20 mL) was added thiourea (0.61 g, 8.0 mmol). The resulting mixture was warmed to reflux, refluxed 2 hours, cooled lightly, and 50% NaOH (1.5 g, 19 mmol) in H$_2$O (4 mL) added. After refluxing an additional 2 hours, the reaction mixture was acidified with 2N HCl and extracted with EtOAc. The combined extracts were washed with H$_2$O and brine, then the organic phase was dried over MgSO$_4$, and concentrated under reduced pressure. The residue was purified by flash chromatography on silica gel (EtOAc/Hexane, 1:9) to give 2.08 g (47%) of a white solid. $^1$H NMR CDCl$_3$ δ 2.74 (m, 1H), 5.29 (s, 1H), 7.31–7.58 (m, 13H). MS 308 (M−1).

Step D: 3-[Biphen-4-ly-(4-chlorophenyl)methylsulfanyl]-1,1,1-trifluoropropane-2,2-diol To a solution of the thiol (1.5 g, 4.8 mmol) in dichloromethane (20 mL) under a nitrogen atmosphere and cooled in an ice-bath was added 3-bromo-1,1,1-trifluoroacetone (0.60 mL, 5.8 mmol) followed by triethylamine (0.80 mL, 5.7 mmol) dropwise. The resulting mixture was stirred 1 hour, warmed to room temperature, and stirred 16 hours. The reaction mixture was diluted with dichloromethane (100 mL), then washed with 2N HCl and brine. The organic phase was dried over MgSO$_4$, filtered, and concentrated under reduced pressure. The residue was purified by flash chromatography on silica gel (EtOAc/Hexane, 1:9) to give 1.11 g (53%) of a clear oil. $^1$H NMR δ 2.77 (d, J=1.1 Hz, 2H), 3.78 (d, J=1.1 HZ, 1H), 3.91 (s, 1H), 5.30 (s, 1H), 7.33–7.58 (m, 13H). MS 419 (M−H$_2$O).

Step E: To a solution of the sulfide (1.0 g, 3.5 mmol) in glacial acetic acid (7.0 mL) was added 30% hydrogen peroxide solution (3 mL) slowly. The resulting mixture was stirred 16 hours, diluted with water (75 mL), and extracted with EtOAc. The combined extracts were washed with water and brine, then the organic phase was dried over MgSO$_4$ and concentrated under reduced pressure. The residue was purified by flash chromatography on silica gel (EtOAc/Hexane, 1:9) to give 0.86 g (80%) of the title product. $^1$H NMR δ 3.30 (q, J=15.1 and 30.5, 2H), 5.07 (s, 1H), 5.16 (s, 1H), 5.98 (s, 1H), 7.36–7.71 (m, 13H). MS 451 (M–H$_2$O). Anal. (C$_{22}$H$_{18}$ClF$_3$O$_4$S) C, H, N.

Example 32

3-[(4-Chlorophenyl)-(4-isobutylphenyl)methanesulfonyl]-1,1,1-trifluoropropane-2,2-diol and 3 [(4-Chlorophenyl)-(4-isobutylphenyl)methanesulfonyl]-1,1,1-trifluoropropan-2-one

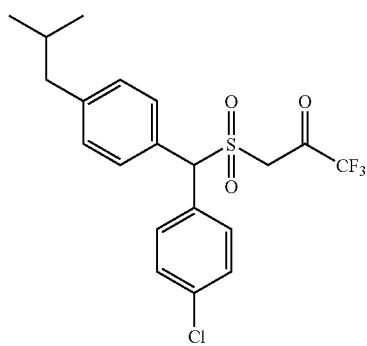

Step A: (4-Chlorophenyl)-(4-isobutylphenyl)methanol

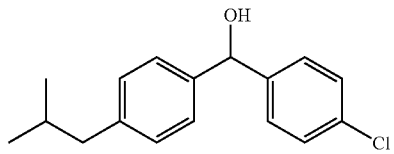

To a solution of 4-isobutylbenzaldehyde (3.25 g, 30 mmol) in dry Ether (30 mL) under nitrogen atmosphere cooled in an ice-bath was added a 1 M solution of 4-chlorophenylmagnesium bromide in Ether (23 mL, 23 mmol) dropwise. The resulting mixture was stirred 0.5 hours, warmed to room temperature, stirred 2 hours. After cooling to room temperature, the reaction mixture was quenched by the careful addition of 2N HCl, diluted with ether (100 mL) and washed with brine. The organic phase was dried over MgSO$_4$, and concentrated under reduced pressure. The residue was purified by flash chromatography (EtOAc/Hexane, 1:9) to give 3.79 (69%) of a white solid. $^1$H NMR CDCl$_3$ δ 0.80 (d, J=6.7 Hz, 6H), 1.79–1.87 (m, 1H), 2.44 (d, J=7.1 Hz, 2H), 5.79 (J=2.7, 1H) 7.09–7.34 (m, 8H). MS 273 (M–1). Anal. (C$_{17}$H$_{15}$ClO) C, H, N.

Step B: 4-[chloro(4-Chlorophenyl)methyl]isobutylphenyl

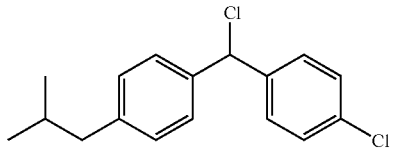

To a solution of (4-chlorophenyl)-(4-isobutylphenyl) methanol (3.5 g, 13 mmol) in toluene (20 mL) under nitrogen atmosphere was added thionyl chloride (1.9 mL, 29 mmol). The resulting mixture was warmed to reflux, refluxed 1 hour, cooled, then concentrated under reduced pressure. The residue was purified by flash chromatography on silica gel (EtOAc/Hexane, 1:9) to give 3.6 g (97%) of a pale yellow oil. $^1$H NMR CDCl$_3$ δ 0.89 (d, J=6.6 Hz, 6H), 1.79–1.87 (m, 1H), 2.43 (d, J=7.1, 2H), 6.07 (s, 1H), 7.10–7.36 (m, 8H). MS 292 (M–1).

Step C: (4-Chlorophenyl)-(4-isobutylphenyl)methanethiol

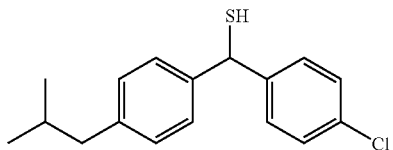

To a solution of the chloride (3.4 g, 11.6 mmol) in Ethanol (10 mL) was added thiourea (0.61 g, 8.0 mmol). The resulting mixture was warmed to reflux, refluxed 2 hours, cooled lightly, and 50% NaOH (1.5 g, 19 mmol) in H$_2$O (4 mL) added. After refluxing an additional 2 hours, the reaction mixture was acidified with 2N HCl and extracted with EtOAc. The combined extracts were washed with H$_2$O and brine, then the organic phase was dried over MgSO$_4$ and concentrated under reduced pressure. The residue was purified by flash chromatography on silica gel (EtOAc/Hexane, 1:9) to give 2.16 g (64%) of a clear oil. $^1$H NMR CDCl$_3$ δ 0.88 (d, J=6.5, 6H), 1.75–1.85 (m, 1H), 2.25 (d, J=4.9, 1H), 2.35 (d, J=7.1), 5.38 (d, J=4.0, 1H), 7.07–7.36 (m, 8H). MS 289 (M–1).

Step D: To a solution of the thiol (2.0 g, 6.9 mmol) in dichloromethane (20 mL) under a nitrogen atmosphere and cooled in an ice-bath was added 3-bromo-1,1,1-trifluoroacetone (0.75 mL, 7.2 mmol) followed by triethylamine (1.0 mL, 7.2 mmol) dropwise. The resulting mixture was stirred 1 hour, warmed to room temperature, and stirred 16 hours. The reaction mixture was diluted with dichloromethane (100 mL), then washed with 2N HCl and brine. The organic phase was dried over MgSO$_4$, filtered, and concentrated under reduced pressure. The residue was purified by flash chromatography on silica gel (EtOAc/Hexane, 1:9) to give 1.9 g (66%) of a clear oil. Used without further purification.

Step E: To a solution of the sulfide (1.9 g, 4.5 mmol) in glacial acetic acid (7.0 mL) was added 30% hydrogen peroxide solution (3 mL) slowly. The resulting mixture was stirred 16 hours, diluted with water (75 mL), and extracted with EtOAc. The combined extracts were washed with water and brine, then the organic phase was dried over MgSO$_4$ and concentrated under reduced pressure. The residue was purified by flash chromatography on silica gel (EtOAc/Hexane, 1:9) to give 1.21 g (60%) of a 2:1 mixture of the diol and ketone. Anal Calc for (C$_{20}$H$_{22}$ClF$_3$O$_4$S).0.33 (C$_{20}$H$_{20}$ClF$_3$O$_3$S): C, 53.81; H, 4.86; N, 0.00; F, 12.77; Cl, 7.94. Found: C, 54.04; H, 4.81; N, <0.05; F, 12.80; Cl, 8.34. mp 45–50° C.

Example 33

1-[Bis-(4-chloro-phenyl)-methanesulfonyl]-3-(4-fluoro-phenyl)-propan-2-one

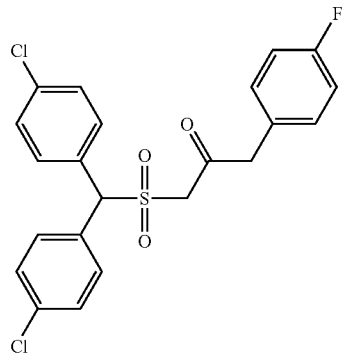

Step A: 1-[Bis-(4-chloro-phenyl)-methylsulfanyl]-3-(–4-fluoro-phenyl)-propan-2-one

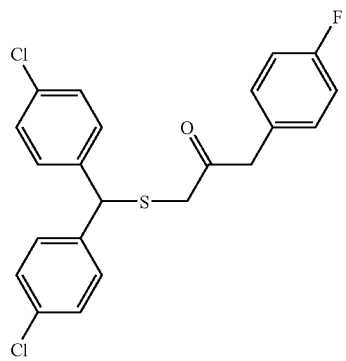

To a solution of 2-[bis-(4-chloro-phenyl)-methysulfanyl]-N-methoxy-N-methyl-acetamide (Example 1, Step A, 2.1 g, 6.14 mmol) in THF chilled to –78° C. was dripped in 100 mL of 0.25 M 4-fluorobenzylmagnesium chloride in THF over 30 minutes. The reaction mixture was allowed to warm to room temperature and stirred for 1 hour. The reaction mixture was then chilled to –78° C. and 100 mL of concentrated aqueous solution of ammonium chloride was dripped into the reaction mixture. The reaction was warmed to room temperature and the organics were extracted with ethyl acetate. The organic layer was separated, washed with brine, dried (sodium sulfate), filtered and then concentrated in vacuo. The residue was purified by flash chromatography (silica gel, eluting with 5% ethyl acetate in hexane) to provide 1.16 g (45%) of product as a yellow oil; MS (APCI-); $^1$H NMR is consistent with the desired product structure.

Step B: 3-Chloroperbenzoic acid (0.82 g, 4.8 mmol) was added to a solution of 1-[bis-(4-chloro-phenyl)-methylsulfanyl]-3-(–4-fluoro-phenyl)-propan-2-one (0.5 g, 1.2 mmol) in 50 mL of dichloromethane. The resulting reaction mixture was stirred for 12 hours at ambient temperature. The reaction was quenched with addition of concentrated aqueous solution of sodium bicarbonate. The organic layer was separated, washed with brine, dried (sodium sulfate), filtered and then concentrated in vacuo. After removing residual solvent via high vacuum, a few drops of ether were added to the residue, the desired product crystallized within 5 minutes. Trituration of this resulting solid with ether gave 0.045 g of white solid (8%): mp 106–107° C.; MS (APCI-); Anal. Calcd for $C_{22}H_{17}Cl_2F_1O_3S_1$: C, 58.55; H, 3.80. Found: C, 58.46; H, 3.58. $^1$H NMR is consistent with the desired product structure.

Example 34

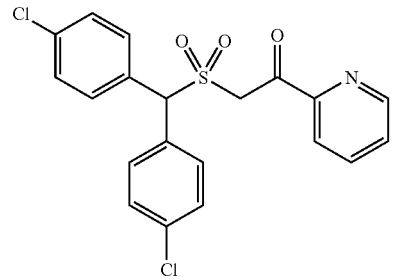

Step A: 2-[Bis-(4-chloro-phenyl)-methylsulfanyl]-1-pyridin-2-yl-ethanone

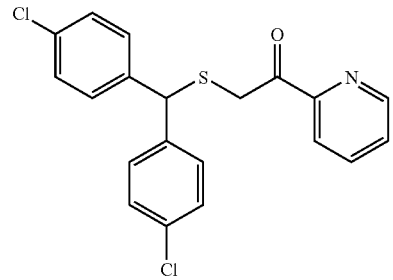

Prepared as an oil in 75% yield from bis-(4-chlorophenyl)-methanethiol and 2-bromo-1-pyridin-2-yl-ethanone hydrobromide by the procedure described in Example 17. The crude product was purified by chromatography (eluting with 2:8 ethyl acetate/hexane); MS (APCI-), m/z 388; $^1$H NMR consistent with desired product structure.

Step B: 2-[Bis-(4-chloro-phenyl)-methanesulfonyl]-1-pyridin-2-yl-ethanone

Prepared in 56% yield from 2-[bis-(4-chloro-phenyl)-methylsulfanyl]-1-pyridin-2-yl-ethanone and 3-chloroperoxybenzoic acid by the procedure described in Step B of Example 20. The crude product was purified by chromatography (eluting with 1:99 methanol/dichloromethane). A sample recrystallized from ethyl acetate/hexane had mp 120–121° C.; MS (APCI-), m/z 420; $^1$H NMR consistent with desired product structure.

Example 35

1-[Bis-(4-chloro-phenyl)-methanesulfonyl]-1-fluoro-propan-2-one

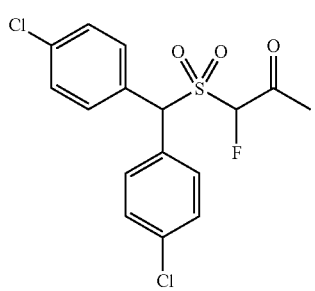

To a stirring solution of the methyl ketone (Example 1, 0.6 g, 1.7 mmol) in dry THF (11 mL) at 0° C., under dry nitrogen was added LiHMDS (1.0 M/THF, 2.2 mL, 1.2 mmol) and the mixture stirred for 30 minutes without warming. After this time, the resulting enolate was lowered to −78° C., whereupon a solution of N-fluorobenzenesulfonamide (0.85 g, 2.7 mmol) in dry THF (5.0 mL) was added via canula. The reaction was then stirred for 30 minutes and then at room temperature for 1 hour, and was then diluted with water and extracted with ethyl acetate. The organic layers were combined, dried on $Na_2SO_4$, and filtered to give a mixture that was purified on $SiO_2$ with 15%–20% EtOAcHexane to give (0.075 g, the fluorinated species as a colorless oil. Anal. Calcd for $C_{16}H_{13}Cl_2F_1O_3S_1$: 0.15$H_2O$: Calcd C, 50.85; H, 3.55; Cl, 18.76; F, 5.03; O, 13.33; S, 8.48. Found: C, 50.45; H, 3.51; S, 8.15. $^1$H NMR ($CDCl_3$, 400 MHz): δ 2.1 (s, 3H), 5.2 (d, 1H, J=49.0 Hz), 5.65 (s, 1H), 7.28–7.5 (m, 4H), 7.5–7.7 (m, 4H).

Biological Example 1

Compounds of were evaluated for their effect on calcium flux using methodology known in the art, e.g., Neote et al., Cell 1993, 72:415–425. Briefly, THP-1 cells were incubated with the fluorescence dye FLUO-4 for 1 hour, the cells were washed after this loading period, resuspended in HANKs buffer, and loaded into a 384-well plate. The cells were then incubated in the presence of a compound of Example 1–12, 14, 18, 22–23, 27–28, 30, or [bis-(4-chloro-phenyl)-methanesulfonyl]-acetic acid methyl ester. After a 30-minute incubation period, the cells were stimulated with 33 nM human MCP-1 and the calcium flux response recorded and quantified with a FLIPR$^{384}$® (384-well Fluorometric Imaging Plate Reader) (Molecular Dynamics, Sunnyvale, Calif.). The $IC_{50}$'s (µM) of the inhibition of the maximal MCP-1 response are set out in Table 1.

TABLE 1

| Example | Calcium Flux $IC_{50}$, µM |
|---|---|
| 1 | 2.2 |
| 2 | 7.65 |
| 3 | 1.125 |
| 4 | 0.495 |
| 5 | 7.25 |
| 6 | 1.343 |
| 7 | 0.423 |
| 8 | 0.108 |
| 9 | 2.9 |
| 10 | 0.984 |
| 11 | 4.750 |
| 12 | 8.150 |
| 14 | 3.9 |
| 18 | 5.2 |
| 22 | 2.467 |
| 23 | 1.52 |
| 27 | 6.525 |
| 28 | 0.417 |
| 30 | 0.393 |
| [Bis-(4-chloro-phenyl)-methanesulfonyl]-acetic acid methyl ester | 0.150 |

Biological Example 2

Compounds were also assayed for their ability to inhibit the binding of radiolabeled MCP-1 to cell membranes. The materials and methods are set out below.

Membrane Preparation. 300-19 cells were harvested by centrifugation and washed with PBS (Dulbecco's phosphate-buffered saline w/o Ca and Mg). Cells were frozen at −80° C. overnight then resuspensed in ice cold lysis buffer (5 mM HEPES, 2 mM EDTA, 10 µg/mL of leupeptin, aprotinin, and chymostatin, and 200 µg/mL PMSF). The cell suspension was centrifuged at 1,000 rpm for 10 minutes and the supernatant was transferred and centrifuged at 14,000 rpm for 45 minutes at 4° C. then discarded. The resulting pellet was resuspended in stock buffer (10 mM HEPES, 300 mM sucrose, 20 µg/mL of leupeptin, aprotinin, and chymostatin, and 200 µg/mL PMSF), aliquoted, and frozen at −80° C. until use. Typical binding assays used 1.0 µg/well protein.

Prepared membranes were resuspended in binding buffer (50 mM Tris, 10 mM $MgCl_2$, 1 mM EDTA pH 7.4) at 10 µg/mL protein. Membranes (1.0 µg/well) were incubated with $^{125}$I-MCP-1 (0.15 nM) in the absence or presence of unlabeled chemokine (465 nM) or a compound of Examples 1–11, 14, 16, 19, 22, 27–30, 33–34, or [bis-(4-chloro-phenyl)-methanesulfonyl]-acetic acid methyl ester (0.001 µM–40 µM) for 3 hours at room temperature in a 96-well plate (total volume 250 µL). The reaction was terminated by filtration using a 96-well plate harvester (Packard Filtermate 196 Harvester). Filters (Packard GF/C) were prewet with 0.3% PEI containing 0.5% BSA and washed 5 times with wash buffer (DPBS, 0.3 $MnCl_2$, and 0.25% BSA) prior to reaction termination. After terminating the reaction, filters were washed 6 times with wash buffer, and allowed to dry overnight. Scintillation fluid (Packard's Micro Scint 20) was added to each well and radioactivity bound was determined by liquid scintillation spectrometry. Nonspecific binding was determined in the presence of 465 nM unlabeled MCP-1. The $IC_{50}$'s (µM) of the inhibition of the binding of the iodinated MCP-1 are set out in Table 2.

TABLE 2

| Example | $IC_{50}$, µM |
|---|---|
| 1 | 1.150 |
| 2 | 7.367 |
| 3 | 0.165 |
| 4 | 0.175 |
| 5 | 2.550 |
| 7 | 0.101 |
| 8 | 0.088 |
| 9 | 6.3 |
| 10 | 3.450 |
| 11 | 3.40 |
| 14 | 1.350 |
| 16 | 12.667 |
| 19 | 6.150 |
| 22 | 1.275 |
| 27 | 2.7 |
| 28 | 0.210 |
| 29 | 3.000 |
| 30 | 0.077 |
| 33 | 14.5 |
| 34 | 4.250 |
| [Bis-(4-chloro-phenyl)-methanesulfonyl]-acetic acid methyl ester | 7.320 |

Biological Example 3

The compound of Example 4, 3-[Bis-(4-chloro-phenyl)-methanesulfonyl]-1,1,1-trifluoro-propan-2-one, was administered to rats via a 5-minute intravenous infusion at 0.175 mg/mL (solution in 5% DMA/95% Tris base (50 mM in water)) and oral gavage at 0.35 mg/mL (suspension in 5% (w/v) PEG 200/95% (w/v) methylcellulose (0.5%)). Following intravenous administration of a 0.5 mg/kg dose to rats, the systemic clearance was about 0.06 mL/min/kg and the volume of distribution was about 0.2 L/kg. The apparent terminal elimination half-life was about 47 hours. Following a 1 mg/kg oral dose, the compound of Example 4 was absorbed in rats with mean peak plasma levels of 6 µg/mL occurring approximately 2.5 hours after dosing. Based on the ratio of the dose-normalized area under the plasma concentration-time curve from 0 to 96 hour after oral and intravenous doses, the absolute oral bioavailability averaged about 100%.

Biological Example 4

The compound of Example 8, 3-[bis-(4-chloro-phenyl)-methanesulfonyl]-1,1-difluoro-propan-2-one, was administered to rats via a 5 minute intravenous infusion (solution in 5% DMA/95% Tris base (50 mM in water)) and oral gavage (suspension in 5% (w/v) PEG 200/95% (w/v) methylcellulose (0.5%)) to assess its pharmacokinetic properties. Following intravenous administration of 1 mg/kg to rats, the systemic clearance was 0.75 mL/min/kg and the volume of distribution was 0.28 L/kg. The apparent terminal elimination half-life was 7 hours. Following a 5 mg/kg oral dose, 3-[bis-(4-chloro-phenyl)-methanesulfonyl]-1,1-difluoro-propan-2-one was absorbed in rats with mean peak plasma levels of about 7 µg/mL occurring approximately 0.5–1 hours after dosing. Based on the ratio of the dose-normalized area under the plasma concentration-time curve from 0 to infinity after oral and intravenous doses, the absolute oral bioavailability averaged about 43%.

Biological Example 5

3-[Bis-(4-chloro-phenyl)-methanesulfonyl]-1-fluoro-propan-2-one

The compound of Example 7, 3-[bis-(4-chloro-phenyl)-methanesulfonyl]-1-fluoro-propan-2-one, was administered to rats via a 5-minute intravenous infusion (solution in 5% DMA/95% Tris base (50 mM in water)) and oral gavage (suspension in 5% (w/v) PEG 200/95% (w/v) methylcellulose (0.5%)) to assess its pharmacokinetic properties. After administration of 1 mg/kg of the compound of Example 7 as an intravenous infusion, there was a >100-fold decrease in concentrations within 2 hours after dosing. Following oral administration of 5 mg/kg to rats, plasma concentrations of 3-[bis-(4-chloro-phenyl)-methanesulfonyl]-1-fluoro-propan-2-one were measurable for 4 hours after dosing. Mean peak plasma levels of 359 ng/mL occurred at 15 minutes after dosing, and the oral bioavailability relative to the intravenous dose was less than 10%. The apparent terminal elimination half-life was 1.5 hours.

Biological Example 6

(Di-p-tolyl-methanesulfonyl)-acetic acid methyl ester was administered to rats via a 5-minute intravenous infusion (dose 1 mg/kg as a solution in 10% DMA, 10% ethanol, 40% 1,2-propanediol, 40% D5W) and oral gavage (dose 5 mg/kg as a suspension in 5% PEG 200, 95% methylcellulose (0.5%)). After intravenous or oral administration, plasma concentrations of (Di-p-tolyl-methanesulfonyl)-acetic acid methyl ester were below the lower limit of quantitation using LC/MS.

Biological Example 7

Plasma stability studies were conducted on (Di-p-tolyl-methanesulfonyl)-acetic acid methyl ester and [bis-(4-chloro-phenyl)-methanesulfonyl]-acetic acid methyl ester. Briefly, these compounds (at a final concentration of 1 µg/mL) were separately inclubated in rat plasma and acidified rat plasma for 1 hour at room temperature or 37° C. After the incubation period, these compounds were below the lower limit of quantitation using LC/MS.

Formulation Example 1

| Tablet Formulation | |
|---|---|
| Ingredient | Amount |
| Compound of Example 4 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compounds of the present invention (e.g., the compound of Example 4) can be mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for treatment of inflammation.

Formulation Example 2

Parenteral Solution

In a solution of 700 mL of propylene glycol and 200 mL of water for injection is added 20.0 g of a compound of the present invention. The mixture is stirred, and the pH is adjusted to 5.5 with hydrochloric acid. The volume is adjusted to 1000 mL with water for injection. The solution is sterilized, filled into 5.0 mL ampoules, each containing 2.0 mL (40 mg of invention compound), and sealed under nitrogen. The solution is administered by injection to a patient suffering from a chemokine associated disorder (e.g., rheumatoid arthritis, atherosclerosis, etc.) and in need of treatment.

Formulation Example 3

Patch Formulation

Ten milligrams of a compound of the present invention is mixed with 1 mL of propylene glycol and 2 mg of acrylic-based polymer adhesive containing a resinous cross-linking agent. The mixture is applied to an impermeable backing (30 cm$^2$) and applied to the upper back of a patient for sustained release treatment of a chemokine associated disorder (e.g., rheumatoid arthritis, atherosclerosis, etc.).

It is understood that the examples and embodiments described here in are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of Formula I or II:

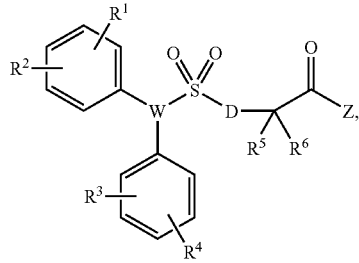

I

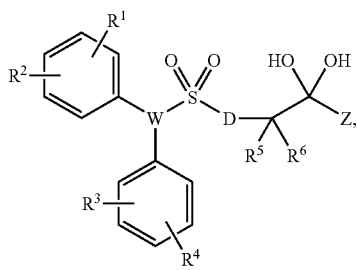

II or a pharmaceutically acceptable salt of a compound of Formula I or II;

wherein:

D is $(CH_2)_n$, where n is 0 or 1;

$R^1$, $R^2$, $R^3$, and $R^4$ are each independently selected from the group consisting of: H, $C_1$–$C_6$alkyl, $C_3$–$C_6$cycloalkyl, $C_3$–$C_6$heterocycloalkyl, phenyl, halogen, and $CF_3$;

W is N, CH, or CF;

$R^5$ and $R^6$ are each independently H or F;

Z is selected from the group consisting of:

$C_1$–$C_6$ alkyl, $CH_2Br$, $CH_2Cl$, $CF_3$, $CH_2F$, $CHF_2$, $CH_2R^7$, $CFR^7R^8$, $CF_2R^7$, $CH_2OR^7$, $CHFOR^7$, $CF_2OR^7$, $C(O)NR^7R^8$, $CO_2R^7$,

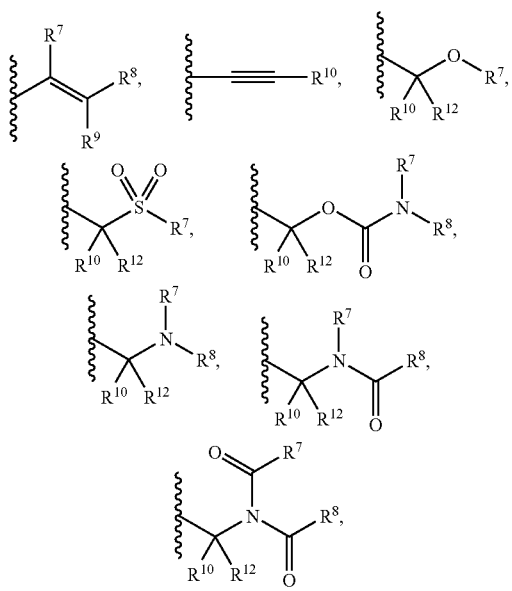

phenyl, $C_6$–$C_{12}$aryl, and $C_5$–$C_{12}$heteroaryl;

$R^7$, $R^8$, and $R^9$, are independently selected from the group consisting of H, $C_1$–$C_6$alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_1$–$C_6$alkyl-;

$R^{10}$ and $R^{12}$ are independently selected from the group consisting of F, H, $C_1$–$C_6$alkyl, $CF_3$, $CCl_3$, $C_6$–$C_{12}$aryl, $C_6$–$C_{12}$aryl-$C_1$–$C_6$alkyl-, $C_5$–$C_{12}$heteroaryl, and $C_5$–$C_{12}$heteroaryl-$C_1$–$C_6$alkyl-; and wherein 2-(diphenyl-methanesulfonyl)-1-pyridin-2-yl-ethanone is not included.

2. The compound according to claim 1,
wherein D is 0;
wherein W is CH;
wherein $R^1$, $R^2$, $R^3$, and $R^4$ are each independently selected from the group consisting of: H, $C_1$–$C_6$ alkyl, and halogen.

3. The compound according to claim 2, wherein Z is selected from the group consisting of:
$CF_3$, $CH_2Cl$, $CH_2F$, $CHF_2$, $CH_2R^7$, $CFR^7R^8$, $CF_2R^7$, $CH_2OR^7$, $CHFOR^7$, and $CF_2OR^7$.

4. The compound according to claim 2,
wherein $R^{10}$ and $R^{12}$ are H or F; and
wherein Z is selected from the group consisting of:

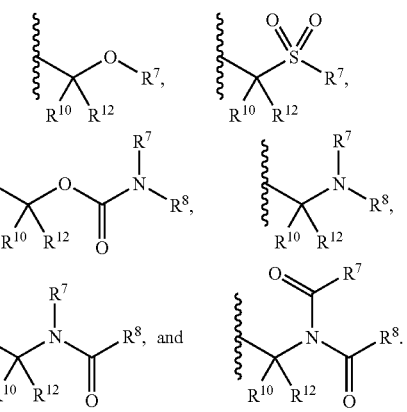

5. The compound according to claim 4,
wherein $R^{10}$ and $R^{12}$ are H.

6. The compound according to claim 5,
wherein $R^7$ and $R^8$ are independently selected from the group consisting of H, $C_1$–$C_6$ alkyl, and $CF_3$.

7. The compound according to claim 1, wherein the compound is selected from the group consisting of:

1-[Bis-(4-chloro-phenyl)-methanesulfonyl]-propan-2-one;

1-[Bis-(4-chloro-phenyl)-methanesulfonyl]-butan-2-one;

1-[Bis-(4-chloro-phenyl)-methanesulfonyl]-3-bromo-propan-2-one;

3-[Bis-(4-chloro-phenyl)-methanesulfonyl]-1,1,1-trifluoro-propan-2-one;

2-[Bis-(4-chloro-phenyl)-methanesulfonyl]-1-furan-2-yl-ethanone;

1-[Bis-(4-chloro-phenyl)-methanesulfonyl]-pent-3-yn-2-one;

3-[Bis-(4-chloro-phenyl)-methanesulfonyl]-1-fluoro-propan-2-one;

3-[Bis-(4-chloro-phenyl)-methanesulfonyl]-1,1-difluoro-propan-2-one;

1-[Bis-(4-chloro-phenyl)-methanesulfonyl]-3-phenyl-propan-2-one;

1-[Bis-(4-chloro-phenyl)-methanesulfonyl]-3-phenoxy-propan-2-one;

1-[Bis-(4-chloro-phenyl)-methanesulfonyl]-3-(4-methoxy-phenoxy)-propan-2-one;
1-[Bis-(4-chloro-phenyl)-methanesulfonyl]-3-(4-chlorophenoxy)-propan-2-one;
1-[Bis-(4-chloro-phenyl)-methanesulfonyl]-3-(2,4-difluoro-phenoxy)-propan-2-one;
1-[Bis-(4-chloro-phenyl)-methanesulfonyl]-3-methoxy-propan-2-one;
1-[Bis-(4-chloro-phenyl)-methanesulfonyl]-pent-3-ene-2-one;
2-[Bis-(4-chloro-phenyl)-methanesulfonyl]-1-(1-methyl-1H-imidazol-2-yl)-ethanone;
5-(2-[Bis-(4-chloro-phenyl)-methanesulfonyl]-acetyl)-thiophene-2-carboxylic acid dimethylamide;
2-[Bis-(4-chloro-phenyl)-methanesulfonyl]-1-thiophen-2-yl-ethanone;
1-[Bis-(4-chloro-phenyl)-methanesulfonyl]-3,3-dimethyl-butan-2-one;
1-[Bis-(4-chloro-phenyl)-methanesulfonyl]-4-phenyl-butan-2-one;
4-[Bis-(4-chloro-phenyl)-methanesulfonyl]-3-oxo-butyric acid methyl ester;
4-[Bis-(4-chloro-phenyl)-methanesulfonyl]-N-(2-chloro-phenyl)-3-oxo-butyramide;
4-[Bis-(4-chloro-phenyl)-methanesulfonyl]-butan-2-one;
Acetic acid 3-[bis-(4-chloro-phenyl)-methanesulfonyl]-2-oxo-propyl ester;
1-[Bis-(4-chloro-phenyl)-methanesulfonyl]-4,4,4-trifluoro-butan-2-one;
1-[Bis-(4-chloro-phenyl)-methanesulfonyl]-3-phenyl-methanesulfonyl-propan-2-one;
3-[Bis(4-fluorophenyl)methanesulfonyl]-1,1,1-trifluoropropane-2,2-diol;
3-[Bis(4-trifluoromethyl-phenyl)methanesulfonyl]-1,1,1-trifluoropropane-2,2-diol;
3-[(4-Chlorophenyl)-(3,4-dichlorophenyl)methanesulfonyl]-1,1,1-trifluoropropane-2,2-diol;
3-[Biphen-4-yl-(4-chlorophenyl)methanesulfonyl]-1,1,1-trifluoropropane-2,2-diol;
3-[(Chlorophenyl)-(4-isobutylphenyl)methanesulfonyl]-1,1,1-trifluoropropane-2,2-diol;
3[(4-Chlorophenyl)-(4-isobutylphenyl)methanesulfonyl]-1,1,1-trifluoropropan-2-one;
1-[Bis-(4-chloro-phenyl)-methanesulfonyl]-3-(4-fluoro-phenyl)-propan-2-one;
2-[Bis-(4-chloro-phenyl)-methylsulfonyl]-1-pyridin-2-yl-ethanone;
1-[Bis-(4-chloro-phenyl)-methanesulfonyl]-1-fluoro-propan-2-one;
3-[Bis-(4-chloro-phenyl)-methanesulfonyl]-3,3-difluoro-butan-2-one;
1-[Bis-(4-chloro-phenyl)-methanesulfonyl]-3-fluoro-butan-2-one;
(R)-1-[Bis-(4-chloro-phenyl)-methanesulfonyl]-3,3-difluoro-4-phenyl-pentan-2-one;
(S)-1-[Bis-(4-chloro-phenyl)-methanesulfonyl]-3,3-difluoro-4-phenyl-pentan-2-one;
1-[Bis-(4-chloro-phenyl)-methanesulfonyl]-4-(3,4-dimethoxy-phenyl)-3,3-difluoro-butan-2-one;
3-[Bis-(4-chloro-phenyl)-methanesulfonyl]-N,N-dimethyl-2-oxo-propionamide;
1-[Bis-(4-chloro-phenyl)-methanesulfonyl]-3-hydroxy-propan-2-one;
1-[Bis-(4-chloro-phenyl)-methanesulfonyl]-3-methoxy-propan-2-one;
3-[Bis-(4-chloro-phenyl)-methanesulfonyl]-1,1-difluoro-1-methoxy-propan-2-one;
1-[Bis-(4-chloro-phenyl)-methanesulfonyl]-3,3-difluoro-butan-2-one;
1-[Bis-(4-chloro-phenyl)-methanesulfonyl]-4,4,4-trichloro-3,3-difluoro-butan-2-one;
1-[Bis-(4-chloro-phenyl)-methanesulfonyl]-3,3-difluoro-butan-2-one;
1-[Bis-(4-chloro-phenyl)-methanesulfonyl]-3,3-difluoro-4-methyl-pentan-2-one;
6-[Bis-(4-chloro-phenyl)-methanesulfonyl]-4,4-difluoro-5-oxo-hexanoic acid methyl ester;
3-[1-(4-Chloro-phenyl)-1-(3,4-dichloro-phenyl)-methanesulfonyl]-1,1,1-trifluoro-propan-2-one;
3-[Bis-(3,4-dichloro-phenyl)-methanesulfonyl]-1,1,1-trifluoro-propan-2-one;
1-Benzyloxy-3-[bis-(4-chloro-phenyl)-methanesulfonyl]-propan-2-one;
1-[1-(4-Chloro-phenyl)-1-(3,4-dichloro-phenyl)-methanesulfonyl]-4-(3,4-dimethoxy-phenyl)-3,3-difluoro-butan-2-one;
1-[Bis-(3,4-dichloro-phenyl)-methanesulfonyl]-4-(3,4-dimethoxy-phenyl)-3,3-difluoro-butan-2-one;
3,3,3-Trifluoro-2-oxo-propane-1-sulfonic acid bis-(4-chloro-phenyl)-amide;
4-(3,4-Dimethoxy-phenyl)-3,3-difluoro-2-oxo-butane-1-sulfonic acid bis-(4-chloro-phenyl)-amide;
4-(3,4-Dimethoxy-phenyl)-3,3-difluoro-2-oxo-butane-1-sulfonic acid (4-chloro-phenyl)-(3,4-dichloro-phenyl)-amide;
2-[Bis-(4-chloro-phenyl)-methanesulfonyl]-1-(5-methyl-furan-2-yl)-ethanone;
2-[Bis-(4-chloro-phenyl)-methanesulfonyl]-1-(5-nitro-furan-2-yl)-ethanone;
2-[Bis-(4-chloro-phenyl)-methanesulfonyl]-1-[5-(2,4-difluoro-phenyl)-furan-2-yl]-ethanone;
2-[Bis-(4-chloro-phenyl)-methanesulfonyl]-1-oxazol-2-yl-ethanone;
2-[Bis-(4-chloro-phenyl)-methanesulfonyl]-1-(5-phenyl-isoxazol-3-yl)-ethanone;
2-[Bis-(4-chloro-phenyl)-methanesulfonyl]-1-[5-(3,4-dichloro-phenyl)-isoxazol-3-yl]-ethanone;
2-[Bis-(4-chloro-phenyl)-methanesulfonyl]-1-[5-(2,4-dichloro-phenyl)-isoxazol-3-yl]-ethanone;
2-[Bis-(4-chloro-phenyl)-methanesulfonyl]-1-[3-(4-chloro-phenyl)-isoxazol-5-yl]-ethanone;
2-[Bis-(4-chloro-phenyl)-methanesulfonyl]-1-[3-(3-trifluoromethyl-phenyl)-isoxazol-5-yl]-ethanone;
2-[Bis-(4-chloro-phenyl)-methanesulfonyl]-1-[3-(2,4-dichloro-phenyl)-isoxazol-5-yl]-ethanone;
2-[Bis-(4-chloro-phenyl)-methanesulfonyl]-1-[3-(3-chloro-5-trifluoromethyl-pyridin-2-yl)-isoxazol-5-yl]-ethanone;
2-[Bis-(4-chloro-phenyl)-methanesulfonyl]-1-(5-nitro-thiophen-2-yl)-ethanone;
5-{2-[Bis-(4-chloro-phenyl)-methanesulfonyl]-ethanoyl}-thiophene-2-carboxylic acid dimethylamide;
5-{2-[Bis-(4-chloro-phenyl)-methanesulfonyl]-ethanoyl}-thiophene-2-carbonitrile;
2-[Bis-(4-chloro-phenyl)-methanesulfonyl]-1-thiazol-2-yl-ethanone;
2-[Bis-(4-chloro-phenyl)-methanesulfonyl]-1-(4,5-dihydro-thiazol-2-yl)-ethanone;
2-[Bis-(4-chloro-phenyl)-methanesulfonyl]-1-(1-oxo-4,5-dihydro-1H-1l4-thiazol-2-yl-ethanone;
2-[Bis-(4-chloro-phenyl)-methanesulfonyl]-1-(dioxo-4,5-dihydro-1H-1l6-thiazol-2-yl-ethanone;
2-[Bis-(4-chloro-phenyl)-methanesulfonyl]-1-(2-phenyl-thiazol-4-yl]-ethanone;

2-[Bis-(4-chloro-phenyl)-methanesulfonyl]-1-[2-(4-trifluoromethyl-phenyl)-thiazol-4-yl]-ethanone;
2-[Bis-(4-chloro-phenyl)-methanesulfonyl]-1-pyridin-2-yl-ethanone;
2-[Bis-(4-chloro-phenyl)-methanesulfonyl]-1-pyridin-4-yl-ethanone;
2-[Bis-(4-chloro-phenyl)-methanesulfonyl]-1-pyrimidin-2-yl-ethanone;
1-Benzofuran-2-yl-2-[bis-(4-chloro-phenyl)-methanesulfonyl]-ethanone;
2-[Bis-(4-chloro-phenyl)-methanesulfonyl]-1-[5-nitro-benzofuran-2-yl]-ethanone;
2-[Bis-(4-chloro-phenyl)-methanesulfonyl]-1-(7-hydroxy-benzofuran-2-yl)-ethanone.
1-[Bis-(4-chloro-phenyl)-methanesulfonyl]-3-(4-trifluoromethyl-phenoxy)-propan-2-one;
1-[Bis-(4-chloro-phenyl)-methanesulfonyl]-3-(4-methanesulfonyl-phenoxy)-propan-2-one;
Ethyl-carbamic acid 3-[bis-(4-chloro-phenyl)-methanesulfonyl]-2-oxo-propyl ester;
N-{3-[Bis-(4-chloro-phenyl)-methanesulfonyl]-2-oxo-propyl}-acetamide;
N-{3-[Bis-(4-chloro-phenyl)-methanesulfonyl]-2-oxo-propyl}-benzamide;
Benzyl-carbamic acid 3-[bis-(4-chloro-phenyl)-methanesulfonyl]-2-oxo-propyl ester;
1-[Bis-(4-chloro-phenyl)-methanesulfonyl]-3-methanesulfonyl-propan-2-one;
1-benzenesulfonyl-3-[bis-(4-chloro-phenyl)-methanesulfonyl]-propan-2-one;
1-[Bis-(4-chloro-phenyl)-methanesulfonyl]-3-phenyl-propan-2-one; and
1-[Bis-(4-chloro-phenyl)-methanesulfonyl]-3-phenoxy-propan-2-one.

8. A method for treating a chemokine associated disorder in a subject comprising administering to the subject an effective amount of a compound of Formula I or II:

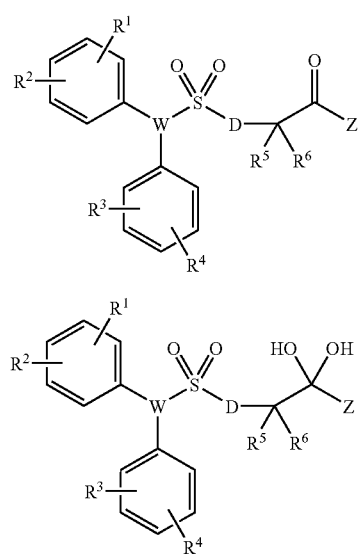

or a pharmaceutically acceptable salt of a compound of Formula I or II;
wherein:
D is $(CH_2)_n$, where n is 0 or 1;
$R^1$, $R^2$, $R^3$, and $R^4$ are each independently selected from H, $C_1$–$C_6$alkyl, $C_3$–$C_6$cycloalkyl, $C_3$–$C_6$ heterocycloalkyl, phenyl, halogen, or $CF_3$;
W is N, CH, or CF;
$R^5$ and $R^6$ are independently H or F;
Z is selected from the group consisting of:
$C_1$–$C_6$ alkyl, $CH_2Br$, $CH_2Cl$, $CF_3$, $CH_2F$, $CHF_2$, $CH_2R^7$, $CFR^7R^8$, $CF_2R^7$, $CH_2OR^7$, $CHFOR^7$, $CF_2OR^7$, $C(O)NR^7R^8$, $CO_2R^7$,

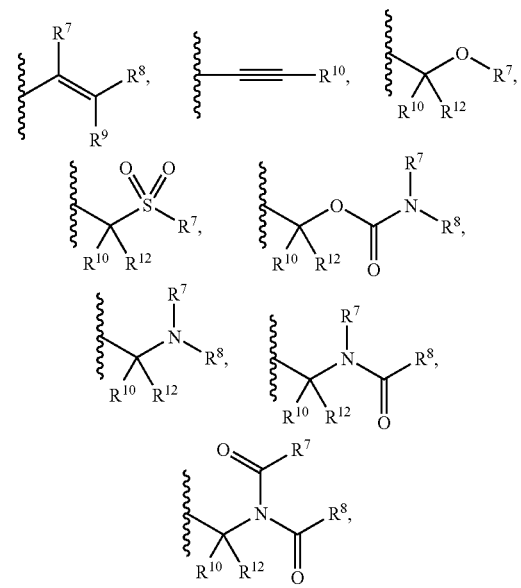

phenyl, $C_6$–$C_{12}$aryl, and $C_5$–$C_{12}$heteroaryl;
$R^7$, $R^8$, and $R^9$, are independently selected from the group consisting of H, $C_1$–$C_6$ alkyl, $CF_3$, $CCl_3$, $C_6$–$C_{12}$aryl, $C_6$–$C_{12}$aryl-$C_1$–$C_6$ alkyl-, $C_5$–$C_{12}$heteroaryl, and $C_5$–$C_{12}$heteroaryl-$C_1$–$C_6$alkyl-;
$R^{10}$ and $R^{12}$ are independently selected from the group consisting of F, H, $C_1$–$C_6$ alkyl, $CF_3$, $CCl_3$, $C_6$–$C_{12}$aryl, $C_6$–$C_{12}$aryl-$C_1$–$C_6$ alkyl-, $C_5$–$C_{12}$heteroaryl, and $C_5$–$C_{12}$heteroaryl-$C_1$–$C_6$alkyl-; and
wherein 2-(diphenyl-methanesulfonyl)-1-pyridin-2-yl-ethanone is not included.

9. The method according to claim 8,
wherein D is 0;
wherein W is CH;
wherein $R^1$, $R^2$, $R^3$, and $R^4$ are each independently selected from the group consisting of: H, $C_1$–$C_6$ alkyl, and halogen.

10. The method according to claim 9, wherein Z is selected from the group consisting of:
$CF_3$, $CH_2Cl$, $CH_2F$, $CHF_2$, $CH_2R^7$, $CFR^7R^8$, $CF_2R^7$, $CH_2OR^7$, $CHFOR^7$, and $CF_2OR^7$.

11. The method according to claim 9, wherein is Z is selected from the group consisting of:
wherein $R^{10}$ and $R^{12}$ are H or F; and
wherein Z is selected from the group consisting of:

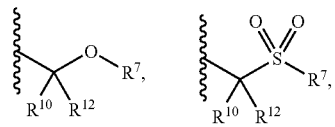

-continued

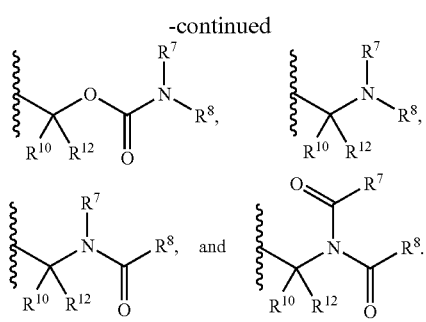

12. The method according to claim 11, wherein $R^{10}$ and $R^{12}$ are H.

13. The method according to claim 12, wherein $R^7$ and $R^8$ are each independently selected from the group consisting of H, $C_1$–$C_6$ alkyl, and $CF_3$.

14. The method according to claim 8, wherein the compound is selected from the group consisting of:
- 1-[Bis-(4-chloro-phenyl)-methanesulfonyl]-propan-2-one;
- 1-[Bis-(4-chloro-phenyl)-methanesulfonyl]-butan-2-one;
- 1-[Bis-(4-chloro-phenyl)-methanesulfonyl]-3-bromo-propan-2-one;
- 3-[Bis-(4-chloro-phenyl)-methanesulfonyl]-1,1,1-trifluoro-propan-2-one;
- 2-[Bis-(4-chloro-phenyl)-methanesulfonyl]-1-furan-2-yl-ethanone;
- 1-[Bis-(4-chloro-phenyl)-methanesulfonyl]-pent-3-yn-2-one;
- 3-[Bis-(4-chloro-phenyl)-methanesulfonyl]-1-fluoro-propan-2-one;
- 3-[Bis-(4-chloro-phenyl)-methanesulfonyl]-1,1-difluoro-propan-2-one;
- 1-[Bis-(4-chloro-phenyl)-methanesulfonyl]-3-phenyl-propan-2-one;
- 1-[Bis-(4-chloro-phenyl)-methanesulfonyl]-3-phenoxy-propan-2-one;
- 1-[Bis-(4-chloro-phenyl)-methanesulfonyl]-3-(4-methoxy-phenoxy)-propan-2-one;
- 1-[Bis-(4-chloro-phenyl)-methanesulfonyl]-3-(4-chloro-phenoxy)-propan-2-one;
- 1-[Bis-(4-chloro-phenyl)-methanesulfonyl]-3-(2,4-difluoro-phenoxy)-propan-2-one;
- 1-[Bis-(4-chloro-phenyl)-methanesulfonyl]-3-methoxy-propan-2-one;
- 1-[Bis-(4-chloro-phenyl)-methanesulfonyl]-pent-3-ene-2-one;
- 2-[Bis-(4-chloro-phenyl)-methanesulfonyl]-1-(1-methyl-1H-imidazol-2-yl)-ethanone;
- 5-(2-[Bis-(4-chloro-phenyl)-methanesulfonyl]-acetyl)-thiophene-2-carboxylic acid dimethylamide;
- 2-[Bis-(4-chloro-phenyl)-methanesulfonyl]-1-thiophen-2-yl-ethanone;
- 1-[Bis-(4-chloro-phenyl)-methanesulfonyl]-3,3-dimethyl-butan-2-one;
- 1-[Bis-(4-chloro-phenyl)-methanesulfonyl]-4-phenyl-butan-2-one;
- 4-[Bis-(4-chloro-phenyl)-methanesulfonyl]-3-oxo-butyric acid methyl ester;
- 4-[Bis-(4-chloro-phenyl)-methanesulfonyl]-N-(2-chloro-phenyl)-3-oxo-butyramide;
- 4-[Bis-(4-chloro-phenyl)-methanesulfonyl]-butan-2-one;
- Acetic acid 3-[bis-(4-chloro-phenyl)-methanesulfonyl]-2-oxo-propyl ester;
- 1-[Bis-(4-chloro-phenyl)-methanesulfonyl]-4,4,4-trifluoro-butan-2-one;
- 1-[Bis-(4-chloro-phenyl)-methanesulfonyl]-3-phenyl-methanesulfonyl-propan-2-one;
- 3-[Bis(4-fluorophenyl)methanesulfonyl]-1,1,1-trifluoro-propane-2,2-diol;
- 3-[Bis(4-trifluoromethyl-phenyl)methanesulfonyl]-1,1,1-trifluoropropane-2,2-diol;
- 3-[(4-Chlorophenyl)-(3,4-dichlorophenyl)methanesulfonyl]-1,1,1-trifluoropropane-2,2-diol;
- 3-[Biphen-4-yl-(4-chlorophenyl)methanesulfonyl]-1,1,1-trifluoropropane-2,2-diol;
- 3-[(4-Chlorophenyl)-(4-isobutylphenyl)methanesulfonyl]-1,1,1-trifluoropropane-2,2-diol;
- 3[(4-Chlorophenyl)-(4-isobutylphenyl)methanesulfonyl]-1,1,1-trifluoropropan-2-one;
- 1-[Bis-(4-chloro-phenyl)-methanesulfonyl]-3-(4-fluoro-phenyl)-propan-2-one;
- 2-[Bis-(4-chloro-phenyl)-methylsulfonyl]-1-pyridin-2-yl-ethanone;
- 1-[Bis-(4-chloro-phenyl)-methanesulfonyl]-1-fluoro-propan-2-one;
- 3-[Bis-(4-chloro-phenyl)-methanesulfonyl]-3,3-difluoro-butan-2-one;
- 1-[Bis-(4-chloro-phenyl)-methanesulfonyl]-3-fluoro-butan-2-one;
- (R)-1-[Bis-(4-chloro-phenyl)-methanesulfonyl]-3,3-difluoro-4-phenyl-pentan-2-one;
- (S)-1-[Bis-(4-chloro-phenyl)-methanesulfonyl]-3,3-difluoro-4-phenyl-pentan-2-one;
- 1-[Bis-(4-chloro-phenyl)-methanesulfonyl]-4-(3,4-dimethoxy-phenyl)-3,3-difluoro-butan-2-one;
- 3-[Bis-(4-chloro-phenyl)-methanesulfonyl]-N,N-dimethyl-2-oxo-propionamide;
- 1-[Bis-(4-chloro-phenyl)-methanesulfonyl]-3-hydroxy-propan-2-one;
- 1-[Bis-(4-chloro-phenyl)-methanesulfonyl]-3-methoxy-propan-2-one;
- 3-[Bis-(4-chloro-phenyl)-methanesulfonyl]-1,1-difluoro-1-methoxy-propan-2-one;
- 1-[Bis-(4-chloro-phenyl)-methanesulfonyl]-3,3-difluoro-butan-2-one;
- 1-[Bis-(4-chloro-phenyl)-methanesulfonyl]-4,4,4-trichloro-3,3-difluoro-butan-2-one;
- 1-[Bis-(4-chloro-phenyl)-methanesulfonyl]-3,3-difluoro-butan-2-one;
- 1-[Bis-(4-chloro-phenyl)-methanesulfonyl]-3,3-difluoro-4-methyl-pentan-2-one;
- 6-[Bis-(4-chloro-phenyl)-methanesulfonyl]-4,4-difluoro-5-oxo-hexanoic acid methyl ester;
- 3-[1-(4-Chloro-phenyl)-1-(3,4-dichloro-phenyl)-methanesulfonyl]-1,1,1-trifluoro-propan-2-one;
- 3-[Bis-(3,4-dichloro-phenyl)-methanesulfonyl]-1,1,1-trifluoro-propan-2-one;
- 1-Benzyloxy-3-[bis-(4-chloro-phenyl)-methanesulfonyl]-propan-2-one;
- 1-[1-(4-Chloro-phenyl)-1-(3,4-dichloro-phenyl)-methanesulfonyl]-4-(3,4-dimethoxy-phenyl)-3,3-difluoro-butan-2-one;
- 1-[Bis-(3,4-dichloro-phenyl)-methanesulfonyl]-4-(3,4-dimethoxy-phenyl)-3,3-difluoro-butan-2-one;
- 3,3,3-Trifluoro-2-oxo-propane-1-sulfonic acid bis-(4-chloro-phenyl)-amide;
- 4-(3,4-Dimethoxy-phenyl)-3,3-difluoro-2-oxo-butane-1-sulfonic acid bis-(4-chloro-phenyl)-amide;

4-(3,4-Dimethoxy-phenyl)-3,3-difluoro-2-oxo-butane-1-sulfonic acid (4-chloro-phenyl)-(3,4-dichloro-phenyl)-amide;
2-[Bis-(4-chloro-phenyl)-methanesulfonyl]-1-(5-methyl-furan-2-yl)-ethanone;
2-[Bis-(4-chloro-phenyl)-methanesulfonyl]-1-(5-nitro-furan-2-yl)-ethanone;
2-[Bis-(4-chloro-phenyl)-methanesulfonyl]-1-[5-(2,4-difluoro-phenyl)-furan-2-yl]-ethanone;
2-[Bis-(4-chloro-phenyl)-methanesulfonyl]-1-oxazol-2-yl-ethanone;
2-[Bis-(4-chloro-phenyl)-methanesulfonyl]-1-(5-phenyl-isoxazol-3-yl)-ethanone;
2-[Bis-(4-chloro-phenyl)-methanesulfonyl]-1-[5-(3,4-dichloro-phenyl)-isoxazol-3-yl]-ethanone;
2-[Bis-(4-chloro-phenyl)-methanesulfonyl]-1-[5-(2,4-dichloro-phenyl)-isoxazol-3-yl]-ethanone;
2-[Bis-(4-chloro-phenyl)-methanesulfonyl]-1-[3-(4-chloro-phenyl)-isoxazol-5-yl]-ethanone;
2-[Bis-(4-chloro-phenyl)-methanesulfonyl]-1-[3-(3-trifluoromethyl-phenyl)-isoxazol-5-yl]-ethanone;
2-[Bis-(4-chloro-phenyl)-methanesulfonyl]-1-[3-(2,4-dichloro-phenyl)-isoxazol-5-yl]-ethanone;
2-[Bis-(4-chloro-phenyl)-methanesulfonyl]-1-[3-(3-chloro-5-trifluoromethyl-pyridin-2-yl)-isoxazol-5-yl]-ethanone;
2-[Bis-(4-chloro-phenyl)-methanesulfonyl]-1-(5-nitro-thiophen-2-yl)-ethanone;
5-{2-[Bis-(4-chloro-phenyl)-methanesulfonyl]-ethanoyl}-thiophene-2-carboxylic acid dimethylamide;
5-{2-[Bis-(4-chloro-phenyl)-methanesulfonyl]-ethanoyl}-thiophene-2-carbonitrile;
2-[Bis-(4-chloro-phenyl)-methanesulfonyl]-1-thiazol-2-yl-ethanone;
2-[Bis-(4-chloro-phenyl)-methanesulfonyl]-1-(4,5-dihydro-thiazol-2-yl)-ethanone;
2-[Bis-(4-chloro-phenyl)-methanesulfonyl]-1-(1-oxo-4,5-dihydro-1H-1λ4-thiazol-2-yl)-ethanone;
2-[Bis-(4-chloro-phenyl)-methanesulfonyl]-1-(dioxo-4,5-dihydro-1H-1λ6-thiazol-2-yl)-ethanone;
2-[Bis-(4-chloro-phenyl)-methanesulfonyl]-1-(2-phenyl-thiazol-4-yl]-ethanone;
2-[Bis-(4-chloro-phenyl)-methanesulfonyl]-1-[2-(4-trifluoromethyl-phenyl)-thiazol-4-yl]-ethanone;
2-[Bis-(4-chloro-phenyl)-methanesulfonyl]-1-pyridin-2-yl-ethanone;
2-[Bis-(4-chloro-phenyl)-methanesulfonyl]-1-pyridin-4-yl-ethanone;
2-[Bis-(4-chloro-phenyl)-methanesulfonyl]-1-pyrimidin-2-yl-ethanone;
1-Benzofuran-2-yl-2-[bis-(4-chloro-phenyl)-methanesulfonyl]-ethanone;
2-[Bis-(4-chloro-phenyl)-methanesulfonyl]-1-[5-nitro-benzofuran-2-yl]-ethanone;
2-[Bis-(4-chloro-phenyl)-methanesulfonyl]-1-(7-hydroxy-benzofuran-2-yl)-ethanone.
1-[Bis-(4-chloro-phenyl)-methanesulfonyl]-3-(4-trifluoromethyl-phenoxy)-propan-2-one;
1-[Bis-(4-chloro-phenyl)-methanesulfonyl]-3-(4-methanesulfonyl-phenoxy)-propan-2-one;
Ethyl-carbamic acid 3-[bis-(4-chloro-phenyl)-methanesulfonyl]-2-oxo-propyl ester;
N-{3-[Bis-(4-chloro-phenyl)-methanesulfonyl]-2-oxo-propyl}-acetamide;
N-{3-[Bis-(4-chloro-phenyl)-methanesulfonyl]-2-oxo-propyl}-benzamide;
Benzyl-carbamic acid 3-[bis-(4-chloro-phenyl)-methanesulfonyl]-2-oxo-propyl ester;
1-[Bis-(4-chloro-phenyl)-methanesulfonyl]-3-methanesulfonyl-propan-2-one;
1-benzenesulfonyl-3-[bis-(4-chloro-phenyl)-methanesulfonyl]-propan-2-one;
1-[Bis-(4-chloro-phenyl)-methanesulfonyl]-3-phenyl-propan-2-one; and
1-[Bis-(4-chloro-phenyl)-methanesulfonyl]-3-phenoxy-propan-2-one.

15. A pharmaceutical composition comprising a compound according to any one of claims 1–7, and a pharmaceutically acceptable carrier, excipient, or diluent.

* * * * *